(12) United States Patent
Masakari et al.

(10) Patent No.: US 11,198,852 B2
(45) Date of Patent: Dec. 14, 2021

(54) AMADORIASE HAVING ENHANCED ANIONIC SURFACTANT TOLERANCE

(71) Applicant: Kikkoman Corporation, Noda (JP)

(72) Inventors: Yosuke Masakari, Noda (JP); Airi Komatsuzaki, Noda (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 15/523,806

(22) PCT Filed: Nov. 6, 2015

(86) PCT No.: PCT/JP2015/081410
§ 371 (c)(1),
(2) Date: May 2, 2017

(87) PCT Pub. No.: WO2016/072520
PCT Pub. Date: May 12, 2016

(65) Prior Publication Data
US 2018/0237755 A1 Aug. 23, 2018

(30) Foreign Application Priority Data

Nov. 7, 2014 (JP) .............................. JP2014-227548

(51) Int. Cl.
*C12N 9/06* (2006.01)
*C12N 15/00* (2006.01)
(Continued)

(52) U.S. Cl.
CPC ........... *C12N 9/0032* (2013.01); *C12N 15/09* (2013.01); *C12Q 1/26* (2013.01)

(58) Field of Classification Search
CPC .................................................. C12N 9/0032
See application file for complete search history.

(56) References Cited

U.S. PATENT DOCUMENTS 5,370,990 A 12/1994 Staniford et al.
7,070,948 B1 7/2006 Sakaue et al.
(Continued)

FOREIGN PATENT DOCUMENTS

EP 3061819 A1 8/2016
JP 05-033997 B2 5/1993
(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Foley & Lardner LLP

(57) ABSTRACT

The present invention provides a composition that enables measurement of glycated hemoglobin in the presence of a stronger surfactant than conventional surfactants. To this end, the present invention provides an amadoriase in which one or more amino acids have been substituted at positions corresponding to positions selected from the group consisting of positions 80, 71, 175, 172, 279, 12, 9, 77, 30, 28, 13, 3, 4, 286, 204, 338, 44, 340, and 194 of the amadoriase derived from the genus *Coniochaeta* having the amino acid sequence as shown in SEQ ID NO: 1 as well as a composition for measurement of glycated hemoglobin comprising an amadoriase that retains activity in the presence of an anionic surfactant. The present invention can provide an enzyme and a composition for measurement of glycated hemoglobin that sufficiently remain stable even when exposed to anionic surfactants.

17 Claims, 5 Drawing Sheets

Specification includes a Sequence Listing.

(51) Int. Cl.
*C12N 1/20* (2006.01)
*C12N 15/09* (2006.01)
*C12Q 1/26* (2006.01)

(56) References Cited

U.S. PATENT DOCUMENTS

| | | | | |
|---|---|---|---|---|
| 8,497,083 | B2* | 7/2013 | Ikebukuro | G01N 33/723 |
| | | | | 435/25 |
| 9,062,286 | B2* | 6/2015 | Ichiyanagi | C12N 9/0032 |
| 9,708,586 | B2* | 7/2017 | Ichiyanagi | C12N 15/63 |
| 10,619,183 | B2* | 4/2020 | Masakari | G01N 33/723 |
| 10,767,211 | B2* | 9/2020 | Ichiyanagi | C12Q 1/26 |
| 10,934,530 | B2* | 3/2021 | Ichiyanagi | G01N 33/72 |
| 2003/0162242 | A1 | 8/2003 | Yonehara | |
| 2005/0101771 | A1 | 5/2005 | Kouzuma et al. | |
| 2007/0178547 | A1 | 8/2007 | Taniguchi et al. | |
| 2008/0113381 | A1 | 5/2008 | Matsuoka et al. | |
| 2008/0233605 | A1 | 9/2008 | Taniguchi et al. | |
| 2008/0295259 | A1 | 12/2008 | Ueda et al. | |
| 2009/0081718 | A1 | 3/2009 | Yonehara et al. | |
| 2011/0003361 | A1 | 1/2011 | Kurosawa et al. | |
| 2011/0195444 | A1 | 8/2011 | Hirao et al. | |
| 2012/0208226 | A1* | 8/2012 | Ikebukuro | C12N 9/0022 |
| | | | | 435/25 |
| 2013/0171676 | A1 | 7/2013 | Murakami et al. | |
| 2013/0267007 | A1 | 10/2013 | Ichiyanagi et al. | |
| 2014/0234886 | A1 | 8/2014 | Aisaka et al. | |
| 2015/0118700 | A1* | 4/2015 | Ichiyanagi | C12N 9/0032 |
| | | | | 435/14 |
| 2016/0186232 | A1* | 6/2016 | Masakari | C12N 9/0032 |
| | | | | 435/25 |
| 2016/0251695 | A1 | 9/2016 | Masakari et al. | |

FOREIGN PATENT DOCUMENTS

| | | |
|---|---|---|
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2006-325547 A | 12/2006 |
| JP | 2008-201968 A | 9/2008 |
| JP | 2009-000128 A | 1/2009 |
| JP | 2010-035469 A | 2/2010 |
| JP | 2010-057474 A | 3/2010 |
| JP | 2010-104278 A | 5/2010 |
| JP | 2010-115189 A | 5/2010 |
| JP | 2011-229526 A | 11/2011 |
| JP | 2013-500729 A | 1/2013 |
| WO | WO 97/13872 A1 | 4/1997 |
| WO | WO 02/06519 A1 | 1/2002 |
| WO | WO 2004/104203 A1 | 12/2004 |
| WO | WO 2005/049857 A1 | 6/2005 |
| WO | WO 2005/087946 A1 | 9/2005 |
| WO | WO 2006/120976 A1 | 11/2006 |
| WO | WO 2007/072941 A1 | 6/2007 |
| WO | WO 2010/041419 A1 | 4/2010 |
| WO | WO 2010/041715 A1 | 4/2010 |
| WO | WO 2011/015325 A1 | 2/2011 |
| WO | WO 2011/015326 A2 | 2/2011 |
| WO | WO 2012/018094 A1 | 2/2012 |
| WO | WO 2012/020744 A1 | 2/2012 |
| WO | WO-2013162035 A1 * 10/2013 ............... C12Q 1/26 | |
| WO | WO 2015/020200 A1 | 2/2015 |
| WO | WO 2015/060429 A1 | 4/2015 |

OTHER PUBLICATIONS

Supplementary European Search Report dated Apr. 25, 2018, in EP 15856363.5.
International Search Report dated Feb. 9, 2016, in PCT/JP2015/081410.
Ferri et al., "Cloning and Expression of Fructosyl-amine Oxidase from Marine Yeast *Pichia* Species N1-1," Mar. Biotechnol., 2004, 6:625-632.
Ferri et al., "Isolation and characterization of a fructosyl-amine oxidase from an *Arthrobacter* sp.," Biotechnology Letters, 2005, 27:27-32.
Fujiwara et al., "Alteration of Substrate Specificity of Fructosyl-Amino Acid Oxidase from *Ulocladium* sp. JS-103," Journal of Bioscience and Bioengineering, 2006, 102(3):241-243.
Fujiwara et al., "Alteration of substrate specificity of fructosyl-amino acid oxidase from *Fusarium oxysporum*," Appl. Microbiol. Biotechnol., 2007, 74:813-819.
Hirokawa et al., "Molecular cloning and expression of novel fructosyl peptide oxidases and their application for the measurement of glycated protein," Biochemical and Biophysical Research Communications, 2003, 311:104-111.
Hirokawa et al., "Recombinant *Agrobacterium* AgaE-like Protein with Fructosyl Amino Acid Oxidase Activity," Biosci. Biotechnol. Biochem., 2002, 66(11):2323-2329.
Jeong et al., "The veA gene is necessary for the inducible expression by fructosyl amines of the *Aspergillus nidulans faoA* gene encoding fructosyl amino acid oxidase (amadoriase, EC 1.5.3)," Arch. Microbiol., 2002, 178:344-350.
Kim et al., "Motif-Based Search for a Novel Fructosyl Peptide Oxidase from Genome Databases," Biotechnology and Bioengineering, Jun. 15, 2010, 106(3):358-366.
Sakai et al., "Purification and Properties of Fructosyl Lysine Oxidase from *Fusarium oxysporum* S-1F4," Biosci. Biotech. Biochem., 1995, 59(3):487-491.
Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.
Yoshida et al., "Primary structures of fungal fructosyl amino acid oxidases and their application to the measurement of glycated proteins," Eur. J. Biochem., 1996, 242:499-505.
Third party submission dated Sep. 6, 2019, in JP 2016-557839, 33 pages.

* cited by examiner

| | | | | | | | | | | | | | | | | | | | |
|---|---|---|---|---|---|---|---|---|---|---|---|---|---|---|---|---|---|---|---|
| Co | 399 | E E M A Y Q | W R W R P G | - | G D A L | K S | R R | A A | P P | K D L | A D | M P G W | K H D | P K L | - - - - - - - | - - - - | 437 |
| Et | 399 | Q E M A G A | W R W R P G | - | G D A L | R S | R R | G A | A P | A K D L | A E | M P G W | K H D | A H L | - - - - - - - | - - - - | 437 |
| Py | 397 | A D L A Q A | W R W R P G | - | G D D A L | Q S | R R | R A | A P | A K D L | A D | M P G W | N H D | - E S | P R A K L - - | - - - - | 440 |
| Ar | 400 | D D L A H A | W R W R P G | Q | G D D A L | K S | R R | A A | A P | A K D L | A D | M P G W | K H D | D S G | N A T S G T S | S S E | 449 |
| Cc | 397 | E D L A H A | W R W R P G | - | G D D A L | K S | R R | R A | A P | A K D L | A D | L P G W | N H D | - D V | V K S K L - - | - - - - | 440 |
| Nv | 399 | D D L A E S | W R W R P G | - | Q G D D A L | A R | R R | R A | A P | A K D L | A D | M P G W | K H D | Q D S | E S R - - - - | - - - - | 441 |
| Cn | 399 | E D L A E D | W R W R P G | T | Q G D D A L | K S | R R | R A | A P | A K D L | A D | M P G W | N H D | E P S | D D M D V K D | V A | 477 |
| Pn | 395 | D D L A E D | W R W R P G | - | Q G D D A L | A R | R R | - R | A P | A R D L | A D | M P G W | N H D | - K P | R A N L - - - | - - - - | 437 |
| An | 399 | S V F K D A | W R W R P G | - | S G D D A L | K S | R R | R A | A P | A K D L | A D | M P G W | R N E | A K M | - - - - - - - | - - - - | 438 |
| En | 399 | S V F K D A | W R W R P G | - | S G D D A L | K S | R R | R A | A P | A K D L | A D | M P G W | R N E | A K M | - - - - - - - | - - - - | 438 |
| Ui | 397 | D D L A H A | W R W R P G | T | G D D A L | K S | R R | A A | A P | A K D L | A D | M P G W | N H D | G E A | P R A K L - - | - - - - | 441 |
| Pj | 399 | Q D L A G A | W R W R P G | - | G D A L | K S | K R | S A | P A | R A K D L | A E | M P G W | K H D | A K L | - - - - - - - | - - - - | 437 |

| | | | |
|---|---|---|---|
| Co | 437 | - - - - - - - - - - - - - - - - - - - - - - - - - - - - - | 437 (SEQ ID NO: 1) |
| Et | 437 | - - - - - - - - - - - - - - - - - - - - - - - - - - - - - | 437 (SEQ ID NO: 3) |
| Py | 440 | - - - - - - - - - - - - - - - - - - - - - - - - - - - - - | 440 (SEQ ID NO: 4) |
| Ar | 450 | - H K L - - - - - - - - - - - - - - - - - - - - - - - - - | 452 (SEQ ID NO: 5) |
| Cc | 440 | - - - - - - - - - - - - - - - - - - - - - - - - - - - - - | 440 (SEQ ID NO: 6) |
| Nv | 441 | - - - - - - - - - - - - - - - - - - - - - - - - - - - - - | 441 (SEQ ID NO: 7) |
| Cn | 449 | V S L A S V K I G E N I G E K V V E D G A R V G V K V L A | 477 (SEQ ID NO: 8) |
| Pn | 437 | - - - - - - - - - - - - - - - - - - - - - - - - - - - - - | 437 (SEQ ID NO: 9) |
| An | 438 | - - - - - - - - - - - - - - - - - - - - - - - - - - - - - | 438 (SEQ ID NO: 10) |
| En | 438 | - - - - - - - - - - - - - - - - - - - - - - - - - - - - - | 438 (SEQ ID NO: 11) |
| Ui | 441 | - - - - - - - - - - - - - - - - - - - - - - - - - - - - - | 441 (SEQ ID NO: 12) |
| Pj | 437 | - - - - - - - - - - - - - - - - - - - - - - - - - - - - - | 437 (SEQ ID NO: 13) |

AMADORIASE HAVING ENHANCED ANIONIC SURFACTANT TOLERANCE

CROSS-REFERENCE TO RELATED APPLICATIONS

This application is a National Stage application of PCT/JP2015/081410, filed Nov. 6, 2015, which claims priority from Japanese application JP 2014-227548, filed Nov. 7, 2014.

TECHNICAL FIELD

The present invention relates to an amadoriase excellent in surfactant tolerance, such as an amadoriase having enhanced tolerance to an anionic surfactant, a gene and recombinant DNA thereof, and a method for producing such amadoriase. The present invention also relates to an amadoriase that can be effectively used as a diagnostic enzyme for diabetes or an amadoriase that can be effectively used for a kit for measuring a diabetes marker.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, glycated hemoglobin (HbA1c) has drawn attention as a glycemic control marker significant for diagnosis of diabetic patients and control of conditions in the field of clinical diagnosis of diabetes mellitus. The blood HbA1c level reflects the average blood glucose level for a given period of time in the past, and the measured value thereof serves as a significant indicator for diagnosis and control of diabetes conditions.

As a method for rapidly and readily measuring HbA1c, an enzymatic method using an amadoriase has been proposed, in which HbA1c is decomposed with e.g., a protease, and α-fructosyl valyl histidine (hereinafter referred to as "αFVH") or α-fructosyl valine (hereinafter referred to as "αFV") released from a β chain amino terminus thereof is quantified (see, for example, Patent Documents 1 to 7). In reality, the method of cleaving αFV from HbA1c is associated with the problem in that accurate measurement values may not be obtained since the effect of contaminants and the like is significant. To obtain more accurate measurement values, methods of measuring αFVH are mainly employed in particular at present.

An amadoriase catalyzes a reaction of oxidizing iminodiacetic acid or a derivative thereof (also referred to as an "Amadori compound") in the presence of oxygen to produce glyoxylic acid or α-ketoaldehyde, an amino acid or a peptide, and hydrogen peroxide.

Amadoriases have been found in bacteria, yeast, and fungi. For example, amadoriases having enzymatic activity on αFVH and/or αFV, which is particularly useful for measurement of HbA1c, and derived from the genera Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium, and Arthrobacter have been reported (e.g., Patent Documents 1 and 6 to 15 and Non-Patent Documents 1 to 11). In some of these documents, an amadoriase may also be referred to as, for example, ketoamine oxidase, fructosyl amino acid oxidase, fructosyl peptide oxidase, or fructosyl amine oxidase.

Regarding measurement of HbA1c, it is known that reagent compositions for measurement contain excessive amounts of amadoriase. For example, when measuring HbA1c at a final concentration of 0.36 μM, amadoriase is used at a concentration of 1.4 kU/L, which is a concentration at which 1.4 mM of a substrate per minute can be reacted with the amadoriase (see Patent Document 16). The mainstream approach to measure HbA1c with an amadoriase is to use an automated analyzer. The amadoriase and substrate are often reacted for about 5 minutes to 25 minutes and subjected to measurement therein. The reason to include excessive amounts of amadoriase is to allow the amadoriase to react sufficiently with the substrate during a short measurement time as mentioned above; and further, if a substance which has a negative effect on the reactivity and stability of the amadoriase is present in the composition for measurement, excessive amounts of amadoriase must be formulated as a countermeasure against such effect.

As a pretreatment method for measuring HbA1c in whole blood or erythrocytes by using an amadoriase, blood cells are lysed with a surfactant (see, for example, Patent Documents 2 and 16 to 18). When degrading HbA1c with a protease, a surfactant is used in some methods as an accelerant (see, for example, Patent Document 19). Therefore, surfactants are required when measuring HbA1c with an amadoriase; however, the possibility is extremely high that the surfactant will denature the amadoriase when an HbA1c solution treated with a surfactant and a protease is mixed with the amadoriase solution before initiating a quantitative reaction of HbA1c, as well as during storage of a surfactant-amadoriase mixture. Presently used HbA1c measurement kits contain excessive amounts of amadoriase than required, and further are formulated together with stabilizers and are able to achieve accurate measurement; however, the cost of the kit inevitably increases due to use of excessive reagents. Further, if it is possible to use a more effective surfactant than those presently used, the degradation efficiency of HbA1c with protease can be improved and it his highly possible that the measurement sensitivity of HbA1c can be improved. In addition, surfactants have solubilizing effects on insoluble peptide fragments derived from hemoglobin and HbA1c. Because of the effect, the surfactant can prevent turbidity, thereby contributing to improvement of measurement accuracy. Therefore, when formulating amadoriase as an enzyme for clinical diagnosis of diabetes into a reagent kit, one desirable property of the enzyme is to remain stable in a solution containing a surfactant.

Although individual measurement conditions vary; disclosure of the stability of various amadoriases in liquids can be found in literature known in the art: in a case where 5 mM ethylenediaminetetraacetic acid and 3% glycine are added in a solution containing an amadoriase derived from Coniochaeta sp. NISL 9330 strain, it is reported that a residual activity of 79% is maintained 7 days later at 30° C. (see, for example, Patent Document 20). Further, in another case where 3% L-alanine, 3% glycine, or 3% sarcosine is added in a solution containing a fructosyl amino acid oxidase derived from *Fusarium oxysporum* IFO-9972 strain, it is reported that 100% or more residual activity is maintained 2 days later at 37° C. (see, for example, Patent Document 21). However, no surfactants are added to the above solutions containing the amadoriase protein and the literature is silent on lowering effects of surfactants.

It was reported that surfactant tolerance of an amadoriase was improved via introduction of a variation (see, for example, Patent Document 22). Patent Document 22 describes mutations which improve the residual activity of amadoriase in the presence of cationic surfactants, and the residual activity of CFP-D7 in which mutations were accumulated was 100% or more in the presence of 0.04% of hexadecyltrimethylammonium chloride, which is a cationic surfactant, and that of CFP-D was 12.7% before introduction of the mutations. In contrast, the residual activity of CFP-D was 11.3% and that of CFP-D7 was 3.92% in the presence of 0.04% of sodium dodecyl sulfate. That is, residual activity was decreased in such a case. Accordingly, even if cationic surfactant tolerance is enhanced, it cannot be said that anionic surfactant tolerance will also be enhanced. Furthermore, stabilizers and buffers capable of maintaining the residual activity of an amadoriase or lowering a reduction of the residual activity in the presence of an anionic surfactant have not been reported.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2012/020744
Patent Document 17: WO 2005/87946
Patent Document 18: WO 2002/06519
Patent Document 19: WO 2006/120976
Patent Document 20: JP 2006-325547 A
Patent Document 21: JP 2009-000128 A
Patent Document 22: WO 2015/020200

Non-Patent Documents

Non-Patent Document 1: Biochem. Biophys. Res. Commun., 311, 104-11, 2003
Non-Patent Document 2: Biotechnol. Bioeng., 106, 358-66, 2010
Non-Patent Document 3: J. Biosci. Bioeng., 102, 241-3, 2006
Non-Patent Document 4: Eur. J. Biochem., 242, 499-505, 1996
Non-Patent Document 5: Arch. Microbiol., 178, 344-50, 2002
Non-Patent Document 6: Mar. Biotechnol., 6, 625-32, 2004
Non-Patent Document 7: Biosci. Biotechnol. Biochem., 59, 487-91, 1995
Non-Patent Document 8: Appl. Microbiol. Biotechnol., 74, 813-819, 2007
Non-Patent Document 9: Biosci. Biotechnol. Biochem., 66, 1256-61, 2002
Non-Patent Document 10: Biosci. Biotechnol. Biochem., 66, 2323-29, 2002
Non-Patent Document 11: Biotechnol. Letters 27, 27-32, 2005

SUMMARY OF THE INVENTION

Objects to be Attained by the Invention

As described above, amadoriases have been used excessively in the art so as to react sufficiently with the substrate during measurement. The present inventors found that surfactants are a component capable of negatively affecting the stability of amadoriases to a significant extent. As such, if an enzyme having surfactant tolerance superior to those of conventional amadoriases can be prepared, then it is expected that such enzyme can make great contributions such as in realizing improved convenience in distribution of the enzyme and kit, reduced costs by reducing amounts of the amadoriase and the stabilizers formulated in the kit, and improved sensitivity for measurement of HbA1c by enabling formulation of strong surfactants. Therefore, it is an object of the present invention to provide an amadoriase having surfactant tolerance superior to those of conventional amadoriases, and it is another object to provide a reagent composition that enables quantification of HbA1c or a glycated peptide derived therefrom HbA1c even in the presence of a surfactant.

Means for Attaining the Objects

Under the present situation where information regarding conferring surfactant tolerance to enzymes has scarcely been disclosed, the present inventors have conducted intensive studies. As a result, the present inventors found that the above objectives can be attained by introducing a particular amino acid residue substitution into the amadoriase derived from the genus *Coniochaeta* and further by incorporating an amadoriase retaining its activity in the presence of a surfactant into a reagent composition. This has led to the completion of the present invention.

The present invention encompasses the following.

[1] An amadoriase having surfactant tolerance, which is selected from the group consisting of amadoriases described below:

(i) an amadoriase having 20% or more residual activity (%) after sodium dodecyl sulfate is added thereto to a final concentration of 0.03% (w/v) and allowed to stand at 30° C. for 5 minutes, compared with the case in which no sodium dodecyl sulfate is added (100%), and having activity on a glycated substrate;

(ii) an amadoriase comprising an amino acid sequence in which, when aligned with the amino acid sequence as shown in SEQ ID NO: 1, one or more amino acids at positions corresponding to positions selected from the group consisting of positions 80, 71, 175, 172, 279, 12, 9, 77, 30, 28, 13, 3, 4, 286, 204, 338, 44, 340, and 194 in the amino acid sequence as shown in SEQ ID NO: 1 are substituted, and having activity on a glycated substrate;

(iii) the amadoriase as defined in (ii) comprising an amino acid sequence resulting from substitution, deletion, or addition of one or several amino acids at positions other than positions corresponding to positions 80, 71, 175, 172, 279, 12, 9, 77, 30, 28, 13, 3, 4, 286, 204, 338, 44, 340, and 194 in the amino acid sequence as shown in SEQ ID NO: 1, and having activity on a glycated substrate;

(iv) the amadoriase as defined in (iii) comprising an amino acid sequence having 70% or higher sequence identity with the amino acid sequence as shown in SEQ ID NO: 1, SEQ ID NO: 94, or SEQ ID NO: 110 over the full length and having activity on a glycated substrate;

(v) the amadoriase as defined in (iv) comprising an amino acid sequence exhibiting 70% or higher sequence identity with the amino acid sequence as shown in SEQ ID NO: 1, SEQ ID NO: 94, or SEQ ID NO: 110 over the full length and 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region of corresponding positions of the amadoriase, and having activity on a glycated substrate; and (vi) the amadoriase as defined in any of (ii) to (v), wherein when sodium dodecanoylsarcosinate is added to a final concentration of 0.15% (w/v) to an amadoriase resulting from substitution of one or more amino acids at positions corresponding to positions selected from the group consisting of positions 80, 71, 175, 172, 279, 12, 9, 77, 30, 28, 13, 3, 4, 286, 204, 338, 44, 340, and 194 in the amino acid sequence as shown in SEQ ID NO: 1 and to an amadoriase not having such amino acid substitutions, and the amadoriases are allowed to stand at 30° C. for 5 minutes, the amadoriase exhibits a residual activity increased by 3% or more compared with the amadoriase not having such amino acid substitutions, in terms of comparison of residual activity (%) values.

[2] The amadoriase according to [1], comprising one or more of the following:

(a) an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, asparagine, glutamine, or histidine;

(b) an amino acid sequence in which, when aligned with the amino acid sequence as shown in SEQ ID NO: 1, the amino acid at the position corresponding to methionine at position 71 in the amino acid sequence as shown in SEQ ID NO: 1 is leucine, isoleucine, alanine, glycine, valine, or cysteine;

(c) an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, histidine, or lysine;

(d) an amino acid sequence in which, when aligned with the amino acid sequence as shown in SEQ ID NO: 1, the amino acid at the position corresponding to phenylalanine at position 172 in the amino acid sequence as shown in SEQ ID NO: 1 is glutamic acid, aspartic acid, tyrosine, or glutamine;

(e) an amino acid sequence in which, when aligned with the amino acid sequence as shown in SEQ ID NO: 1, the amino acid at the position corresponding to valine at position 279 in the amino acid sequence as shown in SEQ ID NO: 1 is isoleucine or cysteine;

(f) an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine, leucine, cysteine, or methionine;

(g) an amino acid sequence in which, when aligned with the amino acid sequence as shown in SEQ ID NO: 1, the amino acid at the position corresponding to arginine at position 9 in the amino acid sequence as shown in SEQ ID NO: 1 is threonine, serine, asparagine, or glutamine;

(h) an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid, glutamic acid, lysine, or asparagine;

(i) an amino acid sequence in which, when aligned with the amino acid sequence as shown in SEQ ID NO: 1, the amino acid at the position corresponding to serine at position 30 in the amino acid sequence as shown in SEQ ID NO: 1 is threonine, valine, leucine, or isoleucine;

(j) an amino acid sequence in which, when aligned with the amino acid sequence as shown in SEQ ID NO: 1, the amino acid at the position corresponding to valine at position 28 in the amino acid sequence as shown in SEQ ID NO: 1 is isoleucine, methionine, alanine, or cysteine;

(k) an amino acid sequence in which, when aligned with the amino acid sequence as shown in SEQ ID NO: 1, the amino acid at the position corresponding to valine at position 13 in the amino acid sequence as shown in SEQ ID NO: 1 is isoleucine, leucine, cysteine, or methionine;

(l) an amino acid sequence in which, when aligned with the amino acid sequence as shown in SEQ ID NO: 1, the amino acid at the position corresponding to serine at position 3 in the amino acid sequence as shown in SEQ ID NO: 1 is threonine;

(m) an amino acid sequence in which, when aligned with the amino acid sequence as shown in SEQ ID NO: 1, the amino acid at the position corresponding to asparagine at position 4 in the amino acid sequence as shown in SEQ ID NO: 1 is proline;

(n) an amino acid sequence in which, when aligned with the amino acid sequence as shown in SEQ ID NO: 1, the amino acid at the position corresponding to phenylalanine at position 286 in the amino acid sequence as shown in SEQ ID NO: 1 is tyrosine or tryptophan;

(o) an amino acid sequence in which, when aligned with the amino acid sequence as shown in SEQ ID NO: 1, the amino acid at the position corresponding to glutamic acid at position 204 in the amino acid sequence as shown in SEQ ID NO: 1 is alanine, leucine, isoleucine, valine, or cysteine;

(p) an amino acid sequence in which, when aligned with the amino acid sequence as shown in SEQ ID NO: 1, the amino acid at the position corresponding to aspartic acid at position 338 in the amino acid sequence as shown in SEQ ID NO: 1 is alanine, leucine, isoleucine, valine, or cysteine;

(q) an amino acid sequence in which, when aligned with the amino acid sequence as shown in SEQ ID NO: 1, the amino acid at the position corresponding to glutamic acid at position 44 in the amino acid sequence as shown in SEQ ID NO: 1 is lysine, arginine, or histidine;

(r) an amino acid sequence in which, when aligned with the amino acid sequence as shown in SEQ ID NO: 1, the amino acid at the position corresponding to glutamic acid at position 340 in the amino acid sequence as shown in SEQ ID NO: 1 is lysine, arginine, or histidine; and (s) an amino acid sequence in which, when aligned with the amino acid sequence as shown in SEQ ID NO: 1, the amino acid at the position corresponding to aspartic acid at position 194 in the amino acid sequence as shown in SEQ ID NO: 1 is lysine, arginine, histidine, alanine, leucine, isoleucine, valine, or cysteine.

[3] The amadoriase according to [2], comprising one or more of the following:

(a) an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, asparagine, glutamine, or histidine;

(b) an amino acid sequence in which, when aligned with the amino acid sequence as shown in SEQ ID NO: 1, the amino acid at the position corresponding to methionine at position 71 in the amino acid sequence as shown in SEQ ID NO: 1 is leucine, isoleucine, alanine, valine, or cysteine;

(c) an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, lysine, or histidine;

(d) an amino acid sequence in which, when aligned with the amino acid sequence as shown in SEQ ID NO: 1, the amino acid at the position corresponding to phenylalanine at position 172 in the amino acid sequence as shown in SEQ ID NO: 1 is glutamic acid, aspartic acid, tyrosine, or glutamine;

(e) an amino acid sequence in which, when aligned with the amino acid sequence as shown in SEQ ID NO: 1, the amino acid at the position corresponding to valine at position 279 in the amino acid sequence as shown in SEQ ID NO: 1 is isoleucine or cysteine;

(f) an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine or leucine;

(g) an amino acid sequence in which, when aligned with the amino acid sequence as shown in SEQ ID NO: 1, the amino acid at the position corresponding to arginine at position 9 in the amino acid sequence as shown in SEQ ID NO: 1 is threonine, asparagine, or glutamine;

(h) an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid, glutamic acid, lysine, or asparagine;

(i) an amino acid sequence in which, when aligned with the amino acid sequence as shown in SEQ ID NO: 1, the amino acid at the position corresponding to serine at position 30 in the amino acid sequence as shown in SEQ ID NO: 1 is threonine or valine;

(j) an amino acid sequence in which, when aligned with the amino acid sequence as shown in SEQ ID NO: 1, the amino acid at the position corresponding to valine at position 28 in the amino acid sequence as shown in SEQ ID NO: 1 is isoleucine or methionine;

(k) an amino acid sequence in which, when aligned with the amino acid sequence as shown in SEQ ID NO: 1, the amino acid at the position corresponding to valine at position 13 in the amino acid sequence as shown in SEQ ID NO: 1 is leucine;

(l) an amino acid sequence in which, when aligned with the amino acid sequence as shown in SEQ ID NO: 1, the amino acid at the position corresponding to phenylalanine at position 286 in the amino acid sequence as shown in SEQ ID NO: 1 is tyrosine;

(m) an amino acid sequence in which, when aligned with the amino acid sequence as shown in SEQ ID NO: 1, the amino acid at the position corresponding to glutamic acid at position 204 in the amino acid sequence as shown in SEQ ID NO: 1 is alanine;

(n) an amino acid sequence in which, when aligned with the amino acid sequence as shown in SEQ ID NO: 1, the amino acid at the position corresponding to aspartic acid at position 338 in the amino acid sequence as shown in SEQ ID NO: 1 is alanine;

(o) an amino acid sequence in which, when aligned with the amino acid sequence as shown in SEQ ID NO: 1, the amino acid at the position corresponding to glutamic acid at position 44 in the amino acid sequence as shown in SEQ ID NO: 1 is lysine;

(p) an amino acid sequence in which, when aligned with the amino acid sequence as shown in SEQ ID NO: 1, the amino acid at the position corresponding to glutamic acid at position 340 in the amino acid sequence as shown in SEQ ID NO: 1 is lysine; and (q) an amino acid sequence in which, when aligned with the amino acid sequence as shown in SEQ ID NO: 1, the amino acid at the position corresponding to aspartic acid at position 194 in the amino acid sequence as shown in SEQ ID NO: 1 is lysine or alanine.

[4] The amadoriase according to [1], comprising an amino acid sequence in which, when aligned with the amino acid sequence as shown in SEQ ID NO: 1, the amino acid at the position corresponding to position 80 and the amino acid at the position corresponding to position 71 in the amino acid sequence as shown in SEQ ID NO: 1 are substituted and has activity on a glycated substrate.

[5] The amadoriase according to [4], comprising an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, asparagine, glutamine, or histidine, and when aligned with the amino acid sequence as shown in SEQ ID NO: 1, the amino acid at the position corresponding to methionine at position 71 in the amino acid sequence as shown in SEQ ID NO: 1 is leucine, isoleucine, alanine, glycine, valine, or cysteine.

[6] The amadoriase according to [5], comprising an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, and when aligned with the amino acid sequence as shown in SEQ ID NO: 1, the amino acid at the position corresponding to methionine at position 71 in the amino acid sequence as shown in SEQ ID NO: 1 is leucine.

[7] The amadoriase according to any of [4] to [6], further comprising an amino acid sequence in which, when aligned with the amino acid sequence as shown in SEQ ID NO: 1, the amino acid at the position corresponding to position 77 in the amino acid sequence as shown in SEQ ID NO: 1 is substituted and having activity on a glycated substrate.

[8] The amadoriase according to [6] or [7], further comprising an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid or glutamic acid.

[9] The amadoriase according to [8], comprising an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid.

[10] The amadoriase according to any of [1] to [9], comprising an amino acid sequence in which, when aligned with the amino acid sequence as shown in SEQ ID NO: 1, the amino acid at the position corresponding to position 175 and the amino acid at the position corresponding to position 172 in the amino acid sequence as shown in SEQ ID NO: 1 are substituted and having activity on a glycated substrate.

[11] The amadoriase according to [10], comprising an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, histidine, or lysine, and when aligned with the amino acid sequence as shown in SEQ ID NO: 1, the amino acid at the position corresponding to phenylalanine at position 172 in the amino acid sequence as shown in SEQ ID NO: 1 is glutamic acid or aspartic acid.

[12] The amadoriase according to [11], comprising an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, and when aligned with the amino acid sequence as shown in SEQ ID NO: 1, the amino acid at the position corresponding to phenylalanine at position 172 in the amino acid sequence as shown in SEQ ID NO: 1 is glutamic acid.

[13] The amadoriase according to any of [1] to [12], comprising an amino acid sequence in which, when aligned with the amino acid sequence as shown in SEQ ID NO: 1, the amino acid at the position corresponding to position 30 and the amino acid at the position corresponding to position 28 in the amino acid sequence as shown in SEQ ID NO: 1 are substituted and having activity on a glycated substrate.

[14] The amadoriase according to [13], comprising an amino acid sequence in which, when aligned with the amino acid sequence as shown in SEQ ID NO: 1, the amino acid at the position corresponding to serine at position 30 in the amino acid sequence as shown in SEQ ID NO: 1 is alanine, valine, leucine, or isoleucine, and when aligned with the amino acid sequence as shown in SEQ ID NO: 1, the amino acid at the position corresponding to valine at position 28 in the amino acid sequence as shown in SEQ ID NO: 1 is leucine, isoleucine, methionine, alanine, or cysteine.

[15] The amadoriase according to [14], comprising an amino acid sequence in which, when aligned with the amino acid sequence as shown in SEQ ID NO: 1, the amino acid at the position corresponding to serine at position 30 in the amino acid sequence as shown in SEQ ID NO: 1 is alanine, and when aligned with the amino acid sequence as shown in SEQ ID NO: 1, the amino acid at the position corresponding to valine at position 28 in the amino acid sequence as shown in SEQ ID NO: 1 is leucine.

[16] The amadoriase according to any of [1] to [15], comprising an amino acid sequence in which, when aligned with the amino acid sequence as shown in SEQ ID NO: 1, the amino acid at the position corresponding to position 12, the amino acid at the position corresponding to position 9, the amino acid at the position corresponding to position 13, the amino acid at the position corresponding to position 3, and the amino acid at the position corresponding to position 4 in the amino acid sequence as shown in SEQ ID NO: 1 are substituted and having activity on a glycated substrate.

[17] The amadoriase according to [16], comprising an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine, leucine, cysteine, or methionine;

when aligned with the amino acid sequence as shown in SEQ ID NO: 1, the amino acid at the position corresponding to arginine at position 9 in the amino acid sequence as shown in SEQ ID NO: 1 is threonine, serine, asparagine, or glutamine;

when aligned with the amino acid sequence as shown in SEQ ID NO: 1, the amino acid at the position corresponding to valine at position 13 in the amino acid sequence as shown in SEQ ID NO: 1 is isoleucine, leucine, cysteine, or methionine;

when aligned with the amino acid sequence as shown in SEQ ID NO: 1, the amino acid at the position corresponding to serine at position 3 in the amino acid sequence as shown in SEQ ID NO: 1 is threonine; and when aligned with the amino acid sequence as shown in SEQ ID NO: 1, the amino acid at the position corresponding to asparagine at position 4 in the amino acid sequence as shown in SEQ ID NO: 1 is proline.

[18] The amadoriase according to [17], comprising an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine;

when aligned with the amino acid sequence as shown in SEQ ID NO: 1, the amino acid at the position corresponding to arginine at position 9 in the amino acid sequence as shown in SEQ ID NO: 1 is threonine;

when aligned with the amino acid sequence as shown in SEQ ID NO: 1, the amino acid at the position corresponding to valine at position 13 in the amino acid sequence as shown in SEQ ID NO: 1 is isoleucine;

when aligned with the amino acid sequence as shown in SEQ ID NO: 1, the amino acid at the position corresponding to serine at position 3 in the amino acid sequence as shown in SEQ ID NO: 1 is threonine; and when aligned with the amino acid sequence as shown in SEQ ID NO: 1, the amino acid at the position corresponding to asparagine at position 4 in the amino acid sequence as shown in SEQ ID NO: 1 is proline.

[19] The amadoriase according to any of [1] to [18], further comprising an amino acid sequence in which, when aligned with the amino acid sequence as shown in SEQ ID NO: 1, the amino acid at the position corresponding to phenylalanine at position 286 in the amino acid sequence as shown in SEQ ID NO: 1 is tyrosine.

[20] The amadoriase according to any of [1] to [19], further comprising an amino acid sequence in which, when aligned with the amino acid sequence as shown in SEQ ID NO: 1, the amino acid at the position corresponding to glutamic acid at position 204 of the amino acid sequence as shown in SEQ ID NO: 1 is alanine;

when aligned with the amino acid sequence as shown in SEQ ID NO: 1, the amino acid at the position corresponding to aspartic acid at position 338 in the amino acid sequence as shown in SEQ ID NO: 1 is alanine;

when aligned with the amino acid sequence as shown in SEQ ID NO: 1, the amino acid at the position corresponding to glutamic acid at position 44 in the amino acid sequence as shown in SEQ ID NO: 1 is lysine;

when aligned with the amino acid sequence as shown in SEQ ID NO: 1, the amino acid at the position corresponding to glutamic acid at position 340 in the amino acid sequence as shown in SEQ ID NO: 1 is lysine; and when aligned with the amino acid sequence as shown in SEQ ID NO: 1, the amino acid at the position corresponding to aspartic acid at position 194 in the amino acid sequence as shown in SEQ ID NO: 1 is lysine or alanine.

[21] The amadoriase according to any of [1] to [20], wherein the surfactant is an anionic surfactant.

[22] The amadoriase according to any of [1] to [21], which is derived from the genus *Coniochaeta*, *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, *Penicillium*, *Fusarium*, *Achaetomiella*, *Achaetomium*, *Thielavia*, *Chaetomium*, *Gelasinospora*, *Microascus*, *Leptosphaeria*, *Ophiobolus*, *Pleospora*, *Coniochaetidium*, *Pichia*, *Debaryomyces*, *Corynebacterium*, *Agrobacterium*, or *Arthrobacter*.

[23] The amadoriase according to any of [1] to [21], comprising the amino acid sequence as shown in SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 94, or SEQ ID NO: 110 and having an amino acid substitution as defined in any of [1] to [20].

[24] An amadoriase gene encoding an amadoriase comprising the amino acid sequence according to any of [1] to [23].

[25] A method for producing an amadoriase comprising the following steps:

(i) culturing a host cell transduced with the gene according to [24];

(ii) expressing the amadoriase gene contained in the host cell; and (iii) isolating the amadoriase from a culture product.

[26] A composition for use in measuring glycated hemoglobin comprising the amadoriase according to any of [1] to [23].

[27] The composition according to [26], which comprises one or more anionic surfactants.

[28] The composition according to [27], wherein the surfactant has a critical micelle concentration of 130 mM or lower at 25° C.

[29] The composition according to [27] or [28], wherein the anionic surfactant is one or more anionic surfactant selected from the group consisting of the following compounds:

a sulfuric ester compound represented by Formula (I):

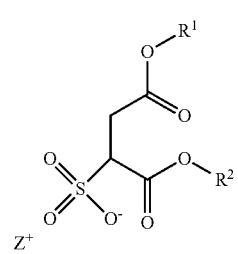

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a benzene sulfonic acid salt compound represented by Formula (II):

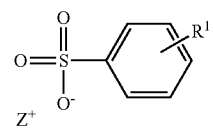

wherein $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

an acyl sarcosine acid salt compound represented by Formula (III):

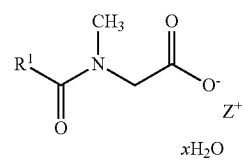

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a phosphonic acid salt compound represented by Formula (IV):

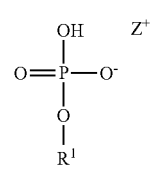

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a sulfosuccinic acid salt compound represented by Formula (V):

wherein, $R^1$ and $R^2$ each independently represent substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a carboxylic acid salt compound represented by Formula (VI):

$$R^1{-}COO^-Z^+ \qquad (VI)$$

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a sulfonic acid salt compound represented by Formula (VII):

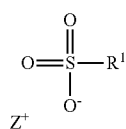

(VII)

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion; and cholic acid salt, deoxycholic acid salt, glycocholic acid salt, taurocholic acid salt, taurodeoxycholic acid salt, acylglutamic acid salt, acylmethyl alanine salt, acylglycine salt, acylmethyl taurine salt, and a derivative of any thereof.

[30] A method for measurement of glycated hemoglobin comprising use of the amadoriase according to any of [1] to [23].

[31] The composition according to [26], comprising sodium cholate or sodium deoxycholate.

[32] The composition according to [31], wherein the residual activity (%) of the amadoriase that was allowed to stand at 30° C. for 5 minutes after sodium cholate had been added to a final concentration of 0.5 to 1.5% (w/v) is 100% or more, compared with the case in which no sodium cholate had been added (100%), or the residual activity of the amadoriase that was allowed to stand at 30° C. for 5 minutes after sodium deoxycholate had been added to a final concentration of 0.3 to 2.0% (w/v) is 100% or more, compared with the case in which no sodium deoxycholate is added (100%).

[33] A composition for measurement of glycated hemoglobin comprising sodium cholate and an amadoriase.

[34] The composition according to [33], wherein the residual activity (%) of the amadoriase that was allowed to stand at 30° C. for 5 minutes after sodium cholate had been added to a final concentration of 0.5 to 1.5% (w/v) is 100% or more, compared with the case in which no sodium cholate had been added (100%).

This description includes part or all of the content as disclosed in the description and/or drawings of Japanese Patent Application No. 2014-227548, which is a priority document of the present application.

Effects of the Invention

The present invention can provide an amadoriase excellent in surfactant tolerance, which can advantageously be used as a diagnostic enzyme for diabetes and which can be used for a kit for measuring a diabetes marker, and a gene encoding such amadoriase and the like. Use of the amadoriase enables measurement of glycated hemoglobin even in the presence of a surfactant at a high concentration.

BRIEF DESCRIPTION OF DRAWINGS

FIGS. 1-1, 1-2, 1-3, 1-4, and 1-5 show amino acid sequences of the amadoriase derived from the genus *Coniochaeta* (SEQ ID NO: 1), the amadoriase derived from *Eupenicillium terrenum* (SEQ ID NO: 3), the ketoamine oxidase derived from *Pyrenochaeta* sp. (SEQ ID NO: 4), the ketoamine oxidase derived from *Arthrinium* sp. (SEQ ID NO: 5), the ketoamine oxidase derived from *Curvularia clavata* (SEQ ID NO: 6), the ketoamine oxidase derived from *Neocosmospora vasinfecta* (SEQ ID NO: 7), the fructosyl amino acid oxidase derived from *Cryptococcus neoformans* (SEQ ID NO: 8), the fructosyl peptide oxidase derived from *Phaeosphaeria nodorum* (SEQ ID NO: 9), the fructosyl amino acid oxidase derived from *Aspergillus nidulans* (SEQ ID NO: 10), the fructosyl peptide oxidase derived from *Emericella nidulans* (SEQ ID NO: 11), the fructosyl amino acid oxidase derived from *Ulocladium* sp. (SEQ ID NO: 12), and the fructosyl amino acid oxidase derived from *Penicillium janthinellum* (SEQ ID NO: 13).

EMBODIMENTS FOR CARRYING OUT THE INVENTION

The present invention is described in detail below.

The amadoriase according to the present invention can recognize a glycated protein or a glycated peptide as a substrate.

(Glycated Protein and Hemoglobin A1c)

The term "glycated protein" used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.

(Glycated Peptide and Fructosyl Peptide)

The term "glycated peptide" used herein refers to a non-enzymatically-glycated peptide derived from a glycated protein. Peptides that are directly and non-enzymatically glycated, products of degradation of glycated proteins by a protease or the like, and products of glycation of (poly) peptides constituting glycated proteins are included in glycated peptides. A "glycated peptide" is also referred to as a "fructosyl peptide." Regarding glycated proteins, examples of amino groups in the glycated peptide side chain include an amino terminal α-amino group and a ε-amino group in the lysine side chain within a peptide. However, in the present invention, the glycated peptide is, more specifically, an α-glycated peptide (α-fructosyl peptide). An α-glycated peptide is released and formed from a glycated protein having a glycated N-terminal α-amino acid by an arbitrary means, such as limited degradation with a protease or the like. Where the glycated protein of interest is hemoglobin A1c (HbA1c), for example, the α-glycated peptide is a glycated peptide cleaved from the HbA1c β-chain having the glycated N terminus. The HbA1c β-chain composed of 146 amino acids also falls under an α-glycated peptide (αF146P).

According to an embodiment of the present invention, the target substance (i.e., the substrate) to which the amadoriase of the present invention acts on is HbA1c and more specifically the β-chain of HbA1c. According to one embodiment, the target substance to which the amadoriase of the present invention acts on is α-glycated peptide cleaved from the β-chain of HbA1c, such as αFV to αF128P, αFV to αF64P, αFV to αF32P, or αFV to αF16P. More specifically, it is α-fructosyl-valyl-histidyl-leucyl-threonyl-proryl-glutamic acid (αF6P). According to a one embodiment, the target substance to which the amadoriase of the present invention acts on is αFVH (α-fructosyl-valyl-histidine) or αFV (α-fructosyl valine). The amadoriase according to the present invention is capable of reacting with one or more substrates described above. Such activities are collectively referred to as "activity on a glycated substrate" or "oxidation activity on a glycated substrate" herein, according to need.

(Amadoriase)

An amadoriase is also referred to as ketoamine oxidase, fructosyl amino acid oxidase, fructosyl peptide oxidase, or fructosyl amine oxidase. An amadoriase is an enzyme that catalyzes the reaction which oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

In one embodiment, the amadoriase of the present invention is a variant of an amadoriase having enhanced surfactant tolerance, which is prepared based on the amadoriase derived from the genus *Coniochaeta* having the amino acid sequence as shown in SEQ ID NO: 1.

In one embodiment, the amadoriase of the present invention is a variant of an amadoriase having enhanced surfactant tolerance, which is prepared based on ketoamine oxidase derived from *Curvularia clavata* (CcFX) having the amino acid sequence as shown in SEQ ID NO: 94.

In one embodiment, the amadoriase of the present invention is a variant of an amadoriase having enhanced surfactant tolerance, which is prepared based on glycated hexapeptide oxidase derived from *Emericella nidulans* (En42FX) having the amino acid sequence as shown in SEQ ID NO: 110.

Examples of such variants include an amadoriase comprising an amino acid sequence exhibiting a high degree of sequence identity with SEQ ID NO: 1, SEQ ID NO: 94, or SEQ ID NO: 110 (e.g., 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher) and an amadoriase comprising an amino acid sequence resulting from modification, variation, deletion, substitution, addition, and/or insertion of 1 or several amino acids in the amino acid sequence as shown in SEQ ID NO: 1.

The amadoriase according to the present invention may be prepared from an amadoriase derived from an organism species belonging to, for example, the genus *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, *Penicillium*, *Fusarium*, *Achaetomiella*, *Achaetomium*, *Thielavia*, *Chaetomium*, *Gelasinospora*, *Microascus*, *Leptosphaeria*, *Ophiobolus*, *Pleospora*, *Coniochaetidium*, *Pichia*, *Corynebacterium*, *Agrobacterium*, or *Arthrobacter*. In particular, an amadoriase having surfactant tolerance and/or comprising an amino acid sequence exhibiting a high degree of sequence identity with the sequence as shown in SEQ ID NO: 1 is preferable.

A variant of an amadoriase having modified anionic surfactant tolerance (a modified amadoriase) can be obtained by substitution, addition, or deletion of at least 1 amino acid residue in the amino acid sequence of the amadoriase.

Examples of amino acid substitutions for enhancing anionic surfactant tolerance include substitutions of amino acids at positions corresponding to the amino acids at the positions in the amino acid sequence as shown in SEQ ID NO: 1 described below. Such substitutions at the positions described below may be referred to as "amino acid substitutions that enhances tolerance of an amadoriase to an anionic surfactant" herein:

(a) substitution of the amino acid at the position corresponding to lysine at position 80 with, for example, arginine, asparagine, glutamine, or histidine;

(b) substitution of the amino acid at the position corresponding to methionine at position 71 with, for example, leucine, isoleucine, alanine, glycine, valine, or cysteine;

(c) substitution of the amino acid at the position corresponding to glutamic acid at position 175 with, for example, arginine, histidine, or lysine;

(d) substitution of the amino acid at the position corresponding to phenylalanine at position 172 with, for example, glutamic acid, aspartic acid, tyrosine, or glutamine;

(e) substitution of the amino acid at the position corresponding to valine at position 279 with, for example, isoleucine or cysteine;

(f) substitution of the amino acid at the position corresponding to valine at position 12 with, for example, isoleucine, leucine, cysteine, or methionine;

(g) substitution of the amino acid at the position corresponding to arginine at position 9 with, for example, threonine, serine, asparagine, or glutamine;

(h) substitution of the amino acid at the position corresponding to glutamine at position 77 with, for example, aspartic acid, glutamic acid, lysine, or asparagine;

(i) substitution of the amino acid at the position corresponding to serine at position 30 with, for example, alanine, threonine, valine, leucine, or isoleucine;

(j) substitution of the amino acid at the position corresponding to valine at position 28 with, for example, leucine, isoleucine, methionine, alanine, or cysteine;

(k) substitution of the amino acid at the position corresponding to valine at position 13 with, for example, isoleucine, leucine, cysteine, or methionine;

(l) substitution of the amino acid at the position corresponding to serine at position 3 with, for example, threonine;

(m) substitution of the amino acid at the position corresponding to asparagine at position 4 with, for example, proline;

(n) substitution of the amino acid at the position corresponding to phenylalanine at position 286 with, for example, tyrosine or tryptophan;

(o) substitution of the amino acid at the position corresponding to glutamic acid at position 204 with, for example, alanine, leucine, isoleucine, valine, or cysteine;

(p) substitution of the amino acid at the position corresponding to aspartic acid at position 338 with, for example, alanine, leucine, isoleucine, valine, or cysteine;

(q) substitution of the amino acid at the position corresponding to glutamic acid at position 44 with, for example, lysine, arginine, or histidine;

(r) substitution of the amino acid at the position corresponding to glutamic acid at position 340 with, for example, lysine, arginine, or histidine; and (s) substitution of the amino acid at the position corresponding to aspartic acid at position 194 with, for example, lysine, arginine, histidine, alanine, leucine, isoleucine, valine, or cysteine.

An amadoriase variant having enhanced surfactant tolerance may comprise at least 1 or a plurality of the amino acid substitutions described above. For example, such variant may comprise 1, 2, 3, 4, 5, 6, 7, 8, 9, 10, 11, 12, 13, 14, 15, 16, 17, 18, or 19 of the amino acid substitutions above.

In particular, variants comprising amino acid substitutions at positions corresponding to the amino acid positions in the amino acid sequence as shown in SEQ ID NO: 1 described below are preferable.

71/80 variation, which results in a variant comprising substitution of the amino acid at the position corresponding to lysine at position 80 with, for example, arginine, asparagine, glutamine, or histidine and substitution of the amino acid at the position corresponding to methionine at position 71 with, for example, leucine, isoleucine, alanine, glycine, valine, or cysteine. In this description, the combination of the variations above may be referred to as "71/80 variation (mutation) (substitution)" and a variant (mutant) comprising the same may be referred to as a "71/80 variant (mutant)." Examples of 71/80 variants include the 71L/80R variant, the 71L/K80N variant, the 71A/K80R variant, and the 71A/K80N variant.

71/77/80 variation, which results in a variant comprising substitution of the amino acid at the position corresponding to lysine at position 80 with, for example, arginine, asparagine, glutamine, or histidine, substitution of the amino acid at the position corresponding to methionine at position 71 with, for example, leucine, isoleucine, alanine, glycine, valine, or cysteine, and substitution of the amino acid at the position corresponding to glutamine at position 77 with, for example, aspartic acid, glutamic acid, lysine, or asparagine. In this description, the combination of the variations above may be referred to as "71/77/80 variation" and a variant comprising the same may be referred to as a "71/77/80 variant." Examples of 71/77/80 variants include the 71L/77D/80R variant, the 71L/77D/K80N variant, the 71A/77D/K80R variant, and the 71A/77D/K80N variant.

172/175 variation, which results in a variant comprising substitution of the amino acid at the position corresponding to phenylalanine at position 172 with, for example, glutamic acid or aspartic acid and substitution of the amino acid at the position corresponding to glutamic acid at position 175 with, for example, arginine, histidine, or lysine. In this description, the combination of the variations above may be referred to as "172/175 variation" and a variant comprising the same may be referred to as a "172/175 variant." An example of the 172/175 variant is the 172E/175R variant.

28/30 variation, which results in a variant comprising substitution of the amino acid at the position corresponding to serine at position 30 with, for example, alanine, threonine, valine, leucine, or isoleucine and substitution of the amino acid at the position corresponding to valine at position 28 with, for example, leucine, isoleucine, methionine, alanine, or cysteine. In this description, the combination of the variations above may be referred to as "28/30 variation" and a variant comprising the same may be referred to as a "28/30 variant." An example of a 28/30 variant is the 28L/30A variant.

3/4/9/12/13 variation, which results in a variant comprising substitution of the amino acid at the position corresponding to valine at position 12 with, for example, isoleucine, leucine, cysteine, or methionine, substitution of the amino acid at the position corresponding to arginine at position 9 with, for example, threonine, serine, asparagine, or glutamine, substitution of the amino acid at the position corresponding to valine at position 13 with, for example, isoleucine, leucine, cysteine, or methionine, substitution of the amino acid at the position corresponding to serine at position 3 with, for example, threonine, and substitution of the amino acid at the position corresponding to asparagine at position 4 with, for example, proline. In this description, the combination of the variations above may be referred to as "3/4/9/12/13 variation" and a variant comprising the same may be referred to as a "3/4/9/12/13 variant." An example of a 3/4/9/12/13 variant is the 3T/4P/9T/12I/13I variant.

The combinations of variations described above can be employed in combination. For example, variants as described below are preferable.

28/30/172/175 variation, which is a combination of the 28/30 variation and the 172/175 variation. In this description, the combination of the variations above may be referred to as "28/30/172/175 variation" and a variant comprising the same may be referred to as a "28/30/172/175 variant." An example of a 28/30/172/175 variant is the 28L/30A/172E/175R variant.

28/30/71/80 variation, which is a combination of the 28/30 variation and the 71/80 variation. A variant comprising the same may be referred to as the "28/30/71/80 variant." Examples of 28/30/71/80 variants include the 28L/30A/71L/80R variant, the 28L/30A/71L/K80N variant, the 28L/30A/71A/K80R variant, and the 28L/30A/71A/K80N variant.

28/30/71/77/80 variation: which is a combination of the 28/30 variation and the 71/77/80 variation. A variant comprising the same may be referred to as the "28/30/71/77/80 variant." Examples of 28/30/71/77/80 variants include the 28L/30A/71L/77D/80R variant, 28L/30A/71L/77D/K80N variant, the 28L/30A/71A/77D/K80R variant, and the 28L/30A/71A/77D/K80N variant.

71/80/172/175 variation, which is a combination of the 71/80 variation and the 172/175 variation. A variant comprising the same may be referred to as the "71/80/172/175 variant." Examples of 71/80/172/175 variants include the 71L/80R/172E/175R variant, the 71L/K80N/172E/175R variant, the 71A/K80R/172E/175R variant, and the 71A/K80N/172E/175R variant.

71/77/80/172/175 variation, which is a combination of the 71/77/80 variation and the 172/175 variation. A variant comprising the same may be referred to as the "71/77/80/172/175 variant." Examples of 71/77/80/172/175 variants include the 71L/77D/80R/172E/175R variant, the 71L/77D/K80N/172E/175R variant, the 71A/77D/K80R/172E/175R variant, and the 71A/77D/K80N/172E/175R variant.

28/30/71/80/172/175 variation, which is a combination of the 28/30 variation, the 71/80 variation, and the 172/175 variation. In this description, the combination of the variations above may be referred to as "28/30/71/80/172/175 variation" and a variant comprising the same may be referred to as a "28/30/71/80/172/175 variant." Examples of 28/30/71/80/172/175 variants include the 28L/30A/71L/80R/172E/175R variant, the 28L/30A/71L/80N/172E/175R variant, the 28L/30A/71A/80R/172E/175R variant, and the 28L/30A/71A/80N/172E/175R variant.

28/30/71/77/80/172/175 variation, which is a combination of the 28/30 variation, the 71/77/80 variation, and the 172/175 variation. In this description, the combination of the variations above may be referred to as "28/30/71/77/80/172/175 variation" and a variant comprising the same may be referred to as a "28/30/71/77/80/172/175 variant." Examples of 28/30/71/77/80/172/175 variants include the 28L/30A/71L/77D/80R/172E/175R variant, the 28L/30A/71L/77D/80N/172E/175R variant, the 28L/30A/71A/77D/80R/172E/175R variant, and the 28L/30A/71A/77D/80N/172E/175R variant.

3/4/9/12/13/28/30/71/77/80/172/175 variation, which is a combination of the 3/4/9/12/13 variation, the 28/30 variation, the 71/77/80 variation, and the 172/175 variation. In this description, the combination of the variations above may be referred to as "3/4/9/12/13/28/30/71/77/80/172/175 variation" and a variant comprising the same may be referred to as a "3/4/9/12/13/28/30/71/77/80/172/175 variant." Examples of 3/4/9/12/13/28/30/71/77/80/172/175 variants include the 3T/4P/9T/12I/13I/28L/30A/71L/77D/80R/172E/175R variant, the 3T/4P/9T/12I/13I/28L/30A/71L/77D/80N/172E/175R variant, the 3T/4P/9T/12I/13I/28L/30A/71A/77D/80R/172E/175R variant, and the 3T/4P/9T/12I/13I/28L/30A/71A/77D/80N/172E/175R variant.

3/4/9/12/13/28/30/71/77/80/172/175/286 variation, which is a combination of the 3/4/9/12/13 variation, the 28/30 variation, the 71/77/80 variation, the 172/175 variation, and the 286 variation. A variant comprising the same may be referred to as the "3/4/9/12/13/28/30/71/77/80/172/175/286 variant." Examples of 3/4/9/12/13/28/30/71/77/80/172/175/286 variants include the 3T/4P/9T/12I/13I/28L/30A/71L/77D/80R/172E/175R/286Y variant, the 3T/4P/9T/12I/13I/28L/30A/71L/77D/80N/172E/175R/286Y variant, the 3T/4P/9T/12I/13I/28L/30A/71A/77D/80R/172E/175R/286Y variant, and the 3T/4P/9T/12I/13I/28L/30A/71A/77D/80N/172E/175R/286Y variant.

The amadoriase variant according to the present invention that is excellent in surfactant tolerance may comprise an amino acid substitution for enhancing the surfactant tolerance in the amino acid sequence as shown in SEQ ID NO: 1, SEQ ID NO: 94, or SEQ ID NO: 110. Further, the surfactant-tolerant amadoriase variant according to the present invention may comprise deletion, insertion, addition, and/or substitution of one or several amino acids (e.g., 1 to 15, 1 to 10, preferably 1 to 5, further preferably 1 to 3, and particularly preferably 1 amino acid) at a position (or positions) other than the positions of the amino acid substitutions described above. Furthermore, the present invention encompasses an amadoriase variant comprising the amino acid substitution for enhancing surfactant tolerance or the amino acid substitution for improving properties other than surfactant tolerance, such as substrate specificity, said variant having an amino acid sequence identity of 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher to a region in the amino acid sequence as shown in SEQ ID NO: 1, 3, 94, or 110 other than the amino acid substitutions described above, having an amadoriase activity, and having modified surfactant tolerance.

An amadoriase having the amino acid sequence as shown in SEQ ID NO: 1 is an amadoriase (CFP-T7) derived from the genus *Coniochaeta* produced by *E. coli* carrying a recombinant plasmid referred to as "pKK223-3-CFP-T7" in WO 2007/125779 (Accession Number: FERM BP-10593), which is a modified amadoriase with excellent heat stability previously discovered by the present inventors. CFP-T7 is a triple variant obtained by successively introducing artificial variations into positions 272, 302, and 388 of a naturally-occurring amadoriase derived from the genus *Coniochaeta*.

Concerning the amino acid substitutions described above, an amino acid position indicates a position in the amino acid sequence of the amadoriase derived from the genus *Coniochaeta* as shown in SEQ ID NO: 1. However, in the case of amino acid sequences of amadoriases derived from other organism species, the amino acid at the position corresponding to the position in the amino acid sequence as shown in SEQ ID NO: 1 is substituted. The meaning of the expression "a position corresponding to . . . " is described elsewhere.

(Additional Substitution)
(Amino Acid Substitution that Alters Substrate Specificity of Amadoriase)

Previously, the present inventors reported that substrate specificity of an amadoriase can be altered through substitution of amino acid residues thereof (see, for example, WO 2013/162035, incorporated herein by reference in its entirety). The amadoriase according to the present invention may optionally further comprise such amino acid substitution.

Examples of amino acid substitutions that alter substrate specificity of an amadoriase include substitutions of amino acids at positions corresponding to the amino acids at the positions in the amino acid sequence as shown in SEQ ID NO: 1 described below:

(a) arginine at position 62;
(b) leucine at position 63;
(c) glutamic acid at position 102;
(d) aspartic acid at position 106;
(e) glutamine at position 110;
(f) alanine at position 113;
(g) alanine at position 355;
(h) alanine at position 419;
(i) aspartic acid at position 68; and
(j) alanine at position 356.

Optionally, the amino acid at a position corresponding to arginine at position 62 may be substituted with alanine, aspartic acid, asparagine, glutamine, glutamic acid, glycine, valine, leucine, isoleucine, cysteine, serine, threonine, or proline. Optionally, the amino acid at a position corresponding to (b) leucine at position 63 may be substituted with histidine or alanine. Optionally, the amino acid at a position corresponding to (c) glutamic acid at position 102 may be substituted with lysine. Optionally, the amino acid at a position corresponding to (d) aspartic acid at position 106 may be substituted with alanine, lysine, or arginine. Optionally, the amino acid at a position corresponding to (e) glutamine at position 110 may be substituted with leucine or tyrosine. Optionally, the amino acid at a position corresponding to (f) alanine at position 113 may be substituted with lysine or arginine. Optionally, the amino acid at a position corresponding to (g) alanine at position 355 may be substituted with serine. Optionally, the amino acid at a position corresponding to (h) alanine at position 419 may be substituted with lysine. Optionally, the amino acid at a position corresponding to (i) aspartic acid at position 68 may be substituted with asparagine. Optionally, the amino acid at a position corresponding to (j) alanine at position 356 may be substituted with threonine.

In this description, substitutions at such positions (i.e., positions 62, 63, 68, 102, 106, 110, 113, 355, 419, are 356) may be referred to as "amino acid substitutions that alter substrate specificity of an amadoriase."

(Amino Acid Substitution that Enhances Cationic Surfactant Tolerance of Amadoriase)

The present inventors confirmed that cationic surfactant tolerance of an amadoriase could be enhanced through substitution of amino acid residues thereof (see, for example, JP Patent Application No. 2013-221515 and PCT/JP2014/071036, incorporated herein by reference in their entirety).

Examples of amino acid substitutions that enhance cationic surfactant tolerance of an amadoriase include substitutions of amino acids at positions corresponding to the amino acids at the positions in the amino acid sequence as shown in SEQ ID NO: 1 described below:

(i) asparagine at position 262;
(ii) valine at position 257;
(iii) glutamic acid at position 249;
(iv) glutamic acid at position 253;
(v) glutamine at position 337;
(vi) glutamic acid at position 340;
(vii) aspartic acid at position 232;
(viii) aspartic acid at position 129;
(ix) aspartic acid at position 132;
(x) glutamic acid at position 133;
(xi) glutamic acid at position 44;
(xii) glycine at position 256;
(xiii) glutamic acid at position 231; and
(xiv) glutamic acid at position 81.

Optionally, the amino acid at a position corresponding to asparagine at position 262 may be substituted with histidine. Optionally, the amino acid at a position corresponding to valine at position 257 may be substituted with cysteine, serine, or threonine. Optionally, the amino acid at a position corresponding to glutamic acid at position 249 may be substituted with lysine or arginine. Optionally, the amino acid at a position corresponding to glutamic acid at position 253 may be substituted with lysine or arginine. Optionally, the amino acid at a position corresponding to glutamine at position 337 may be substituted with lysine or arginine. Optionally, the amino acid at a position corresponding to glutamic acid at position 340 may be substituted with proline. Optionally, the amino acid at a position corresponding to aspartic acid at position 232 may be substituted with lysine or arginine. Optionally, the amino acid at a position corresponding to aspartic acid at position 129 may be substituted with lysine or arginine. Optionally, the amino acid at a position corresponding to aspartic acid at position 132 may be substituted with lysine or arginine. Optionally, the amino acid at a position corresponding to glutamic acid at position 133 may be substituted with alanine, methionine, lysine, or arginine. Optionally, the amino acid at a position corresponding to glutamic acid at position 44 may be substituted with proline. Optionally, the amino acid at a position corresponding to glycine at position 256 may be substituted with lysine or arginine. Optionally, the amino acid at a position corresponding to glutamic acid at position 231 may be substituted with lysine or arginine. Optionally, the amino acid at a position corresponding to glutamic acid at position 81 may be substituted with lysine or arginine.

In this description, substitutions at such positions (i.e., 262, 257, 249, 253, 337, 340, 232, 129, 132, 133, 44, 256, 231, and 81) may be referred to as "amino acid substitutions that improve cationic surfactant tolerance of an amadoriase. In particular, substitution of position 44 with proline and substitution of position 340 with proline are amino acid substitutions that improve cationic surfactant tolerance.

(Substitution that Enhances Dehydrogenase Activity/Lowers Oxidase Activity of Amadoriase)

The present inventors confirmed that dehydrogenase activity of an amadoriase could be enhanced and/or oxidase activity thereof could be lowered through substitution of amino acid residues thereof (see, for example, JP Patent Application No. 2014-217405, incorporated herein by reference in its entirety).

Examples of amino acid substitutions for enhancing dehydrogenase activity and/or lowering oxidase activity of an amadoriase include substitutions of amino acids at positions corresponding to the amino acids at the positions in the amino acid sequence as shown in SEQ ID NO: 1 described below:

(1) substitution of cysteine at position 280 with, for example, a polar amino acid selected from the group consisting of glutamine, serine, threonine, and asparagine, a charged amino acid selected from the group consisting of aspartic acid, glutamic acid, lysine, arginine, and histidine, or an amino acid selected from the group consisting of methionine, proline, phenylalanine, tyrosine, and tryptophan;

(2) substitution of phenylalanine at position 267 with, for example, tyrosine;

(3) substitution of phenylalanine at position 269 with, for example, tyrosine;

(4) substitution of aspartic acid at position 54 with, for example, asparagine, alanine, glutamine, histidine, glycine, or valine; and (5) substitution of tyrosine at position 241 with, for example, glutamine, lysine, glutamic acid, asparagine, aspartic acid, arginine, or histidine.

In this description, substitutions at such positions (i.e., positions 280, 267, 269, 54, and 241) may be referred to as "amino acid substitutions that enhance dehydrogenase activity and/or lower oxidase activity of an amadoriase.

(Amino Acid Deletion Capable of Improving Heat Stability of the Amadoriase)

Previously, the present inventors reported that heat stability of an amadoriase can be improved by deletion of 3 amino acid residues from its carboxyl terminus (see WO 2013/100006, incorporated herein by reference in its entirety). In one embodiment, the amadoriase of the present invention may comprise a deletion of 3 amino acid residues from the carboxyl terminus thereof, in addition to the substitution described above. The term "deletion of 3 amino acid residues from the carboxyl terminus" used herein may be referred to as a deletion capable of improving heat stability.

Previously, the present inventors also confirmed that heat stability of an amadoriase can be improved by substitution of amino acid residues thereof (see WO 2013/100006). In one embodiment, the amadoriase of the present invention may further comprise amino acid substitution capable of improving heat stability of an amadoriase, in addition to the substitution(s) described above.

Examples of amino acid substitutions capable of improving heat stability of an amadoriase include amino acid substitutions at positions corresponding to the amino acids at the positions in the amino acid sequence as shown in SEQ ID NO: 1 described below:

(b) alanine at position 151;
(c) phenylalanine at position 43;

(d) histidine at position 53;
(e) phenylalanine at position 267;
(f) threonine at position 350;
(g) alanine at position 185;
(h) glutamic acid at position 196;
(i) serine at position 299; and
(j) valine at position 323.

Optionally, the amino acid at a position corresponding to alanine at position 151 may be substituted with cysteine. Optionally, the amino acid at a position corresponding to phenylalanine at position 43 may be substituted with tyrosine. Optionally, the amino acid at a position corresponding to histidine at position 53 may be substituted with asparagine or tyrosine. Optionally, the amino acid at a position corresponding to phenylalanine at position 267 may be substituted with tyrosine. Optionally, the amino acid at a position corresponding to threonine at position 350 may be substituted with alanine. Optionally, the amino acid at a position corresponding to alanine at position 185 may be substituted with serine. Optionally, the amino acid at a position corresponding to glutamic acid at position 196 may be substituted with aspartic acid. Optionally, the amino acid at a position corresponding to serine at position 299 may be substituted with threonine. Optionally, the amino acid at a position corresponding to valine at position 323 may be substituted with glutamic acid.

In the present disclosure, substitutions at such positions (i.e., positions 151, 43, 53, 267, 350, 185, 196, 299, and 323) may be referred to as "amino acid substitutions that improve heat stability of an amadoriase.

(Obtaining a Gene Encoding an Amadoriase)

In order to obtain a gene encoding an amadoriase according to the present invention described above (hereinafter, also merely referred to as "amadoriase genes"), widely used gene cloning methods can be used. For example, chromosomal DNA or mRNA can be extracted from a microorganism fungus body or various cells having the ability to produce an amadoriase by conventional techniques, such as the method described in "Current Protocols in Molecular Biology" (WILEY Interscience, 1989). In addition, cDNA can be synthesized using mRNA as the template. A chromosomal DNA or cDNA library can be constructed using the chromosomal DNA or cDNA obtained in such a manner.

Subsequently, DNA including the entire sequence of a target amadoriase gene can be obtained by a method of synthesizing an appropriate probe DNA based on the amino acid sequence of the amadoriase mentioned above and selecting an amadoriase gene from a chromosomal DNA or cDNA library using the probe DNA. Alternatively, an appropriate primer DNA may be designed based on the amino acid sequence mentioned above, a DNA including the target gene fragment encoding the amadoriase gene may be amplified by using an appropriate polymerase chain reaction (PCR) technique, such as the 5' RACE or 3' RACE method, and the resulting DNA fragments may then be linked to obtain DNA comprising the entire length of the amadoriase gene of interest.

A preferable example of a gene encoding an amadoriase thus obtained includes an amadoriase gene derived from the genus *Coniochaeta* (JP 2003-235585 A).

The amadoriase genes are preferably linked to various vectors using conventional techniques from the perspective of handling. Examples include the recombinant plasmid pKK223-3-CFP (JP 2003-235585 A) prepared by inserting DNA encoding the amadoriase gene derived from the *Coniochaeta* sp. NISL 9330 strain into the pKK223-3 vector (GE Healthcare).

(Vector)

Vectors that can be used in the present invention are not limited to the plasmid vectors above. For example, any other vector known in the art, such as bacteriophage or cosmid vectors, can be used. In particular, for example, pBluescriptII SK+ (manufactured by Stratagene Corporation) is preferable.

(Mutation of Amadoriase Gene)

Mutation of an amadoriase gene can be performed by any known method depending on the intended form of mutation. More specifically, methods of bringing a chemical mutagen into contact with and allowing to act on an amadoriase gene or recombinant DNA comprising such gene integrated therein, ultraviolet irradiation methods, genetic engineering techniques, methods making extensive use of protein engineering techniques, or various other methods can be extensively used.

Examples of chemical mutagens used in the aforementioned variation include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the drug mentioned above at concentrations of from 0.5 M to 12 M. The ultraviolet irradiation may also be performed according to conventional techniques as described above (Gendai Kagaku, pp. 24-30, June, 1989).

As the method making extensive use of protein engineering techniques a technique known as site-specific mutagenesis can, in general, be used. Examples include the Kramer method (Nucleic Acids Res., 12, 9441, 1984; Methods Enzymol., 154, 350, 1987; and Gene, 37, 73, 1985), the Eckstein method (Nucleic Acids Res., 13, 8749, 1985; Nucleic Acids Res., 13, 8765, 1985; and Nucleic Acids Res, 14, 9679, 1986), and the Kunkel method (Proc. Natl. Acid. Sci. U.S.A., 82, 488, 1985; and Methods Enzymol., 154, 367, 1987). Examples of a specific method of conversion of a nucleotide sequence in DNA include the use of a commercially available kit (Transformer Mutagenesis Kit, Clonetech; EXOIII/Mung Bean Deletion Kit, Stratagene; or Quick Change Site Directed Mutagenesis Kit, Stratagene).

The technique known as the general polymerization chain reaction (PCR) technique can also be used (Technique, 1, 11, 1989). In addition to the conventional genetic mutation techniques above, the modified amadoriase genes of interest can also be directly synthesized by an organic synthesis method or enzyme synthesis method.

The nucleotide sequences of DNA encoding the amadoriase genes obtained by the methods mentioned above may be determined or verified by, for example, using a multi-capillary DNA analysis system, CEQ2000 (Beckman Coulter Inc.).

(Transformation/Transduction)

The amadoriase genes obtained as described above may be integrated into a vector such as a bacteriophage vector, a cosmid vector, or a plasmid vector used in transformation of a procaryotic or eucaryotic cell by a conventional technique, and a host corresponding to each vector can be transformed or transduced by conventional techniques. For example, a host of interest, such as a microorganism belonging to the genus *Escherichia*, which specifically may be a strain of *E. coli* K-12, preferably a strain of *E. coli* JM109, *E. coli* DH5α

(manufactured by Takara Bio Inc.), a strain of *E. coli* B, or preferably a strain of *E. coli* BL21 (manufactured by NIPPON GENE CO., LTD.) may be transformed using the obtained recombinant DNA, or such recombinant DNA may be transduced into the host cells, so as to obtain the resulting strain.

(Amino Acid Sequence Identity or Similarity)

The amino acid sequence identity or similarity can be computed by a program such as maximum matching or search homology of GENETYX Ver. 11 (manufactured by GENETYX) or a program such as maximum matching or multiple alignment of DNASIS Pro (manufactured by Hitachi Solutions, Ltd.). In order to compute amino acid sequence identity, two or more amadoriases may be aligned, and the positions of identical amino acids in such two or more amadoriases may be determined. The identical regions in amino acid sequences can be determined based on such information.

Further, positions having similar amino acids in two or more amadoriases may be examined. For example, a plurality of amino acid sequences can be subjected to alignment using CLUSTALW and, in such case, Blosum62 can be used as the algorithm and a plurality of amino acid sequences can be subjected to alignment and amino acids determined to be similar as a result of such alignment may be referred to as "similar amino acids." In the variant of the present invention, amino acid substitution can be carried out between such similar amino acids. By carrying out such alignments, it is possible to examine regions having identical amino acid sequences and positions being occupied by similar amino acids regarding a plurality of amino acid sequences. Based on such information, homologous regions (conserved regions) in the amino acid sequences can be determined.

The term "homologous region(s)" used herein refers to region(s) consisting of identical or similar amino acids at corresponding positions in the reference amadoriase and in the comparative amadoriase, when two or more amadoriases are aligned, wherein said region(s) consist(s) of 3 or more, 4 or more, 5 or more, 6 or more, 7 or more, 8 or more, 9 or more, or 10 or more continuous amino acids. For example, FIG. 1 shows the alignment of amadoriases exhibiting 74% or higher sequence identity over the full-length amino acid sequences. In such sequences, the region of positions 10 to 32 with reference to the sequence of the amadoriase derived from *Coniochaeta* sp. as shown in SEQ ID NO: 1 consists of identical or similar amino acids, and, therefore, such region falls under a homologous region. Similarly, regions of positions 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be (can fall under) homologous regions.

Preferably, the homologous region of an amadoriase is the region consisting of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of an amadoriase is the region consisting of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1, SEQ ID NO: 94, or SEQ ID NO: 110, the sequence identity is, for example, 50% or higher, 60% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher, and such amadoriase variant has tolerance to anionic surfactants. In addition, the amino acid sequence in the homologous region of the amadoriase variant according to the present invention exhibits, for example, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher sequence identity with the amino acid sequence in the homologous region of SEQ ID NO: 1. FIG. 1 shows alignments of amadoriases exhibiting sequence identity of 74% or higher over the full length. With reference to the amadoriase derived from *Coniochaeta* sp. as shown in SEQ ID NO: 1, however, amino acid sequence identity is 90% or higher in homologous regions with other amadoriases shown in FIG. 1.

(Identification of Positions Corresponding to Amino Acids)

The phrase "position corresponding to the amino acid" refers to the position in an amino acid sequence of an amadoriase derived from another organism species that corresponds to the amino acid at a particular position in the amino acid sequence of an amadoriase derived from the genus *Coniochaeta* as shown in SEQ ID NO: 1.

As an exemplary method of identifying the "position corresponding to the amino acid", amino acid sequences may be compared using a known algorithm such as the Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Homologous positions are considered to exist in the same positions in the three-dimensional structures, and amino acid residues at such homologous positions are expected to exert similar effects in terms of specificity specific function of the amadoriase of interest.

FIG. 1 shows sequences of amadoriases derived from various types of known organism species. The amino acid sequence as shown in SEQ ID NO: 1 is shown on the uppermost line. Various sequences shown in FIG. 1 each have 70% or higher sequence identity with the sequence as shown in SEQ ID NO: 1 and these sequences are aligned in accordance using a known algorithm. The sites of variations in the variants according to the present invention are shown in the figure. Based on FIG. 1, the sites of variations in the amino acid sequence of the amadoriase derived from other organism species corresponding to the amino acid at the particular position in the amino acid sequence of the amadoriase derived from the genus *Coniochaeta* can be identified. FIG. 1 shows amino acid sequences of the amadoriase derived from the genus *Coniochaeta* (SEQ ID NO: 1), the amadoriase derived from *Eupenicillium terrenum* (SEQ ID NO: 3), the ketoamine oxidase derived from *Pyrenochaeta* sp. (SEQ ID NO: 4), the ketoamine oxidase derived from *Arthrinium* sp. (SEQ ID NO: 5), the ketoamine oxidase derived from *Curvularia clavata* (SEQ ID NO: 6), the ketoamine oxidase derived from *Neocosmospora vasinfecta* (SEQ ID NO: 7), the fructosyl amino acid oxidase derived from *Cryptococcus neoformans* (SEQ ID NO: 8), the fructosyl peptide oxidase derived from *Phaeosphaeria nodorum* (SEQ ID NO: 9), the fructosyl amino acid oxidase derived from *Aspergillus nidulans* (SEQ ID NO: 10), the fructosyl peptide oxidase derived from *Emericella nidulans* (SEQ ID NO: 11), the fructosyl amino acid oxidase derived from *Ulocladium* sp. (SEQ ID NO: 12), and the fructosyl amino acid oxidase derived from *Penicillium janthinellum* (SEQ ID NO: 13).

(Corresponding Positions of Sites of Substitutions)
(Corresponding Positions of Variations for Improvement in Anionic Surfactant Tolerance of the Present Invention)

In the present invention, the amino acid at "the position corresponding to lysine at position 80 in the amino acid sequence as shown in SEQ ID NO: 1" is the amino acid corresponding to lysine at position 80 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid residue of interest can be identified based on FIG. 1 showing the amino acid sequences aligned using the method for identifying an "amino acid at a position corresponding (or equivalent) to (the amino acid of interest)" described above.

Specifically, the amino acid at "the position corresponding to lysine at position 80 in the amino acid sequence as shown in SEQ ID NO: 1" is glutamine at position 80 in the case of the amadoriase derived from *Eupenicillium terrenum*, arginine at position 80 in the case of the ketoamine oxidase derived from *Pyrenochaeta* sp., cysteine at position 80 in the case of the ketoamine oxidase derived from *Arthrinium* sp., arginine at position 80 in the case of the ketoamine oxidase derived from *Curvularia clavata*, arginine at position 80 in the case of the ketoamine oxidase derived from *Neocosmospora vasinfecta*, arginine at position 80 in the case of the fructosyl amino acid oxidase derived from *Cryptococcus neoformans*, asparagine at position 80 in the case of the fructosyl peptide oxidase derived from *Phaeosphaeria nodorum*, lysine at position 79 in the case of the fructosyl amino acid oxidase derived from *Aspergillus nidulans*, lysine at position 79 in the case of the fructosyl peptide oxidase derived from *Emericella nidulans*, threonine at position 80 in the case of the fructosyl amino acid oxidase derived from *Ulocladium* sp., and lysine at position 80 in the case of the fructosyl amino acid oxidase derived from *Penicillium janthinellum*.

In the present invention, an amino acid at the "position corresponding to methionine at position 71 in the amino acid sequence as shown in SEQ ID NO: 1" is the amino acid corresponding to methionine at position 71 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to methionine at position 71 in the amino acid sequence as shown in SEQ ID NO: 1" is leucine at position 71 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, and it is leucine at position 70 in the case of the fructosyl amino acid oxidase derived from *Aspergillus nidulans* and the fructosyl peptide oxidase derived from *Emericella nidulans*.

In the present invention, the "position corresponding to glutamic acid at position 175 in the amino acid sequence as shown in SEQ ID NO: 1" is the position corresponding to glutamic acid at position 175 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 175 in the amino acid sequence as shown in SEQ ID NO: 1" is aspartic acid at position 175 in the case of the amadoriase derived from *Eupenicillium terrenum*, lysine at position 175 in the case of the ketoamine oxidase derived from *Pyrenochaeta* sp., arginine at position 175 in the case of the ketoamine oxidase derived from *Arthrinium* sp., alanine at position 175 in the case of the ketoamine oxidase derived from *Curvularia clavata*, arginine at position 175 in the case of the ketoamine oxidase derived from *Neocosmospora vasinfecta*, glutamic acid at position 175 in the case of the fructosyl amino acid oxidase derived from *Cryptococcus neoformans*, aspartic acid at position 173 in the case of the fructosyl peptide oxidase derived from *Phaeosphaeria nodorum*, glutamic acid at position 174 in the case of the fructosyl amino acid oxidase derived from *Aspergillus nidulans*, glutamic acid at position 174 in the case of the fructosyl peptide oxidase derived from *Emericella nidulans*, aspartic acid at position 175 in the case of the fructosyl amino acid oxidase derived from *Ulocladium* sp., and serine at position 175 in the case of the fructosyl amino acid oxidase derived from *Penicillium janthinellum*.

In the present invention, the "position corresponding to phenylalanine at position 172 in the amino acid sequence as shown in SEQ ID NO: 1" is the position corresponding to phenylalanine at position 172 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to phenylalanine at position 172 in the amino acid sequence as shown in SEQ ID NO: 1" is phenylalanine at position 172 in the case of the amadoriase derived from *Eupenicillium terrenum*, tyrosine at position 172 in the case of the ketoamine oxidase derived from *Pyrenochaeta* sp., glutamic acid at position 172 in the case of the ketoamine oxidase derived from *Arthrinium* sp., tyrosine at position 172 in the case of the ketoamine oxidase derived from *Curvularia clavata*, glutamic acid at position 172 in the case of the ketoamine oxidase derived from *Neocosmospora vasinfecta*, valine at position 172 in the case of the fructosyl amino acid oxidase derived from *Cryptococcus neoformans*, tyrosine at position 170 in the case of the fructosyl peptide oxidase derived from *Phaeosphaeria nodorum*, phenylalanine at position 171 in the case of the fructosyl amino acid oxidase derived from *Aspergillus nidulans*, phenylalanine at position 171 in the case of the fructosyl peptide oxidase derived from *Emericella nidulans*, phenylalanine at position 172 in the case of the fructosyl amino acid oxidase derived from *Ulocladium* sp., and phenylalanine at position 172 in the case of the fructosyl amino acid oxidase derived from *Penicillium janthinellum*.

In the present invention, the "position corresponding to valine at position 279 in the amino acid sequence as shown in SEQ ID NO: 1" is the position corresponding to valine at position 279 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 279 in the amino acid sequence as shown in SEQ ID NO: 1" is valine at position 279 in the case of the amadoriase derived from *Eupenicillium terrenum*, valine at position 277 in the case of the ketoamine oxidase derived from *Pyrenochaeta* sp., valine at position 279 in the case of the ketoamine oxidase derived from *Arthrinium* sp., valine at position 277 in the case of the ketoamine oxidase derived from *Curvularia clavata*, valine at position 279 in the case of the ketoamine oxidase derived from *Neocosmospora vasinfecta*, valine at position 279 in the case of the fructosyl amino acid oxidase derived from *Cryptococcus neoformans*, valine at position 275 in the case of the fructosyl peptide oxidase derived from *Phaeosphaeria nodorum*, valine at position 279 in the case of the fructosyl amino acid oxidase derived from *Aspergillus nidulans*, valine at position 279 in the case of the fructosyl peptide oxidase derived from *Emericella nidulans*, valine at position 277 in the case of the fructosyl amino acid oxidase derived from *Ulocladium* sp., and valine at position 279 in the case of the fructosyl amino acid oxidase derived from *Penicillium janthinellum*.

In the present invention, the "position corresponding to valine at position 12 in the amino acid sequence as shown in SEQ ID NO: 1" is the position corresponding to valine at position 12 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 12 in the amino acid sequence as shown in SEQ ID NO: 1" is valine at position 12 in the case of the amadoriase derived from *Eupenicillium terrenum*, valine at position 12 in the case of the ketoamine oxidase derived from *Pyrenochaeta* sp., valine at position 12 in the case of the ketoamine oxidase derived from *Arthrinium* sp., valine at position 12 in the case of the ketoamine oxidase derived from *Curvularia clavata*, isoleucine at position 12 in the case of the ketoamine oxidase derived from *Neocosmospora vasinfecta*, valine at position 12 in the case of the fructosyl amino acid oxidase derived from *Cryptococcus neoformans*, valine at position 12 in the case of the fructosyl peptide oxidase derived from *Phaeosphaeria nodorum*, valine at position 11 in the case of the fructosyl amino acid oxidase derived from *Aspergillus nidulans*, valine at position 11 in the case of the fructosyl peptide oxidase derived from *Emericella nidulans*, valine at position 12 in the case of the fructosyl amino acid oxidase derived from *Ulocladium* sp., and isoleucine at position 12 in the case of the fructosyl amino acid oxidase derived from *Penicillium janthinellum*.

In the present invention, the "position corresponding to arginine at position 9 in the amino acid sequence as shown in SEQ ID NO: 1" is the position corresponding to arginine at position 9 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to arginine at position 9 in the amino acid sequence as shown in SEQ ID NO: 1" is lysine at position 9 in the case of the amadoriase derived from *Eupenicillium terrenum*, threonine at position 9 in the case of the ketoamine oxidase derived from *Pyrenochaeta* sp., lysine at position 9 in the case of the ketoamine oxidase derived from *Arthrinium* sp., serine at position 9 in the case of the ketoamine oxidase derived from *Curvularia clavata*, threonine at position 9 in the case of the ketoamine oxidase derived from *Neocosmospora vasinfecta*, lysine at position 9 in the case of the fructosyl amino acid oxidase derived from *Cryptococcus neoformans*, serine at position 9 in the case of the fructosyl peptide oxidase derived from *Phaeosphaeria nodorum*, lysine at position 8 in the case of the fructosyl amino acid oxidase derived from *Aspergillus nidulans*, lysine at position 8 in the case of the fructosyl peptide oxidase derived from *Emericella nidulans*, serine at position 9 in the case of the fructosyl amino acid oxidase derived from *Ulocladium* sp., and lysine at position 9 in the case of the fructosyl amino acid oxidase derived from *Penicillium janthinellum*.

In the present invention, the "position corresponding to glutamine at position 77 in the amino acid sequence as shown in SEQ ID NO: 1" is the position corresponding to glutamine at position 77 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamine at position 77 in the amino acid sequence as shown in SEQ ID NO: 1" is aspartic acid at position 77 in the case of the amadoriase derived from *Eupenicillium terrenum*, glutamic acid at position 77 in the case of the ketoamine oxidase derived from *Pyrenochaeta* sp., aspartic acid at position 77 in the case of the ketoamine oxidase derived from *Arthrinium* sp., glutamine at position 77 in the case of the ketoamine oxidase derived from *Curvularia clavata*, aspartic acid at position 77 in the case of the ketoamine oxidase derived from *Neocosmospora vasinfecta*, aspartic acid at position 77 in the case of the fructosyl amino acid oxidase derived from *Cryptococcus neoformans*, glutamine at position 77 in the case of the fructosyl peptide oxidase derived from *Phaeosphaeria nodorum*, aspartic acid at position 76 in the case of the fructosyl amino acid oxidase derived from *Aspergillus nidulans*, aspartic acid at position 76 in the case of the fructosyl peptide oxidase derived from *Emericella nidulans*, glutamine at position 77 in the case of the fructosyl amino acid oxidase derived from *Ulocladium* sp., and aspartic acid at position 77 in the case of the fructosyl amino acid oxidase derived from *Penicillium janthinellum*.

In the present invention, the "position corresponding to serine at position 30 in the amino acid sequence as shown in SEQ ID NO: 1" is the position corresponding to serine at position 30 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to serine at position 30 in the amino acid sequence as shown in SEQ ID NO: 1" is serine at position 30 in the case of the amadoriase derived from *Eupenicillium terrenum*, serine at position 30 in the case of the ketoamine oxidase derived from *Pyrenochaeta* sp., serine at position 30 in the case of the ketoamine oxidase derived from *Arthrinium* sp., serine at position 30 in the case of the ketoamine oxidase derived from *Curvularia clavata*, alanine at position 30 in the case of the ketoamine oxidase derived from *Neocosmospora vasinfecta*, alanine at position 30 in the case of the fructosyl amino acid oxidase derived from *Cryptococcus neoformans*, serine at position 30 in the case of the fructosyl peptide oxidase derived from *Phaeosphaeria nodorum*, alanine at position 29 in the case of the fructosyl amino acid oxidase derived from *Aspergillus nidulans*, alanine at position 29 in the case of the fructosyl peptide oxidase derived from *Emericella nidulans*, serine at position 30 in the case of the fructosyl amino acid oxidase derived from *Ulocladium* sp., and serine at position 30 in the case of the fructosyl amino acid oxidase derived from *Penicillium janthinellum*.

In the present invention, the "position corresponding to valine at position 28 in the amino acid sequence as shown in SEQ ID NO: 1" is the position corresponding to valine at position 28 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 28 in the amino acid sequence as shown in SEQ ID NO: 1" is isoleucine at position 28 in the case of the amadoriase derived from *Eupenicillium terrenum*, leucine at position 28 in the case of the ketoamine oxidase derived from *Pyrenochaeta* sp., leucine at position 28 in the case of the ketoamine oxidase derived from *Arthrinium* sp., valine at position 28 in the case of the ketoamine oxidase derived from *Curvularia clavata*, leucine at position 28 in the case of the ketoamine oxidase derived from *Neocosmospora vasinfecta*, leucine at position 28 in the case of the fructosyl amino acid oxidase derived from *Cryptococcus neoformans*, valine at position 28 in the case of the fructosyl peptide oxidase derived from *Phaeosphaeria nodorum*, leucine at position 27 in the case of the fructosyl amino acid oxidase derived from *Aspergillus nidulans*, leucine at position 27 in the case of the fructosyl peptide oxidase derived from *Emericella nidulans*, valine at position 28 in the case of the fructosyl amino acid oxidase derived from *Ulocladium* sp., and isoleucine at position 28 in the case of the fructosyl amino acid oxidase derived from *Penicillium janthinellum*.

In the present invention, the "position corresponding to serine at position 3 in the amino acid sequence as shown in SEQ ID NO: 1" is the position corresponding to serine at position 3 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to serine at position 3 in the amino acid sequence as shown in SEQ ID NO: 1" is histidine at position 3 in the case of the amadoriase derived from *Eupenicillium terrenum*, alanine at position 3 in the case of the ketoamine oxidase derived from *Pyrenochaeta* sp., alanine at position 3 in the case of the ketoamine oxidase derived from *Arthrinium* sp., proline at position 3 in the case of the ketoamine oxidase derived from *Curvularia clavata*, threonine at position 3 in the case of the ketoamine oxidase derived from *Neocosmospora vasinfecta*, proline at position 3 in the case of the fructosyl amino acid oxidase derived from *Cryptococcus neoformans*, proline at position 3 in the case of the fructosyl peptide oxidase derived from *Phaeosphaeria nodorum*, proline at position 3 in the case of the fructosyl amino acid oxidase derived from *Aspergillus nidulans*, proline at position 3 in the case of the fructosyl peptide oxidase derived from *Emericella nidulans*, proline at position 3 in the case of the fructosyl amino acid oxidase derived from *Ulocladium* sp., and histidine at position 3 in the case of the fructosyl amino acid oxidase derived from *Penicillium janthinellum*.

In the present invention, the "position corresponding to asparagine at position 4 in the amino acid sequence as shown in SEQ ID NO: 1" is the position corresponding to asparagine at position 4 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to asparagine at position 4 in the amino acid sequence as shown in SEQ ID NO: 1" is serine at position 4 in the case of the amadoriase derived from *Eupenicillium terrenum*, serine at position 4 in the case of the ketoamine oxidase derived from *Pyrenochaeta* sp., serine at position 4 in the case of the ketoamine oxidase derived from *Arthrinium* sp., serine at position 4 in the case of the ketoamine oxidase derived from *Curvularia clavata*, proline at position 4 in the case of the ketoamine oxidase derived from *Neocosmospora vasinfecta*, serine at position 4 in the case of the fructosyl amino acid oxidase derived from *Cryptococcus neoformans*, serine at position 4 in the case of the fructosyl peptide oxidase derived from *Phaeosphaeria nodorum*, asparagine at position 4 in the case of the fructosyl amino acid oxidase derived from *Ulocladium* sp., and serine at position 4 in the case of the fructosyl amino acid oxidase derived from *Penicillium janthinellum*. As shown in FIG. 1, the amino acid at the position corresponding to asparagine at position 4 in the amadoriase sequence as shown in SEQ ID NO: 1 is deleted from the fructosyl amino acid oxidase derived from *Aspergillus nidu-*

*lans* and from the fructosyl peptide oxidase derived from *Emericella nidulans*. In the case of the fructosyl amino acid oxidase derived from *Aspergillus nidulans* and the fructosyl peptide oxidase derived from *Emericella nidulans*, however, an amino acid can be inserted into a position corresponding to asparagine at position 4 (i.e., the position of deletion) in the amadoriase sequence as shown in SEQ ID NO: 1. For the convenience of description herein, when the amino acid at the position corresponding to asparagine at position 4 is deleted from the amadoriase sequence as shown in SEQ ID NO: 1, insertion of an amino acid into such position of deletion is within the scope of the amino acid substitutions at a position corresponding to asparagine at position 4 in the amadoriase sequence as shown in SEQ ID NO: 1.

In the present invention, the "position corresponding to valine at position 13 in the amino acid sequence as shown in SEQ ID NO: 1" is the position corresponding to valine at position 13 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 13 in the amino acid sequence as shown in SEQ ID NO: 1" is valine at position 13 in the case of the amadoriase derived from *Eupenicillium terrenum*, valine at position 13 in the case of the ketoamine oxidase derived from *Pyrenochaeta* sp., valine at position 13 in the case of the ketoamine oxidase derived from *Arthrinium* sp., valine at position 13 in the case of the ketoamine oxidase derived from *Curvularia clavata*, isoleucine at position 13 in the case of the ketoamine oxidase derived from *Neocosmospora vasinfecta*, isoleucine at position 13 in the case of the fructosyl amino acid oxidase derived from *Cryptococcus neoformans*, valine at position 13 in the case of the fructosyl peptide oxidase derived from *Phaeosphaeria nodorum*, valine at position 12 in the case of the fructosyl amino acid oxidase derived from *Aspergillus nidulans*, valine at position 12 in the case of the fructosyl peptide oxidase derived from *Emericella nidulans*, valine at position 13 in the case of the fructosyl amino acid oxidase derived from *Ulocladium* sp., and valine at position 13 in the case of the fructosyl amino acid oxidase derived from *Penicillium janthinellum*.

In the present invention, the "position corresponding to phenylalanine at position 286 in the amino acid sequence as shown in SEQ ID NO: 1" is the position corresponding to position 286 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to phenylalanine at position 286 in the amino acid sequence as shown in SEQ ID NO: 1" is phenylalanine at position 286 in the case of the amadoriase derived from *Eupenicillium terrenum*, phenylalanine at position 284 in the case of the ketoamine oxidase derived from *Pyrenochaeta* sp., phenylalanine at position 286 in the case of the ketoamine oxidase derived from *Arthrinium* sp., phenylalanine at position 284 in the case of the ketoamine oxidase derived from *Curvularia clavata*, phenylalanine at position 286 in the case of the ketoamine oxidase derived from *Neocosmospora vasinfecta*, phenylalanine at position 286 in the case of the fructosyl amino acid oxidase derived from *Cryptococcus neoformans*, phenylalanine at position 282 in the case of the fructosyl peptide oxidase derived from *Phaeosphaeria nodorum*, phenylalanine at position 286 in the case of the fructosyl amino acid oxidase derived from *Aspergillus nidulans*, phenylalanine at position 286 in the case of the fructosyl peptide oxidase derived from *Emericella nidulans*, phenylalanine at position 284 in the case of the fructosyl amino acid oxidase derived from *Ulocladium* sp., and phenylalanine at position 286 in the case of the fructosyl amino acid oxidase derived from *Penicillium janthinellum*.

In the present invention, the "position corresponding to position 204 in the amino acid sequence as shown in SEQ ID NO: 1" is the position corresponding to position 204 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to position 204 in the amino acid sequence as shown in SEQ ID NO: 1" is glutamic acid at position 204 in the case of the amadoriase derived from *Eupenicillium terrenum*, glutamic acid at position 202 in the case of the ketoamine oxidase derived from *Pyrenochaeta* sp., glutamic acid at position 204 in the case of the ketoamine oxidase derived from *Arthrinium* sp., glutamic acid at position 202 in the case of the ketoamine oxidase derived from *Curvularia clavata*, glutamic acid at position 204 in the case of the ketoamine oxidase derived from *Neocosmospora vasinfecta*, glutamic acid at position 204 in the case of the fructosyl amino acid oxidase derived from *Cryptococcus neoformans*, glutamic acid at position 200 in the case of the fructosyl peptide oxidase derived from *Phaeosphaeria nodorum*, glutamic acid at position 204 in the case of the fructosyl amino acid oxidase derived from *Aspergillus nidulans*, glutamic acid at position 204 in the case of the fructosyl peptide oxidase derived from *Emericella nidulans*, glutamic acid at position 202 in the case of the fructosyl amino acid oxidase derived from *Ulocladium* sp., and glutamic acid at position 204 in the case of the fructosyl amino acid oxidase derived from *Penicillium janthinellum*.

In the present invention, the "position corresponding to position 338 in the amino acid sequence as shown in SEQ ID NO: 1" is the position corresponding to position 338 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to position 338 in the amino acid sequence as shown in SEQ ID NO: 1" is aspartic acid at position 338 in the case of the amadoriase derived from *Eupenicillium terrenum*, aspartic acid at position 336 in the case of the ketoamine oxidase derived from *Pyrenochaeta* sp., serine at position 339 in the case of the ketoamine oxidase derived from *Arthrinium* sp., glutamic acid at position 336 in the case of the ketoamine oxidase derived from *Curvularia clavata*, aspartic acid at position 338 in the case of the ketoamine oxidase derived from *Neocosmospora vasinfecta*, glutamic acid at position 338 in the case of the fructosyl amino acid oxidase derived from *Cryptococcus neoformans*, asparagine at position 334 in the case of the fructosyl peptide oxidase derived from *Phaeosphaeria nodorum*, aspartic acid at position 338 in the case of the fructosyl amino acid oxidase derived from *Aspergillus nidulans*, aspartic acid at position 338 in the case of the fructosyl peptide oxidase derived from *Emericella nidulans*, glutamic acid at position 336 in the case of the fructosyl amino acid oxidase derived from *Ulocladium* sp., and aspartic acid at position 338 in the case of the fructosyl amino acid oxidase derived from *Penicillium janthinellum*.

In the present invention, the "position corresponding to position 44 in the amino acid sequence as shown in SEQ ID NO: 1" is the position corresponding to position 44 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to position 44 in the amino acid sequence as shown in SEQ ID NO: 1" is lysine at position 44 in the case of the amadoriase derived from *Eupenicillium terrenum*, proline at position 44 in the case of the ketoamine oxidase derived from *Pyrenochaeta* sp., proline at position 44 in the case of the ketoamine oxidase derived from *Arthrinium* sp., proline at position 44 in the case of the ketoamine oxidase derived from *Curvularia clavata*, proline at position 44 in the case of the ketoamine oxidase derived from *Neocosmospora vasinfecta*, leucine at position 44 in the case of the fructosyl amino acid oxidase derived from *Cryptococcus neoformans*, proline at position 44 in the case of the fructosyl peptide oxidase derived from *Phaeosphaeria nodorum*, proline at position 43 in the case of the fructosyl amino acid oxidase derived from *Aspergillus nidulans*, proline at position 43 in the case of the fructosyl peptide oxidase derived from *Emericella nidulans*, proline at position 44 in the case of the fructosyl amino acid oxidase derived from *Ulocladium* sp., and proline at position 44 in the case of the fructosyl amino acid oxidase derived from *Penicillium janthinellum*.

In the present invention, the "position corresponding to position 340 in the amino acid sequence as shown in SEQ ID NO: 1" is the position corresponding to position 340 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to position 340 in the amino acid sequence as shown in SEQ ID NO: 1" is glutamic acid at position 340 in the case of the amadoriase derived from *Eupenicillium terrenum*, glutamic acid at position 338 in the case of the ketoamine oxidase derived from *Pyrenochaeta* sp., glutamic acid at position 341 in the case of the ketoamine oxidase derived from *Arthrinium* sp., glutamic acid at position 338 in the case of the ketoamine oxidase derived from *Curvularia clavata*, proline at position 340 in the case of the ketoamine oxidase derived from *Neocosmospora vasinfecta*, glutamic acid at position 340 in the case of the fructosyl amino acid oxidase derived from *Cryptococcus neoformans*, lysine at position 336 in the case of the fructosyl peptide oxidase derived from *Phaeosphaeria nodorum*, glutamic acid at position 340 in the case of the fructosyl amino acid oxidase derived from *Aspergillus nidulans*, glutamic acid at position 340 in the case of the fructosyl peptide oxidase derived from *Emericella nidulans*, glutamic acid at position 338 in the case of the fructosyl amino acid oxidase derived from *Ulocladium* sp., and glutamic acid at position 340 in the case of the fructosyl amino acid oxidase derived from *Penicillium janthinellum*.

In the present invention, the "position corresponding to position 194 in the amino acid sequence as shown in SEQ ID NO: 1" is the position corresponding to position 194 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to position 194 in the amino acid sequence as shown in SEQ ID NO: 1" is alanine at position 194 in the case of the amadoriase derived from *Eupenicillium terrenum*, alanine at position 194 in the case of the ketoamine oxidase derived from *Pyrenochaeta* sp., alanine at position 194 in the case of the ketoamine oxidase derived from *Arthrinium* sp., alanine at position 194 in the case of the ketoamine oxidase derived from *Curvularia clavata*, alanine at position 194 in the case of the ketoamine oxidase derived from *Neocosmospora vasinfecta*, aspartic acid at position 194 in the case of the fructosyl amino acid oxidase derived from *Cryptococcus neoformans*, alanine at position 192 in the case of the fructosyl peptide oxidase derived from *Phaeosphaeria nodorum*, alanine at position 193 in the case of the fructosyl amino acid oxidase derived from *Aspergillus nidulans*, alanine at position 193 in the case of the fructosyl peptide oxidase derived from *Emericella nidulans*, alanine at position 194 in the case of the fructosyl amino acid oxidase derived from *Ulocladium* sp., and alanine at position 194 in the case of the fructosyl amino acid oxidase derived from *Penicillium janthinellum*.

(Corresponding Positions of Variations for Enhancing Dehydrogenase Activity/Lowering Oxidase Activity)

In this description, the "position corresponding to cysteine at position 280 in the amino acid sequence as shown in SEQ ID NO: 1" is the position corresponding to cysteine at position 280 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can be identified based on FIG. 1 showing the amino acid sequences aligned using the method for identifying an "amino acid residue at a position corresponding to (the amino acid of interest)" described above.

Specifically, the "position corresponding to cysteine at position 280 in the amino acid sequence as shown in SEQ ID NO: 1" is cysteine at position 280 in the case of the amadoriase derived from *Eupenicillium terrenum*, cysteine at position 278 in the case of the ketoamine oxidase derived from *Pyrenochaeta* sp., cysteine at position 280 in the case of the ketoamine oxidase derived from *Arthrinium* sp., cysteine at position 278 in the case of the ketoamine oxidase derived from *Curvularia clavata*, cysteine at position 280 in the case of the ketoamine oxidase derived from *Neocosmospora vasinfecta*, cysteine at position 280 in the case of the fructosyl amino acid oxidase derived from *Cryptococcus neoformans*, cysteine at position 276 in the case of the fructosyl peptide oxidase derived from *Phaeosphaeria nodorum*, cysteine at position 280 in the case of the fructosyl amino acid oxidase derived from *Aspergillus nidulans*, cysteine at position 280 in the case of the fructosyl peptide oxidase derived from *Emericella nidulans*, cysteine at position 278 in the case of the fructosyl amino acid oxidase derived from *Ulocladium* sp., and cysteine at position 280 in the case of the fructosyl amino acid oxidase derived from *Penicillium janthinellum*.

The "position corresponding to phenylalanine at position 267 in the amino acid sequence as shown in SEQ ID NO: 1" is the position corresponding to phenylalanine at position 267 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to phenylalanine at position 267 in the amino acid sequence as shown in SEQ ID NO: 1" is phenylalanine at position 267 in the case of the amadoriase derived from *Eupenicillium terrenum*, phenylalanine at position 265 in the case of the ketoamine oxidase derived from *Pyrenochaeta* sp., phenylalanine at position 267 in the case of the ketoamine oxidase derived from *Arthrinium* sp., phenylalanine at position 265 in the case of the ketoamine oxidase derived from *Curvularia clavata*, phenylalanine at position 267 in the case of the ketoamine oxidase derived from *Neocosmospora vasinfecta*, phenylalanine at position 267 in the case of the fructosyl amino acid oxidase derived from *Cryptococcus neoformans*, phenylalanine at position 263 in the case of the fructosyl peptide oxidase derived from *Phaeosphaeria nodorum*, phenylalanine at position 267 in the case of the fructosyl amino acid oxidase derived from *Aspergillus nidulans*, phenylalanine at position 267 in the case of the fructosyl peptide oxidase derived from *Emericella nidulans*, phenylalanine at position 265 in the case of the fructosyl amino acid oxidase derived from *Ulocladium* sp., and phenylalanine at position 267 in the case of the fructosyl amino acid oxidase derived from *Penicillium janthinellum*.

The "position corresponding to phenylalanine at position 269 in the amino acid sequence as shown in SEQ ID NO: 1" is the position corresponding to phenylalanine at position 269 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to phenylalanine at position 269 in the amino acid sequence as shown in SEQ ID NO: 1" is phenylalanine at position 269 in the case of the amadoriase derived from *Eupenicillium terrenum*, phenylalanine at position 267 in the case of the ketoamine oxidase derived from *Pyrenochaeta* sp., phenylalanine at position 269 in the case of the ketoamine oxidase derived from *Arthrinium* sp., phenylalanine at position 267 in the case of the ketoamine oxidase derived from *Curvularia clavata*, phenylalanine at position 269 in the case of the ketoamine oxidase derived from *Neocosmospora vasinfecta*, phenylalanine at position 269 in the case of the fructosyl amino acid oxidase derived from *Cryptococcus neoformans*, phenylalanine at position 265 in the case of the fructosyl peptide oxidase derived from *Phaeosphaeria nodorum*, phenylalanine at position 269 in the case of the fructosyl amino acid oxidase derived from *Aspergillus nidulans*, isoleucine at position 269 in the case of the fructosyl peptide oxidase derived from *Emericella nidulans*, phenylalanine at position 267 in the case of the fructosyl amino acid oxidase derived from *Ulocladium* sp., and phenylalanine at position 269 in the case of the fructosyl amino acid oxidase derived from *Penicillium janthinellum*.

The "position corresponding to aspartic acid at position 54 in the amino acid sequence as shown in SEQ ID NO: 1" is the position corresponding to aspartic acid at position 54 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to aspartic acid at position 54 in the amino acid sequence as shown in SEQ ID NO: 1" is aspartic acid at position 54 in the case of the amadoriase derived from *Eupenicillium terrenum*, aspartic acid at position 54 in the case of the ketoamine oxidase derived from *Pyrenochaeta* sp., aspartic acid at position 54 in the case of the ketoamine oxidase derived from *Arthrinium* sp., aspartic acid at position 54 in the case of the ketoamine oxidase derived from *Curvularia clavata*, aspartic acid at position 54 in the case of the ketoamine oxidase derived from *Neocosmospora vasinfecta*, aspartic acid at position 54 in the case of the fructosyl amino acid oxidase derived from *Cryptococcus neoformans*, aspartic acid at position 54 in the case of the fructosyl peptide oxidase derived from *Phaeosphaeria nodorum*, aspartic acid at position 53 in the case of the fructosyl amino acid oxidase derived from *Aspergillus nidulans*, aspartic acid at position 53 in the case of the fructosyl peptide oxidase derived from *Emericella nidulans*, aspartic acid at position 54 in the case of the fructosyl amino acid oxidase derived from *Ulocladium* sp., and aspartic acid at position 54 in the case of the fructosyl amino acid oxidase derived from *Penicillium janthinellum*.

The "position corresponding to tyrosine at position 241 in the amino acid sequence as shown in SEQ ID NO: 1" is the position corresponding to tyrosine at position 241 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to tyrosine at position 241 in the amino acid sequence as shown in SEQ ID NO: 1" is phenylalanine at position 241 in the case of the amadoriase derived from *Eupenicillium terrenum*, tyrosine at position 239 in the case of the ketoamine oxidase derived from *Pyrenochaeta* sp., tyrosine at position 241 in the case of the ketoamine oxidase derived from *Arthrinium* sp., tyrosine at position 239 in the case of the ketoamine oxidase derived from *Curvularia clavata*, tyrosine at position 241 in the case of the ketoamine oxidase derived from *Neocosmospora vasinfecta*, tyrosine at position 241 in the case of the fructosyl amino acid oxidase derived from *Cryptococcus neoformans*, tyrosine at position 237 in the case of the fructosyl peptide oxidase derived from *Phaeosphaeria nodorum*, phenylalanine at position 241 in the case of the fructosyl amino acid oxidase derived from *Aspergillus nidulans*, phenylalanine at position 241 in the case of the fructosyl peptide oxidase derived from *Emericella nidulans*, tyrosine at position 239 in the case of the fructosyl amino acid oxidase derived from *Ulocladium* sp., and phenylalanine at position 241 in the case of the fructosyl amino acid oxidase derived from *Penicillium janthinellum*.

(Corresponding Positions of Variations for Modification of Substrate Specificity)

In this description, the amino acid at the "position corresponding to arginine at position 62 in the amino acid sequence as shown in SEQ ID NO: 1" is an amino acid corresponding to arginine at position 62 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can be identified based on FIG. 1 showing the amino acid sequences aligned using the method for identifying an "amino acid residue at a position corresponding to (the amino acid of interest)" described above.

Specifically, the amino acid at the "position corresponding to arginine at position 62 in the amino acid sequence as shown in SEQ ID NO: 1" is arginine at position 62 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl amino acid oxidase derived from *Ulocladium* sp., and the fructosyl amino acid oxidase derived from *Penicillium janthinellum*, it is serine at position 62 in the case of the fructosyl peptide oxidase derived from *Phaeosphaeria nodorum*, it is arginine at position 61 in the case of the fructosyl peptide oxidase derived from *Emericella nidulans*, and it is arginine at position 61 in the case of the fructosyl amino acid oxidase derived from *Aspergillus nidulans*.

The amino acid at the "position corresponding to leucine at position 63 in the amino acid sequence as shown in SEQ ID NO: 1" is the amino acid corresponding to leucine at position 63 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to leucine at position 63 in the amino acid sequence as shown in SEQ ID NO: 1" is leucine at position 63 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, it is isoleucine at position 63 in the case of the fructosyl amino acid oxidase derived from *Cryptococcus neoformans*, and it is leucine at position 62 in the case of the fructosyl amino acid oxidase derived from *Aspergillus nidulans* and the fructosyl peptide oxidase derived from *Emericella nidulans*.

The amino acid at the "position corresponding to glutamic acid at position 102 in the amino acid sequence as shown in SEQ ID NO: 1" is the amino acid corresponding to glutamic acid at position 102 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to glutamic acid at position 102 in the amino acid sequence as shown in SEQ ID NO: 1" is glutamic acid at position 102 in the case of the amadoriase derived from *Eupenicillium terrenum*, the ketoamine oxidase derived from *Curvularia clavata*, the ketoamine oxidase derived from *Neocosmospora vasinfecta*, the fructosyl amino acid oxidase derived from *Cryptococcus neoformans*, and the fructosyl amino acid oxidase derived from *Penicillium janthinellum*, it is lysine at position 102 in the case of the ketoamine oxidase derived from *Pyrenochaeta* sp., the ketoamine oxidase derived from *Arthrinium* sp., the fructosyl peptide oxidase derived from *Phaeosphaeria nodorum*, and the fructosyl amino acid oxidase derived from *Ulocladium* sp., and it is glutamic acid at position 101 in the case of the fructosyl peptide oxidase derived from *Emericella nidulans* and the fructosyl amino acid oxidase derived from *Aspergillus nidulans*.

The amino acid at the "position corresponding to aspartic acid at position 106 in the amino acid sequence as shown in SEQ ID NO: 1" is the amino acid corresponding to aspartic acid at position 106 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to aspartic acid at position 106 in the amino acid sequence as shown in SEQ ID NO: 1" is asparagine at position 106 in the case of the amadoriase derived from *Eupenicillium terrenum*, it is aspartic acid at position 106 in the case of the ketoamine oxidase derived from *Pyrenochaeta* sp., the ketoamine oxidase derived from *Curvularia clavata*, the fructosyl peptide oxidase derived from *Phaeosphaeria nodorum*, and the fructosyl amino acid oxidase derived from *Ulocladium* sp., it is alanine at position 106 in the case of the ketoamine oxidase derived from *Arthrinium* sp., it is glycine at position 106 in the case of the ketoamine oxidase derived from *Neocosmospora vasinfecta*, it is serine at position 106 in the case of the fructosyl amino acid oxidase derived from *Cryptococcus neoformans* and the fructosyl amino acid oxidase derived from *Penicillium janthinellum*, it is lysine at position 105 in the case of the fructosyl peptide oxidase derived from *Emericella nidulans*, and it is glycine at position 105 in the case of the fructosyl amino acid oxidase derived from *Aspergillus nidulans*.

The amino acid at the "position corresponding to glutamine at position 110 in the amino acid sequence as shown in SEQ ID NO: 1" is the amino acid corresponding to glutamine at position 110 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to glutamine at position 110 in the amino acid sequence as shown in SEQ ID NO: 1" is lysine at position 110 in the case of the amadoriase derived from *Eupenicillium terrenum* and the fructosyl amino acid oxidase derived from *Penicillium janthinellum*, it is alanine at position 110 in the case of the ketoamine oxidase derived from *Pyrenochaeta* sp., the ketoamine oxidase derived from *Curvularia clavata*, and the fructosyl amino acid oxidase derived from *Ulocladium* sp., it is glutamine at position 110 in the case of the ketoamine oxidase derived from *Arthrinium* sp., it is glutamic acid at position 110 in the case of the ketoamine oxidase derived from *Neocosmospora vasinfecta*, it is serine at position 110 in the case of the fructosyl amino acid oxidase derived from *Cryptococcus neoformans*, it is glycine at position 110 in the case of the fructosyl peptide oxidase derived from *Phaeosphaeria nodorum*, it is arginine at position 109 in the case of the fructosyl peptide oxidase derived from *Emericella nidulans*, and it is lysine at position 109 in the case of the fructosyl amino acid oxidase derived from *Aspergillus nidulans*.

The amino acid at the "position corresponding to alanine at position 113 in the amino acid sequence as shown in SEQ ID NO: 1" is the amino acid corresponding to alanine at position 113 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to alanine at position 113 in the amino acid sequence as shown in SEQ ID NO: 1" is threonine at position 113 in the case of the amadoriase derived from *Eupenicillium terrenum*, the ketoamine oxidase derived from *Pyrenochaeta* sp., and the ketoamine oxidase derived from *Arthrinium* sp., it is alanine at position 113 in the case of the ketoamine oxidase derived from *Curvularia clavata*, the fructosyl amino acid oxidase derived from *Cryptococcus neoformans*, the fructosyl peptide oxidase derived from *Phaeosphaeria nodorum*, and the fructosyl amino acid oxidase derived from *Ulocladium* sp., it is lysine at position 113 in the case of the ketoamine oxidase derived from *Neocosmospora vasinfecta*, it is serine at position 112 in the case of the fructosyl amino acid oxidase derived from *Aspergillus nidulans* and the fructosyl peptide oxidase derived from *Emericella nidulans*, and aspartic acid at position 113 in the case of the fructosyl amino acid oxidase derived from *Penicillium janthinellum*.

The amino acid at the "position corresponding to alanine at position 355 in the amino acid sequence as shown in SEQ ID NO: 1" is the amino acid corresponding to alanine at position 355 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to alanine at position 355 in the amino acid sequence as shown in SEQ ID NO: 1" is alanine at position 355 in the case of the amadoriase derived from *Eupenicillium terrenum*, the fructosyl amino acid oxidase derived from *Cryptococcus neoformans*, the fructosyl amino acid oxidase derived from *Aspergillus nidulans*, the fructosyl peptide oxidase derived from *Emericella nidulans*, and the fructosyl amino acid oxidase derived from *Penicillium janthinellum*, it is alanine at position 353 in the case of the ketoamine oxidase derived from *Pyrenochaeta* sp., the ketoamine oxidase derived from *Curvularia clavata*, and the fructosyl amino acid oxidase derived from *Ulocladium* sp., it is alanine at position 356 in the case of the ketoamine oxidase derived from *Arthrinium* sp., it is serine at position 355 in the case of the ketoamine oxidase derived from *Neocosmospora vasinfecta*, and it is alanine at position 351 in the case of the fructosyl peptide oxidase derived from *Phaeosphaeria nodorum*.

An amino acid at the "position corresponding to alanine at position 419 in the amino acid sequence as shown in SEQ ID NO: 1" is the amino acid corresponding to alanine at position 419 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to alanine at position 419 in the amino acid sequence as shown in SEQ ID NO: 1" is glycine at position 419 in the case of the amadoriase derived from *Eupenicillium terrenum*, it is alanine at position 418 in the case of the ketoamine oxidase derived from *Pyrenochaeta* sp., the ketoamine oxidase derived from *Curvularia clavata*, and the fructosyl amino acid oxidase derived from *Ulocladium* sp., it is alanine at position 421 in the case of the ketoamine oxidase derived from *Arthrinium* sp., it is alanine at position 420 in the case of the ketoamine oxidase derived from *Neocosmospora vasinfecta*, the fructosyl amino acid oxidase derived from *Cryptococcus neoformans*, and the fructosyl peptide oxidase derived from *Emericella nidulans*, it is serine at position 416 in the case of the fructosyl peptide oxidase derived from *Phaeosphaeria nodorum*, it is serine at position 419 in the case of the fructosyl amino acid oxidase derived from *Penicillium janthinellum*, and it is alanine at position 420 in the case of the fructosyl amino acid oxidase derived from *Aspergillus nidulans*.

An amino acid at the "position corresponding to aspartic acid at position 68 in the amino acid sequence as shown in SEQ ID NO: 1" is the amino acid corresponding to aspartic acid at position 68 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to aspartic acid at position 68 in the amino acid sequence as shown in SEQ ID NO: 1" is aspartic acid at position 68 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, and aspartic acid at position 67 in the case of the fructosyl peptide oxidase derived from *Emericella nidulans* and the fructosyl amino acid oxidase derived from *Aspergillus nidulans*.

An amino acid at the "position corresponding to alanine at position 356 in the amino acid sequence as shown in SEQ ID NO: 1" is the amino acid corresponding to alanine at position 356 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the amino acid at the "position corresponding to alanine at position 356 in the amino acid sequence as shown in SEQ ID NO: 1" is asparagine at position 356 in the case of the amadoriase derived from *Eupenicillium terrenum*, it is alanine at position 354 in the case of the ketoamine oxidase derived from *Pyrenochaeta* sp., alanine at position 357 in the case of the ketoamine oxidase derived from *Arthrinium* sp., alanine at position 354 in the case of the ketoamine oxidase derived from *Curvularia clavata*, alanine at position 356 in the case of the ketoamine oxidase derived from *Neocosmospora vasinfecta*, asparagine at position 356 in the case of the fructosyl amino acid oxidase derived from *Cryptococcus neoformans*, alanine at position 352 in the case of the fructosyl peptide oxidase derived from *Phaeosphaeria nodorum*, asparagine at position 356 in the case of the fructosyl amino acid oxidase derived from *Aspergillus nidulans*, asparagine at position 356 in the case of the fructosyl peptide oxidase derived from *Emericella nidulans*, alanine at position 354 in the case of the fructosyl amino acid oxidase derived from *Ulocladium* sp., and asparagine at position 356 in the case of the fructosyl amino acid oxidase derived from *Penicillium janthinellum*.

(Corresponding Positions of Variations for Improving Cationic Surfactant Tolerance)

The "position corresponding to glutamic acid at position 44 in the amino acid sequence as shown in SEQ ID NO: 1" is as described above.

The "position corresponding to glutamic acid at position 81 in the amino acid sequence as shown in SEQ ID NO: 1" is the position corresponding to glutamic acid at position 81 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 81 in the amino acid sequence as shown in SEQ ID NO: 1" is asparagine at position 81 in the case of the amadoriase derived from *Eupenicillium terrenum*, glutamic acid at position 81 in the case of the ketoamine oxidase derived from *Pyrenochaeta* sp., histidine at position 81 in the case of the ketoamine oxidase derived from *Arthrinium* sp., glutamic acid at position 81 in the case of the ketoamine oxidase derived from *Curvularia clavata*, asparagine at position 81 in the case of the ketoamine oxidase derived from *Neocosmospora vasinfecta*, asparagine at position 81 in the case of the fructosyl amino acid oxidase derived from *Cryptococcus neoformans*, glutamic acid at position 81 in the case of the fructosyl peptide oxidase derived from *Phaeosphaeria nodorum*, asparagine at position 80 in the case of the fructosyl amino acid oxidase derived from *Aspergillus nidulans*, asparagine at position 80 in the case of the fructosyl peptide oxidase derived from *Emericella nidulans*, glutamic acid at position 81 in the case of the fructosyl amino acid oxidase derived from *Ulocladium* sp., and asparagine at position 81 in the case of the fructosyl amino acid oxidase derived from *Penicillium janthinellum*.

The "position corresponding to glutamic acid at position 133 in the amino acid sequence as shown in SEQ ID NO: 1" is the position corresponding to glutamic acid at position 133 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 133 in the amino acid sequence as shown in SEQ ID NO: 1" is glutamic acid at position 133 in the case of the amadoriase derived from *Eupenicillium terrenum*, glutamic acid at position 133 in the case of the ketoamine oxidase derived from *Pyrenochaeta* sp., alanine at position 133 in the case of the ketoamine oxidase derived from *Arthrinium* sp., glutamic acid at position 133 in the case of the ketoamine oxidase derived from *Curvularia clavata*, alanine at position 133 in the case of the ketoamine oxidase derived from *Neocosmospora vasinfecta*, glutamic acid at position 133 in the case of the fructosyl amino acid oxidase derived from *Cryptococcus neoformans*, glutamic acid at position 131 in the case of the fructosyl peptide oxidase derived from *Phaeosphaeria nodorum*, glutamic acid at position 132 in the case of the fructosyl amino acid oxidase derived from *Aspergillus nidulans*, glutamic acid at position 132 in the case of the fructosyl peptide oxidase derived from *Emericella nidulans*, lysine at position 133 in the case of the fructosyl amino acid oxidase derived from *Ulocladium* sp., and aspartic acid at position 133 in the case of the fructosyl amino acid oxidase derived from *Penicillium janthinellum*.

The "position corresponding to glutamic acid at position 253 in the amino acid sequence as shown in SEQ ID NO: 1" is the position corresponding to glutamic acid at position 253 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 253 in the amino acid sequence as shown in SEQ ID NO: 1" is alanine at position 253 in the case of the amadoriase derived from *Eupenicillium terrenum*, alanine at position 251 in the case of the ketoamine oxidase derived from *Pyrenochaeta* sp., glutamic acid at position 253 in the case of the ketoamine oxidase derived from *Arthrinium* sp., glutamic acid at position 251 in the case of the ketoamine oxidase derived from *Curvularia clavata*, valine at position 253 in the case of the ketoamine oxidase derived from *Neocosmospora vasinfecta*, glutamic acid at position 253 in the case of the fructosyl amino acid oxidase derived from *Cryptococcus neoformans*, arginine at position 249 in the case of the fructosyl peptide oxidase derived from *Phaeosphaeria nodorum*, alanine at position 253 in the case of the fructosyl amino acid oxidase derived from *Aspergillus nidulans*, alanine at position 253 in the case of the fructosyl peptide oxidase derived from *Emericella nidulans*, glutamic acid at position 251 in the case of the fructosyl amino acid oxidase derived from *Ulocladium* sp., and glutamine at position 253 in the case of the fructosyl amino acid oxidase derived from *Penicillium janthinellum*.

The "position corresponding to glycine at position 256 in the amino acid sequence as shown in SEQ ID NO: 1" is the position corresponding to glycine at position 256 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glycine at position 256 in the amino acid sequence as shown in SEQ ID NO: 1" is asparagine at position 256 in the case of the amadoriase derived from *Eupenicillium terrenum*, aspartic acid at position 254 in the case of the ketoamine oxidase derived from *Pyrenochaeta* sp., glycine at position 256 in the case of the ketoamine oxidase derived from *Arthrinium* sp., asparagine at position 254 in the case of the ketoamine oxidase derived from *Curvularia clavata*, glycine at position 256 in the case of the ketoamine oxidase derived from *Neocosmospora vasinfecta*, glutamic acid at position 256 in the case of the fructosyl amino acid oxidase derived from *Cryptococcus neoformans*, asparagine at position 252 in the case of the fructosyl peptide oxidase derived from *Phaeosphaeria nodorum*, asparagine at position 256 in the case of the fructosyl amino acid oxidase derived from *Aspergillus nidulans*, asparagine at position 256 in the case of the fructosyl peptide oxidase derived from *Emericella nidulans*, asparagine at position 254 in the case of the fructosyl amino acid oxidase derived from *Ulocladium* sp., and aspartic acid at position 256 in the case of the fructosyl amino acid oxidase derived from *Penicillium janthinellum*.

The "position corresponding to valine at position 257 in the amino acid sequence as shown in SEQ ID NO: 1" is the position corresponding to valine at position 257 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 257 in the amino acid sequence as shown in SEQ ID NO: 1" is valine at position 257 in the case of the amadoriase derived from *Eupenicillium terrenum*, threonine at position 255 in the case of the ketoamine oxidase derived from *Pyrenochaeta* sp., cysteine at position 257 in the case of the ketoamine oxidase derived from *Arthrinium* sp., valine at position 255 in the case of the ketoamine oxidase derived from *Curvularia clavata*, cysteine at position 257 in the case of the ketoamine oxidase derived from *Neocosmospora vasinfecta*, cysteine at position 257 in the case of the fructosyl amino acid oxidase derived from *Cryptococcus neoformans*, serine at position 253 in the case of the fructosyl peptide oxidase derived from *Phaeosphaeria nodorum*, threonine at position 257 in the case of the fructosyl amino acid oxidase derived from *Aspergillus nidulans*, threonine at position 257 in the case of the fructosyl peptide oxidase derived from *Emericella nidulans*, valine at position 255 in the case of the fructosyl amino acid oxidase derived from *Ulocladium* sp., and valine at position 257 in the case of the fructosyl amino acid oxidase derived from *Penicillium janthinellum*.

The "position corresponding to asparagine at position 262 in the amino acid sequence as shown in SEQ ID NO: 1" is the position corresponding to asparagine at position 262 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to asparagine at position 262 in the amino acid sequence as shown in SEQ ID NO: 1" is aspartic acid at position 262 in the case of the amadoriase derived from *Eupenicillium terrenum*, asparagine at position 260 in the case of the ketoamine oxidase derived from *Pyrenochaeta* sp., histidine at position 262 in the case of the ketoamine oxidase derived from *Arthrinium* sp., asparagine at position 260 in the case of the ketoamine oxidase derived from *Curvularia clavata*, histidine at position 262 in the case of the ketoamine oxidase derived from *Neocosmospora vasinfecta*, asparagine at position 262 in the case of the fructosyl amino acid oxidase derived from *Cryptococcus neoformans*, asparagine at position 258 in the case of the fructosyl peptide oxidase derived from *Phaeosphaeria nodorum*, aspartic acid at position 262 in the case of the fructosyl amino acid oxidase derived from *Aspergillus nidulans*, aspartic acid at position 262 in the case of the fructosyl peptide oxidase derived from *Emericella nidulans*, asparagine at position 260 in the case of the fructosyl amino acid oxidase derived from *Ulocladium* sp., and aspartic acid at position 262 in the case of the fructosyl amino acid oxidase derived from *Penicillium janthinellum*.

The "position corresponding to glutamine at position 337 in the amino acid sequence as shown in SEQ ID NO: 1" is the position corresponding to glutamine at position 337 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamine at position 337 in the amino acid sequence as shown in SEQ ID NO: 1" is lysine at position 337 in the case of the amadoriase derived from *Eupenicillium terrenum*, lysine at position 335 in the case of the ketoamine oxidase derived from *Pyrenochaeta* sp., glutamine at position 338 in the case of the ketoamine oxidase derived from *Arthrinium* sp., threonine at position 335 in the case of the ketoamine oxidase derived from *Curvularia clavata*, lysine at position 337 in the case of the ketoamine oxidase derived from *Neocosmospora vasinfecta*, lysine at position 337 in the case of the fructosyl amino acid oxidase derived from *Cryptococcus neoformans*, lysine at position 333 in the case of the fructosyl peptide oxidase derived from *Phaeosphaeria nodorum*, asparagine at position 337 in the case of the fructosyl amino acid oxidase derived from *Aspergillus nidulans*, asparagine at position 337 in the case of the fructosyl peptide oxidase derived from *Emericella nidulans*, threonine at position 335 in the case of the fructosyl amino acid oxidase derived from *Ulocladium* sp., and lysine at position 337 in the case of the fructosyl amino acid oxidase derived from *Penicillium janthinellum*.

"The position corresponding to glutamic acid at position 340 in the amino acid sequence as shown in SEQ ID NO: 1" is as described above.

The "position corresponding to aspartic acid at position 129 in the amino acid sequence as shown in SEQ ID NO: 1" is the position corresponding to aspartic acid at position 129 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to aspartic acid at position 129 in the amino acid sequence as shown in SEQ ID NO: 1" is glutamic acid at position 129 in the case of the amadoriase derived from *Eupenicillium terrenum*, aspartic acid at position 129 in the case of the ketoamine oxidase derived from *Pyrenochaeta* sp., aspartic acid at position 129 in the case of the ketoamine oxidase derived from *Arthrinium* sp., aspartic acid at position 129 in the case of the ketoamine oxidase derived from *Curvularia clavata*, aspartic acid at position 129 in the case of the ketoamine oxidase derived from *Neocosmospora vasinfecta*, serine at position 129 in the case of the fructosyl amino acid oxidase derived from *Cryptococcus neoformans*, aspartic acid at position 127 in the case of the fructosyl peptide oxidase derived from *Phaeosphaeria nodorum*, glutamic acid at position 128 in the case of the fructosyl amino acid oxidase derived from *Aspergillus nidulans*, glutamic acid at position 128 in the case of the fructosyl peptide oxidase derived from *Emericella nidulans*, aspartic acid at position 129 in the case of the fructosyl amino acid oxidase derived from *Ulocladium* sp., and glutamic acid at position 129 in the case of the fructosyl amino acid oxidase derived from *Penicillium janthinellum*.

The "position corresponding to aspartic acid at position 132 in the amino acid sequence as shown in SEQ ID NO: 1" is the position corresponding to aspartic acid at position 132 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to aspartic acid at position 132 in the amino acid sequence as shown in SEQ ID NO: 1" is aspartic acid at position 132 in the case of the amadoriase derived from *Eupenicillium terrenum*, aspartic acid at position 132 in the case of the ketoamine oxidase derived from *Pyrenochaeta* sp., aspartic acid at position 132 in the case of the ketoamine oxidase derived from *Arthrinium* sp., aspartic acid at position 132 in the case of the ketoamine oxidase derived from *Curvularia clavata*, glutamic acid at position 132 in the case of the ketoamine oxidase derived from *Neocosmospora vasinfecta*, aspartic acid at position 132 in the case of the fructosyl amino acid oxidase derived from *Cryptococcus neoformans*, aspartic acid at position 130 in the case of the fructosyl peptide oxidase derived from *Phaeosphaeria nodorum*, aspartic acid at position 131 in the case of the fructosyl amino acid oxidase derived from *Aspergillus nidulans*, aspartic acid at position 131 in the case of the fructosyl peptide oxidase derived from *Emericella nidulans*, aspartic acid at position 132 in the case of the fructosyl amino acid oxidase derived from *Ulocladium* sp., and aspartic acid at position 132 in the case of the fructosyl amino acid oxidase derived from *Penicillium janthinellum*.

The "position corresponding to glutamic acid at position 231 in the amino acid sequence as shown in SEQ ID NO: 1" is the position corresponding to glutamic acid at position 231 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 231 in the amino acid sequence as shown in SEQ ID NO: 1" is glutamic acid at position 231 in the case of the amadoriase derived from *Eupenicillium terrenum*, glutamic acid at position 229 in the case of the ketoamine oxidase derived from *Pyrenochaeta* sp., glutamic acid at position 231 in the case of the ketoamine oxidase derived from *Arthrinium* sp., glutamic acid at position 229 in the case of the ketoamine oxidase derived from *Curvularia clavata*, glutamic acid at position 231 in the case of the ketoamine oxidase derived from *Neocosmospora vasinfecta*, glutamic acid at position 231 in the case of the fructosyl amino acid oxidase derived from *Cryptococcus neoformans*, histidine at position 227 in the case of the fructosyl peptide oxidase derived from *Phaeosphaeria nodorum*, glutamic acid at position 231 in the case of the fructosyl amino acid oxidase derived from *Aspergillus nidulans*, glutamic acid at position 231 in the case of the fructosyl peptide oxidase derived from *Emericella nidulans*, glutamine at position 229 in the case of the fructosyl amino acid oxidase derived from *Ulocladium* sp., and glutamic acid at position 231 in the case of the fructosyl amino acid oxidase derived from *Penicillium janthinellum*.

The "position corresponding to aspartic acid at position 232 in the amino acid sequence as shown in SEQ ID NO: 1" is the position corresponding to aspartic acid at position 232 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to aspartic acid at position 232 in the amino acid sequence as shown in SEQ ID NO: 1" is aspartic acid at position 232 in the case of the amadoriase derived from *Eupenicillium terrenum*, aspartic acid at position 230 in the case of the ketoamine oxidase derived from *Pyrenochaeta* sp., glutamic acid at position 232 in the case of the ketoamine oxidase derived from *Arthrinium* sp., aspartic acid at position 230 in the case of the ketoamine oxidase derived from *Curvularia clavata*, glutamic acid at position 232 in the case of the ketoamine oxidase derived from *Neocosmospora vasinfecta*, glycine at position 232 in the case of the fructosyl amino acid oxidase derived from *Cryptococcus neoformans*, glutamic acid at position 228 in the case of the fructosyl peptide oxidase derived from *Phaeosphaeria nodorum*, glutamic acid at position 232 in the case of the fructosyl amino acid oxidase derived from *Aspergillus nidulans*, glutamic acid at position 232 in the case of the fructosyl peptide oxidase derived from *Emericella nidulans*, aspartic acid at position 230 in the case of the fructosyl amino acid oxidase derived from *Ulocladium* sp., and aspartic acid at position 232 in the case of the fructosyl amino acid oxidase derived from *Penicillium janthinellum*.

The "position corresponding to glutamic acid at position 249 in the amino acid sequence as shown in SEQ ID NO: 1" is the position corresponding to glutamic acid at position 249 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 249 in the amino acid sequence as shown in SEQ ID NO: 1" is lysine at position 249 in the case of the amadoriase derived from *Eupenicillium terrenum*, lysine at position 247 in the case of the ketoamine oxidase derived from *Pyrenochaeta* sp., histidine at position 249 in the case of the ketoamine oxidase derived from *Arthrinium* sp., glutamic acid at position 247 in the case of the ketoamine oxidase derived from *Curvularia clavata*, glutamic acid at position 249 in the case of the ketoamine oxidase derived from *Neocosmospora vasinfecta*, glutamic acid at position 249 in the case of the fructosyl amino acid oxidase derived from *Cryptococcus neoformans*, glutamic acid at position 245 in the case of the fructosyl peptide oxidase derived from *Phaeosphaeria nodorum*, alanine at position 249 in the case of the fructosyl amino acid oxidase derived from *Aspergillus nidulans*, alanine at position 249 in the case of the fructosyl peptide oxidase derived from *Emericella nidulans*, serine at position 247 in the case of the fructosyl amino acid oxidase derived from *Ulocladium* sp., and glutamine at position 249 in the case of the fructosyl amino acid oxidase derived from *Penicillium janthinellum*.

(Corresponding Positions of Deletions for Improvement of Heat Stability and Amino Acid Substitutions for Improvement of Heat Stability)

The phrase "positions corresponding to 3 amino acid residues from the carboxyl terminus of the amadoriase sequence as shown in SEQ ID NO: 1" used herein refers to 3 amino acid residues from the carboxyl terminus of the amino acid sequence as shown in SEQ ID NO: 1, when the amino acid sequence of the amadoriase is compared with the amino acid sequence of the amadoriase derived from the genus *Coniochaeta* as shown in SEQ ID NO: 1. A sequence comprising 3 residues at this position in the amadoriase derived from the genus *Coniochaeta* comprises proline at position 435, lysine at position 436, and leucine at position 437, and the amino acid sequence at positions corresponding thereto can be identified based on FIG. 1 showing the amino acid sequences aligned in the manner described above.

Specifically, 3 amino acid residues at the carboxyl terminus are alanine at position 435, histidine at position 436, and leucine at position 437 in the case of the amadoriase derived from *Eupenicillium terrenum*, 3 amino acid residues at the carboxyl terminus are alanine at position 438, lysine at position 439, and leucine at position 440 in the case of the ketoamine oxidase derived from *Pyrenochaeta* sp., 3 amino acid residues at the carboxyl terminus are histidine at position 450, lysine at position 451, and leucine at position 452 in the case of the ketoamine oxidase derived from *Arthrinium* sp., 3 amino acid residues at the carboxyl terminus are serine at position 438, lysine at position 439, and leucine at position 440 in the case of the ketoamine oxidase derived from *Curvularia clavata*, 3 amino acid residues at the carboxyl terminus are alanine at position 435, asparagine at position 436, and leucine at position 437 in the case of the fructosyl peptide oxidase derived from *Phaeosphaeria nodorum*, 3 amino acid residues at the carboxyl terminus are alanine at position 436, lysine at position 437, and methionine at position 438 in the case of the fructosyl amino acid oxidase derived from *Aspergillus nidulans*, 3 amino acid residues at the carboxyl terminus are alanine at position 436, lysine at position 437, and methionine at position 438 in the case of the fructosyl peptide oxidase derived from *Emericella nidulans*, 3 amino acid residues at the carboxyl terminus are alanine at position 439, lysine at position 440, and leucine at position 441 in the case of the fructosyl amino acid oxidase derived from *Ulocladium* sp., and 3 amino acid residues at the carboxyl terminus are alanine at position 435, lysine at position 436, and leucine at position 437 in the case of the fructosyl amino acid oxidase derived from *Penicillium janthinellum*.

The "position corresponding to phenylalanine at position 43 in the amino acid sequence as shown in SEQ ID NO: 1" is the position corresponding to phenylalanine at position 43 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid residue of interest can be identified based on FIG. 1 showing the amino acid sequences aligned using the method for identifying an "amino acid at a position corresponding to (the amino acid of interest)" described above.

Specifically, the "position corresponding to phenylalanine at position 43 in the amino acid sequence as shown in SEQ ID NO: 1" is tyrosine at position 43 in the case of the amadoriase derived from *Eupenicillium terrenum*, tyrosine at position 43 in the case of the ketoamine oxidase derived from *Pyrenochaeta* sp., tyrosine at position 43 in the case of the ketoamine oxidase derived from *Arthrinium* sp., tyrosine at position 43 in the case of the ketoamine oxidase derived from *Curvularia clavata*, tyrosine at position 43 in the case of the ketoamine oxidase derived from *Neocosmospora vasinfecta*, tyrosine at position 43 in the case of the fructosyl amino acid oxidase derived from *Cryptococcus neoformans*, tyrosine at position 43 in the case of the fructosyl peptide oxidase derived from *Phaeosphaeria nodorum*, cysteine at position 42 in the case of the fructosyl amino acid oxidase derived from *Aspergillus nidulans*, tyrosine at position 43 in the case of the fructosyl amino acid oxidase derived from *Ulocladium* sp., and tyrosine at position 43 in the case of the fructosyl amino acid oxidase derived from *Penicillium janthinellum*.

The "position corresponding to histidine at position 53 in the amadoriase sequence as shown in SEQ ID NO: 1" is the position corresponding to histidine at position 53 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to histidine at position 53 in the amadoriase sequence as shown in SEQ ID NO: 1" is histidine at position 53 in the case of the amadoriase derived from *Eupenicillium terrenum*, asparagine at position 53 in the case of the ketoamine oxidase derived from *Pyrenochaeta* sp., asparagine at position 53 in the case of the ketoamine oxidase derived from *Arthrinium* sp., asparagine at position 53 in the case of the ketoamine oxidase derived from *Curvularia clavata*, asparagine at position 53 in the case of the ketoamine oxidase derived from *Neocosmospora vasinfecta*, asparagine at position 53 in the case of the fructosyl amino acid oxidase derived from *Cryptococcus neoformans*, asparagine at position 53 in the case of the fructosyl peptide oxidase derived from *Phaeosphaeria nodorum*, tyrosine at position 52 in the case of the fructosyl amino acid oxidase derived from *Aspergillus nidulans*, asparagine at position 53 in the case of the fructosyl amino acid oxidase derived from *Ulocladium* sp., and tyrosine at position 53 in the case of the fructosyl amino acid oxidase derived from *Penicillium janthinellum*.

The "position corresponding to alanine at position 151 in the amino acid sequence as shown in SEQ ID NO: 1" is the position corresponding to alanine at position 151 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to alanine at position 151 in the amino acid sequence as shown in SEQ ID NO: 1" is glycine at position 151 in the case of the amadoriase derived from *Eupenicillium terrenum*, alanine at position 151 in the case of the ketoamine oxidase derived from *Pyrenochaeta* sp., alanine at position 151 in the case of the ketoamine oxidase derived from *Arthrinium* sp., alanine at position 151 in the case of the ketoamine oxidase derived from *Curvularia clavata*, alanine at position 151 in the case of the ketoamine oxidase derived from *Neocosmospora vasinfecta*, alanine at position 151 in the case of the fructosyl amino acid oxidase derived from *Cryptococcus neoformans*, alanine at position 149 in the case of the fructosyl peptide oxidase derived from *Phaeosphaeria nodorum*, glycine at position 151 in the case of the fructosyl amino acid oxidase derived from *Aspergillus nidulans*, alanine at position 151 in the case of the fructosyl amino acid oxidase derived from *Ulocladium* sp., and glycine at position 151 in the case of the fructosyl amino acid oxidase derived from *Penicillium janthinellum*.

The "position corresponding to alanine at position 185 in the amadoriase sequence as shown in SEQ ID NO: 1" is the position corresponding to alanine at position 185 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to alanine at position 185 in the amadoriase sequence as shown in SEQ ID NO: 1" is alanine at position 185 in the case of the amadoriase derived from *Eupenicillium terrenum*, alanine at position 185 in the case of the ketoamine oxidase derived from *Pyrenochaeta* sp., alanine at position 185 in the case of the ketoamine oxidase derived from *Arthrinium* sp., alanine at position 185 in the case of the ketoamine oxidase derived from *Curvularia clavata*, alanine at position 185 in the case of the ketoamine oxidase derived from *Neocosmospora vasinfecta*, alanine at position 185 in the case of the fructosyl amino acid oxidase derived from *Cryptococcus neoformans*, alanine at position 183 in the case of the fructosyl peptide oxidase derived from *Phaeosphaeria nodorum*, alanine at position 184 in the case of the fructosyl amino acid oxidase derived from *Aspergillus nidulans*, alanine at position 185 in the case of the fructosyl amino acid oxidase derived from *Ulocladium* sp., and alanine at position 185 in the case of the fructosyl amino acid oxidase derived from *Penicillium janthinellum*.

The "position corresponding to glutamic acid at position 196 in the amadoriase sequence as shown in SEQ ID NO: 1" is the position corresponding to glutamic acid at position 196 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to glutamic acid at position 196 in the amadoriase sequence as shown in SEQ ID NO: 1" is aspartic acid at position 196 in the case of the amadoriase derived from *Eupenicillium terrenum*, glycine at position 196 in the case of the ketoamine oxidase derived from *Pyrenochaeta* sp., aspartic acid at position 196 in the case of the ketoamine oxidase derived from *Arthrinium* sp., glycine at position 196 in the case of the ketoamine oxidase derived from *Curvularia clavata*, aspartic acid at position 196 in the case of the ketoamine oxidase derived from *Neocosmospora vasinfecta*, aspartic acid at position 196 in the case of the fructosyl amino acid oxidase derived from *Cryptococcus neoformans*, glycine at position 194 in the case of the fructosyl peptide oxidase derived from *Phaeosphaeria nodorum*, alanine at position 195 in the case of the fructosyl amino acid oxidase derived from *Aspergillus nidulans*, glycine at position 196 in the case of the fructosyl amino acid oxidase derived from *Ulocladium* sp., and aspartic acid at position 196 in the case of the fructosyl amino acid oxidase derived from *Penicillium janthinellum*.

The "position corresponding to serine at position 299 in the amino acid sequence as shown in SEQ ID NO: 1" is the position corresponding to serine at position 299 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to serine at position 299 in the amino acid sequence as shown in SEQ ID NO: 1" is serine at position 299 in the case of the amadoriase derived from *Eupenicillium terrenum*, alanine at position 297 in the case of the ketoamine oxidase derived from *Pyrenochaeta* sp., alanine at position 300 in the case of the ketoamine oxidase derived from *Arthrinium* sp., alanine at position 297 in the case of the ketoamine oxidase derived from *Curvularia clavata*, alanine at position 299 in the case of the ketoamine oxidase derived from *Neocosmospora vasinfecta*, serine at position 299 in the case of the fructosyl amino acid oxidase derived from *Cryptococcus neoformans*, alanine at position 295 in the case of the fructosyl peptide oxidase derived from *Phaeosphaeria nodorum*, alanine at position 299 in the case of the fructosyl amino acid oxidase derived from *Aspergillus nidulans*, alanine at position 297 in the case of the fructosyl amino acid oxidase derived from *Ulocladium* sp., and serine at position 299 in the case of the fructosyl amino acid oxidase derived from *Penicillium janthinellum*.

The "position corresponding to valine at position 323 in the amino acid sequence as shown in SEQ ID NO: 1" is the position corresponding to valine at position 323 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to valine at position 323 in the amino acid sequence as shown in SEQ ID NO: 1" is valine at position 323 in the case of the amadoriase derived from *Eupenicillium terrenum*, alanine at position 321 in the case of the ketoamine oxidase derived from *Pyrenochaeta* sp., glutamine at position 324 in the case of the ketoamine oxidase derived from *Arthrinium* sp., lysine at position 321 in the case of the ketoamine oxidase derived from *Curvularia clavata*, glutamic acid at position 323 in the case of the ketoamine oxidase derived from *Neocosmospora vasinfecta*, alanine at position 323 in the case of the fructosyl amino acid oxidase derived from *Cryptococcus neoformans*, valine at position 319 in the case of the fructosyl peptide oxidase derived from *Phaeosphaeria nodorum*, valine at position 323 in the case of the fructosyl amino acid oxidase derived from *Aspergillus nidulans*, valine at position 321 in the case of the fructosyl amino acid oxidase derived from *Ulocladium* sp., and glutamic acid at position 323 in the case of the fructosyl amino acid oxidase derived from *Penicillium janthinellum*.

The "position corresponding to threonine at position 350 in the amino acid sequence as shown in SEQ ID NO: 1" is the position corresponding to threonine at position 350 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned in accordance with the method described above.

Specifically, the "position corresponding to threonine at position 350 in the amino acid sequence as shown in SEQ ID NO: 1" is threonine at position 350 in the case of the amadoriase derived from *Eupenicillium terrenum*, threonine at position 348 in the case of the ketoamine oxidase derived from *Pyrenochaeta* sp., threonine at position 351 in the case of the ketoamine oxidase derived from *Arthrinium* sp., threonine at position 348 in the case of the ketoamine oxidase derived from *Curvularia clavata*, threonine at position 350 in the case of the ketoamine oxidase derived from *Neocosmospora vasinfecta*, threonine at position 350 in the case of the fructosyl amino acid oxidase derived from *Cryptococcus neoformans*, threonine at position 346 in the case of the fructosyl peptide oxidase derived from *Phaeosphaeria nodorum*, threonine at position 350 in the case of the fructosyl amino acid oxidase derived from *Aspergillus nidulans*, threonine at position 348 in the case of the fructosyl amino acid oxidase derived from *Ulocladium* sp., and threonine at position 350 in the case of the fructosyl amino acid oxidase derived from *Penicillium janthinellum*. (Reversion)

In this description, an amino acid at a position corresponding to an amino acid at a particular position is described with reference to the amino acid sequence as shown in SEQ ID NO: 1 for convenience. However, some naturally-occurring amadoriases have amino acids corresponding to the amino acid substitutions according to the present invention at positions corresponding to the positions of particular amino acids, when the sequences thereof are aligned with the amino acid sequence as shown in SEQ ID NO: 1. For example, an amino acid at position 80 in SEQ ID NO: 1 is lysine, and substitution thereof with arginine is equivalent to the variation according to the present invention. In the case of the ketoamine oxidase derived from *Pyrenochaeta* sp., the ketoamine oxidase derived from *Curvularia clavata*, the ketoamine oxidase derived from *Neocosmospora vasinfecta*, and the fructosyl amino acid oxidase derived from *Cryptococcus neoformans*, however, the amino acid at the position corresponding to position 80 in SEQ ID NO: 1 is arginine. In the case of such amadoriase, substitution of arginine at a position corresponding to position 80 in SEQ ID NO: 1 with lysine is a type of reversion in SEQ ID NO: 1. According to a particular embodiment, such substitution is not within the scope of the amino acid substitution according to the present invention. When such an amadoriase has arginine at an amino acid at the position corresponding to position 80 in SEQ ID NO: 1, in contrast, lysine had been substituted with arginine in SEQ ID NO: 1. According to one embodiment, therefore, a naturally-occurring amadoriase comprising the amino acid sequence as shown in SEQ ID NO: 1 in which the amino acid at the position corresponding to lysine at position 80 is arginine, such as the ketoamine oxidase derived from *Pyrenochaeta* sp., the ketoamine oxidase derived from *Curvularia clavata*, the ketoamine oxidase derived from *Neocosmospora vasinfecta*, or the fructosyl amino acid oxidase derived from *Cryptococcus neoformans* is within the scope of the amadoriase comprising an amino acid substitution at a position corresponding to lysine at position 80 in SEQ ID NO: 1, when aligned with the amino acid sequence as shown in SEQ ID NO: 1.

Examples of amino acids within the scope of the amino acid substitutions aimed at improved surfactant tolerance according to the present invention are described below.

The amino acid at the position corresponding to position 3 in the amino acid sequence as shown in SEQ ID NO: 1 is threonine in the case of the ketoamine oxidase derived from *Neocosmospora vasinfecta*. According to an embodiment, such amino acid position is within the scope of the amino acid substitution at a position corresponding to position 3 in SEQ ID NO: 1. According to an embodiment, the amino acid substitution according to the present invention does not encompass substitution of an amino acid at such position with serine.

The amino acid at the position corresponding to position 4 in the amino acid sequence as shown in SEQ ID NO: 1 is proline in the case of the ketoamine oxidase derived from *Neocosmospora vasinfecta*. According to an embodiment, such amino acid position is within the scope of the amino acid substitution at a position corresponding to position 4 in SEQ ID NO: 1. According to an embodiment, the amino acid substitution according to the present invention does not encompass substitution of an amino acid at such position with asparagine.

The amino acid at the position corresponding to position 9 in the amino acid sequence as shown in SEQ ID NO: 1 is threonine in the case of the ketoamine oxidase derived from *Pyrenochaeta* sp., serine in the case of the ketoamine oxidase derived from *Curvularia clavata*, threonine in the case of the ketoamine oxidase derived from *Neocosmospora vasinfecta*, serine in the case of the fructosyl peptide oxidase derived from *Phaeosphaeria nodorum*, and serine in the case of the fructosyl amino acid oxidase derived from *Ulocladium* sp. According to an embodiment, such amino acid position is within the scope of the amino acid substitution at a position corresponding to position 9 in SEQ ID NO: 1. According to an embodiment, the amino acid substitution according to the present invention does not encompass substitution of an amino acid at such position with arginine.

The amino acid at the position corresponding to position 12 in the amino acid sequence as shown in SEQ ID NO: 1 is isoleucine in the case of the ketoamine oxidase derived from *Neocosmospora vasinfecta* and the fructosyl amino acid oxidase derived from *Penicillium janthinellum*. According to an embodiment, such amino acid position is within the scope of the amino acid substitution at a position corresponding to position 12 in SEQ ID NO: 1. According to an embodiment, the amino acid substitution according to the present invention does not encompass substitution of an amino acid at such position with valine.

The amino acid at the position corresponding to position 13 in the amino acid sequence as shown in SEQ ID NO: 1 is isoleucine in the case of the ketoamine oxidase derived from *Neocosmospora vasinfecta* and the fructosyl amino acid oxidase derived from *Cryptococcus neoformans*. According to an embodiment, such amino acid position is within the scope of the amino acid substitution at a position corresponding to position 13 in SEQ ID NO: 1. According to an embodiment, the amino acid substitution according to the present invention does not encompass substitution of an amino acid at such position with valine.

The amino acid at the position corresponding to position 28 in the amino acid sequence as shown in SEQ ID NO: 1 is isoleucine in the case of the amadoriase derived from *Eupenicillium terrenum*, leucine in the case of the ketoamine oxidase derived from *Pyrenochaeta* sp., leucine in the case of the ketoamine oxidase derived from *Arthrinium* sp., leucine in the case of the ketoamine oxidase derived from *Neocosmospora vasinfecta*, leucine in the case of the fructosyl amino acid oxidase derived from *Cryptococcus neoformans*, leucine in the case of the fructosyl amino acid oxidase derived from *Aspergillus nidulans*, leucine in the case of the fructosyl peptide oxidase derived from *Emericella nidulans*, and isoleucine in the case of the fructosyl amino acid oxidase derived from *Penicillium janthinellum*. According to an embodiment, such amino acid position is within the scope of the amino acid substitution at a position corresponding to position 28 in SEQ ID NO: 1. According to an embodiment, the amino acid substitution according to the present invention does not encompass substitution of an amino acid at such position with valine.

The amino acid at the position corresponding to position 30 in the amino acid sequence as shown in SEQ ID NO: 1 is alanine in the case of the ketoamine oxidase derived from *Neocosmospora vasinfecta*, alanine in the case of the fructosyl amino acid oxidase derived from *Cryptococcus neoformans*, alanine in the case of the fructosyl amino acid oxidase derived from *Aspergillus nidulans*, and alanine in the case of the fructosyl peptide oxidase derived from *Emericella nidulans*. According to an embodiment, such amino acid position is within the scope of the amino acid substitution at a position corresponding to position 30 in SEQ ID NO: 1. According to an embodiment, the amino acid substitution according to the present invention does not encompass substitution of an amino acid at such position with serine.

The amino acid at the position corresponding to position 44 in the amino acid sequence as shown in SEQ ID NO: 1 is lysine in the case of the amadoriase derived from *Eupenicillium terrenum*. According to an embodiment, such amino acid position is within the scope of the amino acid substitution at a position corresponding to position 44 in SEQ ID NO: 1. According to an embodiment, the amino acid substitution according to the present invention does not encompass substitution of an amino acid at such position with glutamic acid.

The amino acid at the position corresponding to position 71 in the amino acid sequence as shown in SEQ ID NO: 1 is leucine in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl peptide oxidase derived from *Phaeosphaeria nodorum*, the fructosyl amino acid oxidase derived from *Aspergillus nidulans*, the fructosyl peptide oxidase derived from *Emericella nidulans*, the fructosyl amino acid oxidase derived from *Ulocladium* sp., and the fructosyl amino acid oxidase derived from *Penicillium janthinellum*. According to an embodiment, such amino acid position is within the scope of the amino acid substitution at a position corresponding to position 71 in SEQ ID NO: 1. According to an embodiment, the amino acid substitution according to the present invention does not encompass substitution of an amino acid at such position with methionine.

The amino acid at the position corresponding to position 77 in the amino acid sequence as shown in SEQ ID NO: 1 is aspartic acid in the case of the amadoriase derived from *Eupenicillium terrenum*, glutamic acid in the case of the ketoamine oxidase derived from *Pyrenochaeta* sp., aspartic acid in the case of the ketoamine oxidase derived from *Arthrinium* sp., aspartic acid in the case of the ketoamine oxidase derived from *Neocosmospora vasinfecta*, aspartic acid in the case of the fructosyl amino acid oxidase derived from *Cryptococcus neoformans*, aspartic acid in the case of the fructosyl amino acid oxidase derived from *Aspergillus nidulans*, aspartic acid in the case of the fructosyl peptide oxidase derived from *Emericella nidulans*, and aspartic acid in the case of the fructosyl amino acid oxidase derived from *Penicillium janthinellum*. According to an embodiment, such amino acid position is within the scope of the amino acid substitution at a position corresponding to position 77 in SEQ ID NO: 1. According to an embodiment, the amino acid substitution according to the present invention does not encompass substitution of an amino acid at such position with glutamine.

The amino acid at the position corresponding to position 80 in the amino acid sequence as shown in SEQ ID NO: 1 is arginine in the case of the ketoamine oxidase derived from *Pyrenochaeta* sp., the ketoamine oxidase derived from *Curvularia clavata*, the ketoamine oxidase derived from *Neocosmospora vasinfecta*, and the fructosyl amino acid oxidase derived from *Cryptococcus neoformans*. According to an embodiment, such amino acid position is within the scope of the amino acid substitution at a position corresponding to position 80 in SEQ ID NO: 1. According to an embodiment, the amino acid substitution according to the present invention does not encompass substitution of an amino acid at such position with lysine.

The amino acid at the position corresponding to position 172 in the amino acid sequence as shown in SEQ ID NO: 1 is glutamic acid in the case of the ketoamine oxidase derived from *Arthrinium* sp. and the ketoamine oxidase derived from *Neocosmospora vasinfecta*. According to an embodiment, such amino acid position is within the scope of the amino acid substitution at a position corresponding to position 172 in SEQ ID NO: 1. According to an embodiment, the amino acid substitution according to the present invention does not encompass substitution of an amino acid at such position with phenylalanine.

The amino acid at the position corresponding to position 175 in the amino acid sequence as shown in SEQ ID NO: 1 is lysine in the case of the ketoamine oxidase derived from *Pyrenochaeta* sp., arginine in the case of the ketoamine oxidase derived from *Arthrinium* sp., and arginine in the case of the ketoamine oxidase derived from *Neocosmospora vasinfecta*. According to an embodiment, such amino acid position is within the scope of the amino acid substitution at a position corresponding to position 175 in SEQ ID NO: 1. According to an embodiment, the amino acid substitution according to the present invention does not encompass substitution of an amino acid at such position with glutamic acid.

The amino acid at the position corresponding to position 340 in the amino acid sequence as shown in SEQ ID NO: 1 is lysine in the case of the ketoamine oxidase derived from Neocosmospora vasinfecta. According to an embodiment, such amino acid position is within the scope of the amino acid substitution at a position corresponding to position 340 in SEQ ID NO: 1. According to an embodiment, the amino acid substitution according to the present invention does not encompass substitution of an amino acid at such position with glutamic acid.

(Production of the Amadoriase of the Present Invention)

In order to produce the amadoriase that is excellent in surfactant tolerance obtained in the manner described above using a strain having the ability to produce such amadoriase, although the strain may be cultured by conventional solid culture methods, liquid culture is preferably adopted where possible.

Examples of media to culture the aforementioned strains include media prepared by adding one or more inorganic salts selected from among, for example, sodium chloride, monopotassium phosphate, dipotassium phosphate, magnesium sulfate, magnesium chloride, ferric chloride, ferric sulfate, and manganese sulfate to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

It is appropriate to adjust the initial pH of the media to 7 to 9.

Culture can be performed under any conditions. For example, culture can be performed at 20° C. to 42° C., preferably at about 30° C. for 4 to 24 hours, and more preferably at about 30° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove the solid content, and nucleic acid is removed with the aid of streptomycin sulfate, protamine sulfate, or manganese sulfate, according to need. Ammonium sulfate, alcohol, or acetone is added to the solution, so as to fractionate the solution, and sediments are then collected to obtain the crude enzymes of the amadoriases.

A purified amadoriase enzyme preparation can be obtained from the crude enzyme of the aforementioned amadoriase by a method appropriately selected from among: gel filtration methods using Sephadex, Superdex, or Ultrogel; adsorption-elution methods using ion exchange carriers; electrophoretic methods using polyacrylamide gels, etc.; adsorption-elution methods using hydroxyapatite; sedimentation methods such as sucrose density-gradient centrifugation; affinity chromatography methods; and fractionation methods using a molecular sieve membrane, a hollow-fiber membrane, etc. Alternatively, the aforementioned methods can adequately be performed in combination, so as to obtain a purified amadoriase enzyme preparation. Thus, the amadoriase of interest having enhanced substrate specificity can be obtained.

(Surfactant in the Present Invention (Disclosure))

A surfactant in the present invention is not particularly limited as long as a method of measuring HbA1c of the present invention can be carried out in the presence of the surfactant, and a nonionic surfactant and an ionic surfactant such as a cationic surfactant, an anionic surfactant, and an amphoteric surfactant, can be mentioned and particularly, a cationic surfactant and an anionic surfactant are preferable. Unless stated otherwise, the term surfactant as used herein encompasses one or more surfactants.

The surfactant in the present invention can be a surfactant having a critical micelle concentration (CMC) of 130 mM or lower, 100 mM or lower, 70 mM or lower, 50 mM or lower, 20 mM or lower, 10 mM or lower, 9 mM or lower, 8 mM or lower, 7 mM or lower, 6 mM or lower, 5 mM or lower, 4.5 mM or lower, 4 mM or lower, 3.5 mM or lower, 3 mM or lower, 2.5 mM or lower, 2 mM or lower, 1.5 mM or lower, or 1 mM or lower at 25° C. In an embodiment, the critical micelle concentration of the surfactant of the present invention can be 0.1 mM or 0.01 mM or higher, preferably 50 mM or lower, more preferably 20 mM or lower, and most preferably 5 mM or lower at 25° C. The critical micelle concentration refers to the critical concentration above which micelles of a surfactant are formed in a solution and below which micelles are not formed. In general, for lower critical micelle concentrations, a surfactant is likely to form micelles at a lower concentration, and a surfactant action is likely to be stronger. A person skilled in the art can determine the critical micelle concentration of a desired surfactant by a conventional method. For example, a commercially available kit, which measures a critical micelle concentration of a surfactant based on a change in fluorescence of a fluorescent reagent interacting with the surfactant, can be used (for example, Detergent Critical Micelle Concentration (CMC) Assay Kit manufactured by PFP).

For example, CMC of sodium octyl sulfate is 130 mM (see BULL. CHEM. SOC. JAPAN, 38, 1700, 1965), CMC of sodium decyl sulfate is 30 mM (see J. COLLOID. DCI, 16, 484, 1961), CMC of sodium dodecyl sulfate (SDS) is 8.3 mM (see the data in the catalog provided by Hampton Research Corp.), CMC of sodium tetradecyl sulfate is 2 mM (see J. COLLOID. DCI, 16, 484, 1961), CMC of sodium hexadecyl sulfate is 0.5 mM (see J. COLLOID. DCI, 16, 484, 1961), and CMC of sodium octadecyl sulfate is 0.6 mM (see "Kaimenkasseizai Binran (Handbook of Surfactants)," Sangyo Tosho, 1960). CMC of sodium dodecanoyl sarcosinate (SDDS) is 14.4 mM (see the data in the catalog provided by Hampton Research Corp.). CMC of sodium 4-octylbenzene sulfonate is 10.6 mM, CMC of sodium 4-decylbenzene sulfonate is 3.7 mM, and CMC of sodium 4-dodecylbenzene sulfonate is 1.2 mM (see "Kaimenkasseizai Binran (Handbook of Surfactants)," Sangyo Tosho, 1960). CMC of potassium caprylate is 390 mM, CMC of potassium caprate is 98 mM, CMC of potassium laurate is 25.5 mM, CMC of potassium myristate is 6.6 mM, CMC of potassium palmitate is 1.8 mM, and CMC of potassium stearate is 0.45 mM (see "Kaimenkasseizai Binran (Handbook of Surfactants)," Sangyo Tosho, 1960). CMC of sodium cholate is 14 mM (see "Nihon Kagaku Zasshi (Journal of the Chemical Society of Japan)," 90 (5), 463-466, 1969). CMC of sodium deoxycholate is 4.8 mM (see Oleoscience, 1 (12), 1127-1132, 2001). A critical micelle concentration can appropriately be converted into % (w/v). For example, CMC of SDS is 1.04 mM, which is equivalent to 0.03%.

Examples of the nonionic surfactant include a polyoxyethylene alkyl ether, a sorbitan fatty acid ester, an alkyl polyglucoside, a fatty acid diethanol amide, and an alkyl monoglyceryl ether.

(Anionic Surfactants)

Anionic surfactants contain anionic functional groups, such as carboxylic acid, sulfonic acid, sulfuric acid ester salt, or phosphoric acid ester salt, at their hydrophilic heads. Examples of counter cations include sodium, lithium, magnesium, calcium, silver, copper, nickel, zinc, and potassium. Examples of sulfonate-based surfactants include benzene sulfonates modified with linear or branched alkyl sulfuric acid ester salt, cyclic alkyl sulfuric acid ester salt, linear or branched alkyl sulfonate, cyclic alkyl sulfonate, linear or branched alkenyl sulfonate, cyclic alkenyl sulfonate, aryl sulfonate, arylene sulfonate, linear or branched alkyl benzene sulfonate, linear or branched alkenyl benzene sulfonate, aryl, or arylene and α-olefin sulfonates. Examples of surfactants comprising carboxylic acids include fatty acid salt, cholate, and alkyl amino acid salt. Examples of phosphoric-acid-based surfactants include monoalkylphosphoric acid ester salt, and alkylphosphonic acid ester salt. Examples of anionic surfactants include polyoxyethylene alkyl ether sulfate, α-sulfofatty acid ester salt, and alkali metal salt of naturally-occurring fatty acid. Derivatives of such surfactants, such as fluorine-substituted derivatives, are within the scope of surfactants. An alkyl or alkenyl group may be linear, branched, or cyclic. An aryl, alkenyl, aryl, or arylene group may further be substituted or unsubstituted. Substitution can be performed with one or a plurality of halogen atoms or a linear or branched $C_1$ to $C_6$ alkoxy group.

A sulfuric acid ester salt compound is represented by Formula (I):

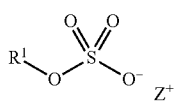
(I)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl, $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, $C_7$ to $C_{20}$ arylene, linear or branched $C_8$ to $C_{18}$ alkyl, $C_3$ to $C_{18}$ cyclic alkyl, linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of alkyl sulfuric acid ester salts include octyl sulfuric acid ester salt, such as sodium octyl sulfate, decyl sulfuric acid ester salt, such as sodium decyl sulfate, dodecyl sulfuric acid ester salt, such as sodium dodecyl sulfate (SDS), tetradecyl sulfuric acid ester salt, such as sodium tetradecyl sulfate, hexadecyl sulfuric acid ester salt, such as sodium hexadecyl sulfate, and octadecyl sulfuric acid ester salt, such as sodium octadecyl sulfate.

A benzene sulfonic acid salt compound is represented by Formula (II):

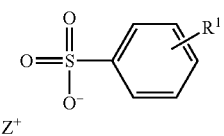
(II)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl, $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, $C_7$ to $C_{20}$ arylene, linear or branched $C_8$ to $C_{18}$ alkyl or $C_3$ to $C_{18}$ cyclic alkyl, linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of alkyl benzene sulfonic acid salt include 4-octyl benzene sulfonic acid salt such as sodium 4-octylbenzene sulfate, 4-decyl benzene sulfonic acid salt such as sodium 4-decylbenzene sulfate, 4-dodecyl benzene sulfonic acid such as sodium 4-dodecylbenzene sulfate, 4-tetradecyl benzene sulfonic acid such as sodium 4-tetradecylbenzene sulfate, 4-hexadecyl benzene sulfonic acid such as sodium 4-hexadecylbenzene sulfate, and 4-octadecyl benzene sulfonic acid salt such as sodium 4-octadecylbenzene sulfate.

An acyl sarcosine acid salt compound is represented by the formula shown below:

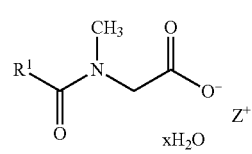
(III)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl or $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene, linear or branched $C_8$ to $C_{18}$ alkyl or $C_3$ to $C_{18}$ cyclic alkyl, or linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of acyl sarcosine acid salt compounds include octoyl sarcosine acid salt such as sodium octoyl sarcosinate, dodecanoyl sarcosine acid salt such as sodium dodecanoyl sarcosinate, and decanoyl sarcosine acid salt such as sodium decanoyl sarcosinate.

A phosphonic acid ester salt compound is represented by Formula (IV):

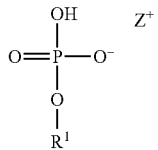

(IV)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl or $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene, linear or branched $C_8$ to $C_{18}$ alkyl or $C_3$ to $C_{18}$ cyclic alkyl, or linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of alkyl phosphonic acid ester salts include octyl phosphonic acid ester salt such as sodium octyl phosphonate, decyl phosphonic acid ester salt such as sodium decyl phosphonate, dodecyl phosphonic acid ester salt such as sodium dodecyl phosphonate, tetradecyl phosphonic acid ester salt such as sodium tetradecyl phosphonate, hexadecyl phosphonic acid ester salt such as sodium hexadecyl phosphonate, and octadecyl phosphonic acid ester salt such as sodium octadecyl phosphonate.

A sulfosuccinic acid salt compound is represented by the formula shown below:

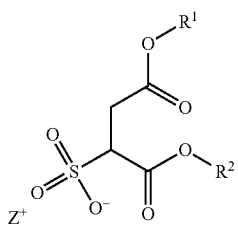

(V)

wherein, $Z^+$ represents a counter ion; and $R^1$ and $R^2$ each independently represent substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl or $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene, linear or branched $C_8$ to $C_{18}$ alkyl or $C_3$ to $C_{18}$ cyclic alkyl, or linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of alkyl sulfosuccinic acid salt compounds include sulfosuccinic acid dioctyl salt such as dioctyl sulfosuccinate sodium salt, sulfosuccinic acid di(2-ethylhexyl) salt such as di(2-ethylhexyl) sulfosuccinate sodium salt, and sulfosuccinic acid dioctadecyl salt such as dioctadecyl sulfosuccinate sodium salt.

A carboxylic acid salt compound is represented by the formula below:

(VI)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl or $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene, linear or branched $C_8$ to $C_{18}$ alkyl or $C_3$ to $C_{18}$ cyclic alkyl, or linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of carboxylic acid salts include fatty acid salts having $C_1$ to $C_{20}$ alkyl. Examples of fatty acid salts include octanoic acid salts such as sodium octanoate and nonanoic acid salt, decanoic acid salt such as sodium decanoate, lauric acid salt such as sodium laurate, myristic acid salt such as sodium myristate, palmitic acid salt such as sodium palmitate, and stearic acid salt such as sodium stearate. Further examples thereof include derivatives of carboxylic acid salts, such as fluorine-substituted derivatives. More specific examples include perfluorooctanoic acid salt such as sodium perfluorooctanoate, perfluorononanoic acid salt such as sodium perfluorononanoate, and cocoyl glutamic acid salt such as sodium cocoyl glutamate ($HOOCCH_2CH_2CH(NH$-$COR)COONa$, wherein R represents $C_{11}$ to $C_{17}$).

A sulfonic acid salt compound is represented by the formula shown below:

(VII)

wherein, $Z^+$ represents a counter ion; and $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene, linear or branched $C_1$ to $C_{20}$ alkyl or $C_3$ to $C_{20}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene, linear or branched $C_8$ to $C_{18}$ alkyl or $C_3$ to $C_{18}$ cyclic alkyl, or linear or branched $C_2$ to $C_{18}$ alkenyl, $C_3$ to $C_{18}$ cyclic alkenyl, $C_6$ to $C_{18}$ aryl, or $C_7$ to $C_{18}$ arylene. Such groups may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of alkyl sulfonic acid salt include octyl sulfonic acid salt such as sodium octyl sulfonate, decyl sulfonic acid salt such as sodium decyl sulfonate, dodecyl sulfonic acid salt such as sodium dodecyl sulfonate, tetradecyl sulfonic acid salt such as sodium tetradecyl sulfonate, hexadecyl sulfonic acid salt such as sodium hexadecyl sulfonate, and octadecyl sulfonic acid sodium salt such as sodium octadecyl sulfonate.

Examples of sulfonic acid salts containing substituents include α-sulfofatty acid methyl ester salts such as sodium α-sulfofatty acid methyl ester (i.e., $CH_3(CH_2)_lCH(SO_3Na)COOCH_3$, wherein n is 8 to 18).

Another example of sulfonic acid salt containing substituents is acyl isethionic acid salt ($R^1CO—O—CH_2—CH_2—SO_3^-$:$Z^+$, wherein $Z^+$ represents a counter ion; and $R^1$ represents $C_1$-$C_{30}$ alkyl, for example, $C_1$-$C_{11}$ alkyl). Examples include stearoyl isethionic acid sodium salt, palmitoyl isethionic acid sodium salt, myristoyl isethionic acid sodium salt, cocoyl isethionic acid sodium salt, lauroyl isethionic acid sodium salt, caproyl isethionic acid sodium salt, and octanoyl isethionic acid sodium salt.

Examples of cholic acid salts include, but are not limited to, cholic acid sodium salt, deoxycholic acid salt such as sodium deoxycholate, glycocholic acid salt such as sodium glycocholate, taurocholic acid salt such as sodium taurocholate, and taurodeoxycholic acid salt such as sodium taurodeoxycholate.

Examples of amino-acid-based surfactants include acylglutamic acid salt, acylmethyl alanine salt, acylglycine salt, and acylmethyl taurine salt. Here in the acyl group of ($R^1CO—$), $R^1$ represents substituted or unsubstituted and linear or branched $C_1$-$C_{30}$ alkyl or cyclic $C_2$-$C_{30}$ alkyl, linear or branched $C_2$ to $C_{30}$ alkenyl, $C_3$ to $C_{30}$ cyclic alkenyl, $C_6$ to $C_{30}$ aryl, or $C_7$ to arylene. Optionally, $R^1$ may be substituted with one or a plurality of halogen atoms or a linear or branched $C_1$ to $C_{30}$ alkoxy or $C_1$ to $C_{30}$ acyloxy group. Examples include, but are not limited to, sodium stearoyl glutamate, sodium palmitoyl glutamate, sodium myristoyl glutamate, sodium cocoyl glutamate, sodium lauroyl glutamate, sodium caproyl glutamate, sodium palmitoyl methyltaurate, sodium myristoyl methyltaurate, sodium cocoyl methyltaurate, sodium caproyl methyltaurate, sodium cocoyl methyltaurate, magnesium cocoyl methyltaurate, sodium lauroyl methyltaurate, sodium stearolyl methyltaurate, sodium myristoyl methyltaurate, sodium palmitoyl methyltaurate, sodium myristoyl methylalanine, sodium cocoyl methylalanine, sodium lauroyl methylalanine, sodium caproyl methylalanine, sodium palmitoyl glycine, sodium myristoyl glycine, sodium cocoyl glycine, sodium lauroyl glycine, sodium caproyl glycine, and potassium cocoyl glycine. The above encompass equivalents having different types of counter ions.

Examples of anionic surfactants include derivatives of the compounds described above. For example, derivatives of compound resulting from substitution of hydrogen with fluorine and derivatives comprising amino acids are within the scope of the surfactants in the present invention.

Examples of fluorine-substituted derivatives include compounds resulting from substitution of hydrogen with fluorine in the compounds described above. Examples thereof include, but are not limited to, perfluorooctanesulfonic acids, perfluorooctanoic acid, perfluorononanic acid, perfluorobutansulfonic acid, and perfluorononanic acid.

Examples of derivatives comprising amino acids include, but are not limited to, acylated amino acid salts, such as N-acetyl glutamic acid salt, N-acetyl alanine acid salt, N-acetyl glycine acid salt, N-acetyl aspartic acid salt, N-acetyl glutamic acid salt, N-alkyl aminopropionic acid salt.

(Cationic Surfactants)

Examples of cationic surfactants include alkyltrimethylammonium salts, dialkyldimethylammonium salts, alkylbenzyldimethylammonium salts, pyridinium salts such as an alkylpyridinium salt, phosphonium salts such as an alkylphosphonium salt, imidazolium salts such as an alkylimidazolium salt, and isoquinolinium salts such as an alkylisoquinolinium salt.

Examples of cationic surfactants include a quaternary ammonium salt, a pyridinium salt, and a phosphonium salt represented by the following general formulae:

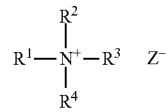

wherein, $R^1$ to $R^4$, which may be the same or different, each represent substituted or unsubstituted and linear or branched $C_1$ to $C_{30}$ alkyl, such as $C_1$ to $C_{20}$ alkyl or $C_3$ to $C_{30}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene; and $Z^-$ represents a monovalent anion. $R^1$ to $R^4$ may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group:

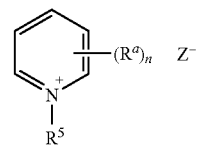

wherein, $R^5$ represents substituted or unsubstituted and linear or branched $C_1$ to $C_{30}$ alkyl, such as $C_1$ to $C_{20}$ alkyl, $R^a$s, which may be the same or different, each represent a hydrogen atom or substituted or unsubstituted $C_1$ to $C_{30}$ alkyl, such as $C_1$ to $C_{20}$ alkyl, $C_3$ to $C_{30}$ cyclic alkyl, $C_2$ to $C_{20}$ alkenyl, $C_3$ to $C_{20}$ cyclic alkenyl, $C_6$ to $C_{20}$ aryl, or $C_7$ to $C_{20}$ arylene; n is an integer of 1 to 5; and $Z^-$ represents a monovalent anion. $R^5$ and $R^a$ may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group:

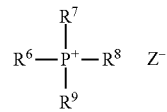

wherein, $R^6$ to $R^9$, which may be the same or different, each represent substituted or unsubstituted and linear or branched $C_1$ to $C_{30}$ alkyl, such as $C_1$ to $C_{20}$ alkyl, $C_3$ to $C_{30}$ cyclic alkyl, linear or branched $C_2$ to $C_{20}$ alkenyl, $C_3$ to $C_{20}$ cyclic alkenyl, $C_6$ to $C_{20}$ aryl, or $C_7$ to $C_{20}$ arylene; and $Z^-$ represents a monovalent anion. $R^6$ to $R^9$ may optionally be substituted with one or a plurality of halogen atoms or a linear or branched $C_1$ to $C_{30}$ alkoxy group, $C_1$ to $C_{30}$ acyloxy group, or $C_2$ to $C_{30}$ alkoxycarbonyl group.

Examples of the quaternary ammonium salt include octyltrimethylammonium chloride and bromide, decyltrimethylammonium chloride and bromide, dodecyltrimethylammonium chloride and bromide, tetradecyltrimethylammonium chloride and bromide, hexadecyltrimethylammonium chloride and bromide, octadecyltrimethylammonium chloride and bromide, eicosyltrimethylammonium chloride and bromide, benzyldodecyldimethylammonium chloride and bromide, benzyltetradecyldimethylammonium chloride and bromide, benzylcetyldimethylammonium chloride and bromide, dioctyldimethylammonium chloride and bromide.

Examples of the pyridinium salt include 1-decylpyridinium chloride and bromide, 1-dodecylpyridinium chloride, 1-dodecylpyridinium bromide, 1-tetradecylpyridinium chloride and bromide, 1-hexadecylpyridinium chloride and bromide, N-cetyl-2-methylpyridinium chloride and bromide, N-cetyl-3-methylpyridinium chloride and bromide, N-cetyl-4-methylpyridinium chloride and bromide, 1-octadecylpyridinium chloride and bromide, 1-eicosylpyridinium chloride and bromide.

Examples of the phosphonium salt include tetraethylphosphonium chloride and bromide, tributylmethylphosphonium chloride and bromide and iodide, tetrabutylphosphonium chloride and bromide, tetra-n-octylphosphonium chloride and bromide, tributyldodecylphosphonium chloride and bromide, tributylhexadecylphosphonium chloride and bromide, methyltriphenylphosphonium chloride and bromide and iodide, tetraphenylphosphonium chloride and bromide.

Anion $Z^-$ to be paired up with a cationic surfactant can be, for example, $Cl^-$, $Br^-$, or $I^-$. Examples of the amphoteric surfactant include an alkyl dimethyl amine oxide and alkylcarboxybetaine.

(Kit Containing the Amadoriase of the Present Invention and Surfactant)

The present invention provides a kit for measuring glycated hemoglobin containing an amadoriase and a surfactant. The surfactant can be a nonionic or ionic surfactant. The amadoriase and the surfactant can be contained as a mixture or as separate components in a kit. In general, when the amadoriase and the surfactant are contained as a mixture in the kit, it is preferable that the surfactant be included at a concentration which does not inactivate the amadoriase. When the amadoriase and the surfactant are contained as separate components in the kit, a stock solution containing the surfactant at a concentration higher than the final concentration for measurement may be used. The stock solution is appropriately diluted to prepare the solution for measurement. A solution containing a surfactant can be prepared by dissolving a surfactant in water, pure water, buffer, or an organic solvent. For example, a surfactant with low water solubility can first be dissolved in an organic solvent such as dimethyl sulfoxide (DMSO), and the resultant can then be added to the solution for measurement.

The kit containing the amadoriase of the present invention and a surfactant can further contain reagents for measuring a glycated substrate such as αFVH, a protease or peptidase for cleaving the glycation substrate such as αFVH, and other known components, such as a stabilizer and a buffer. Techniques used in kits for measuring αFVH can be appropriately used for producing the kit containing the amadoriase of the present invention and a surfactant. More specifically, the present invention provides a method for producing a kit containing an amadoriase and a surfactant comprising the step of preparing an appropriate amadoriase and a surfactant. In this case, the amadoriase and the surfactant can be prepared as a mixture or as separate components. When the amadoriase and surfactant are provided as separate components in the kit, they can be mixed immediately before measurement of a glycated substrate such as αFVH.

The amadoriase included in the kit of the present invention preferably exhibits a residual activity (%) of preferably 10% or higher, 15% or higher, 20% or higher, 30% or higher, 40% or higher, 50% or higher, 60% or higher, 70% or higher, 80% or higher, 90% or higher, 95% or higher or 99% or higher 5 minutes after the surfactant solution included in the kit and adjusted to the final concentration is added, compared with the amadoriase to which the surfactant solution is not added. Residual activity will be explained below.

The amadoriase included in the kit of the present invention preferably has a final concentration of 110 µg/ml or lower (for example, 100 µg/ml or lower, 90 µg/ml or lower, 80 µg/ml or lower, 70 µg/ml or lower, 60 µg/ml or lower, or 50 µg/ml or lower) per surfactant of 0.032% (w/v) at the time of measurement. The surfactant included in the kit has a final concentration of 0.003% (w/v) or higher (for example, 0.0032% (w/v) or higher, 0.0035% (w/v) or higher, 0.004% (w/v) or higher, 0.0045% (w/v) or higher, 0.005% (w/v) or higher, 0.006% or higher, 0.007% (w/v) or higher, 0.008% (w/v) or higher, 0.009% (w/v) or higher, 0.01% (w/v) or higher, 0.015% (w/v) or higher, 0.02% (w/v) or higher, 0.025% (w/v) or higher, 0.03% (w/v) or higher, 0.035% (w/v) or higher, 0.036% (w/v) or higher, 0.04% (w/v) or higher, 0.045% (w/v) or higher, 0.05% (w/v) or higher, 0.06% (w/v) or higher, 0.07% (w/v) or higher, 0.08% (w/v) or higher, 0.09% (w/v) or higher, 0.1% (w/v) or higher, 0.11% (w/v) or higher, 0.12% (w/v) or higher, 0.13% (w/v) or higher, 0.14% (w/v) or higher, 0.15% (w/v) or higher, 0.16% (w/v) or higher, 0.17% (w/v) or higher, 0.18% (w/v) or higher, 0.19% (w/v) or higher, 0.2% (w/v) or higher, 0.21% (w/v) or higher, 0.22% (w/v) or higher, 0.23% (w/v) or higher, 0.24% (w/v) or higher, 0.25% (w/v) or higher, 0.26% (w/v) or higher, 0.27% (w/v) or higher, 0.28% (w/v) or higher, 0.29% (w/v) or higher, 0.3% (w/v) or higher, 0.35% (w/v) or higher, 0.4% (w/v) or higher, 0.45% (w/v) or higher, 0.5% (w/v) or higher, 0.6% (w/v) or higher, 0.7% (w/v) or higher, 00.8% (w/v) or higher, 0.9% (w/v) or higher, 1.0% (w/v) or higher, 1.05% (w/v) or higher, 1.1% (w/v) or higher, 1.15% (w/v) or higher, 1.2% (w/v) or higher, 1.25% (w/v) or higher, 1.3% (w/v) or higher, 1.35% (w/v) or higher, 1.4% (w/v) or higher, 1.45% (w/v) or higher, 1.5% (w/v) or higher, 1.6% (w/v) or higher, 1.7% (w/v) or higher, 1.8% (w/v) or higher, 1.9% (w/v) or higher, 2.0% (w/v) or higher, 2.1% (w/v) or higher, 2.2% (w/v) or higher, 2.3% (w/v) or higher, 2.4% (w/v) or higher, 2.5% (w/v) or higher, or 3.0% (w/v) or higher) at the time of measurement. The final concentration at the time of measurement herein refers to the concentration of the component finally diluted and used for measuring glycated hemoglobin. Accordingly, the kit may contain a stock solution having a concentration higher than the final concentration at the time of measurement.

In one embodiment, the amadoriase included in the kit of the present invention may be an amadoriase having the amino acid sequence as shown in SEQ ID No: 1, SEQ ID NO: 94, or SEQ ID NO: 110 or a variant prepared based thereon exhibiting an improvement in surfactant tolerance. The variant can have an amino acid sequence having sequence identity of, for example, 70% or higher, 75% or higher, 80% or higher, 85% or higher, 90% or higher, 95% or higher, 97% or higher, or 99% or higher, with SEQ ID NO: 1, SEQ ID NO: 94, or SEQ ID NO: 110 or an amino acid sequence derived from the amino acid sequence as shown in SEQ ID NO: 1 via modification, variation, deletion, substitution, addition, and/or insertion of one to several amino acids.

The amadoriase included in the kit of the present invention can be a natural amadoriase derived from the genera *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, *Penicillium*, *Fusarium*, *Achaetomiella*, *Achaetomium*, *Thielavia*, *Chaetomium*, *Gelasinospora*, *Microascus*, *Leptosphaeria*, *Ophiobolus*,

*Pleospora, Coniochaetidium, Pichia, Corynebacterium, Agrobacterium*, and *Arthrobacter* or a variant thereof. Such variant may comprise one or more amino acid substitutions as described above.

A person skilled in the art can adequately examine whether or not an amadoriase of interest can be used for the kit of the present invention, more specifically, whether or not an amadoriase has desired surfactant tolerance, in accordance with the disclosure of the present invention.

In one embodiment, the kit of the present invention comprises an amadoriase and sodium cholate. The amadoriase included in the kit may be a naturally-occurring amadoriase, a known amadoriase, or an amadoriase comprising the variation according to the present invention. The amadoriase and sodium cholate can be included in the kit in the form of a mixture or as separate components. According to one embodiment, the kit of the present invention can contain sodium cholate at a concentration of 0.1% (w/v) or higher, 0.2% (w/v) or higher, 0.5% (w/v) or higher, 1.0% (w/v) or higher to 2.0% (w/v) or lower, 1.8% (w/v) or lower, or 1.5% (w/v) or lower, for example, 0.1 to 2.0% (w/v) or 0.5 to 1.5% (w/v) in the amadoriase solution or at a final concentration thereof at the time of measurement of glycated hemoglobin.

In one embodiment, the kit of the present invention comprises an amadoriase and sodium deoxycholate. The amadoriase included in the kit may be a naturally-occurring amadoriase, a known amadoriase, or an amadoriase comprising the variation according to the present invention. The amadoriase and sodium deoxycholate can be included in the kit in the form of a mixture or as separate components. According to one embodiment, sodium deoxycholate can be included in the kit of the present invention such that the concentration thereof is 0.1% (w/v) or higher, 0.2% (w/v) or higher, 0.3% (w/v) or higher, 0.4% (w/v) or higher, 0.5% (w/v) or higher, 1.0% (w/v) or higher to 2.0% (w/v) or lower, 1.8% (w/v) or lower, or 1.5% (w/v) or lower, such as 0.1 to 2.0% (w/v), 0.2 to 2.0% (w/v), or 0.5 to 1.5% (w/v) in the amadoriase solution, or the final concentration thereof at the time of measurement of glycated hemoglobin.

A person skilled in the art can adequately determine the concentration of sodium cholate or sodium deoxycholate used for the kit comprising the amadoriase in accordance with the disclosure of the present invention.

(Buffer)

To the kit or composition of the present invention, a buffer or a buffer solution having a buffer capacity within the range of pH 5.0 to pH 10.0, preferably pH 6.0 to pH 8.0 where an amadoriase is not inactivated, may appropriately be added. The term "buffer" used herein refers to one or more buffers, unless otherwise specified.

Examples of the buffer (buffer solution) that can be used in the kit (composition) of the present invention include a borate buffer containing boric acid and/or a salt thereof, a Tris-hydrochloride buffer, a phosphate buffer containing phosphoric acid and/or a salt thereof such as a potassium phosphate buffer or a sodium phosphate buffer, an organic acid buffer containing an organic acid buffer and/or a salt thereof such as a tricarboxylate buffer containing tricarboxylic acid and/or a salt thereof, a citrate buffer containing citric acid and/or a salt thereof, a monocarboxylate buffer containing a monocarboxylic acid and/or a salt thereof such as an acetate buffer containing an acetic acid and/or a salt thereof, and buffers such as Good's buffers.

The buffer can be used at a concentration appropriate for the kit or composition of the present invention. In general, the amount of buffer to be added in the kit or composition of the present invention can be calculated based on the final concentration in a measurement solution. In one embodiment, the final concentration of the buffer in a measurement solution is the concentration at which a pH change that can occur in the measurement solution is sufficiently buffered. The final concentration of the buffer can for example be 1 mM or higher, 5 mM or higher, 10 mM or higher, 20 mM or higher, or 50 mM or higher to 1M or lower, 500 mM or lower, 400 mM or lower, 300 mM or lower, 200 mM or lower, or 100 mM or lower. For example, it can be 1 mM to 1M, 5 mM to 500 mM, 10 mM to 300 mM, or 50 mM to 100 mM.

(Improvement in Surfactant Tolerance of the Amadoriase of the Present Invention)

The amadoriase of the present invention obtained by the aforementioned means has a mutation in its amino acid sequence by e.g., genetic modification. As a result, the amadoriase has enhanced (improved) surfactant tolerance, compared with the amadoriase before modification. More specifically, the residual activity (%) of the modified amadoriase is improved 5 minutes after a predetermined surfactant treatment, for example, after 0.1 to 0.2%, such as 0.15 to 0.2% (w/v) SDDS or 0.03%, 0.036%, or 0.04% SDS is added at 30° C. According to another embodiment, the modified amadoriase according to the present invention exhibits the residual activity (%) that is improved 5 minutes after a predetermined surfactant treatment described in terms of the method of activity measurement and the method of surfactant tolerance evaluation herein, for example, after sodium octyl sulfate at a final concentration of 1.0 to 2.0% (w/v), sodium tetradecyl sulfate at a final concentration of 0.0032 to 0.0064% (w/v), sodium octadecyl sulfate at a final concentration of 0.002 to 0.0032% (w/v), sodium 4-dodecylbenzene sulfonate at a final concentration of 0.005 to 0.001% (w/v), sodium cholate at a final concentration of 1.0 to 2.0% (w/v), or sodium deoxycholate at a final concentration of 0.60 to 1.2% (w/v) is added at 30° C. The residual activity (%) herein refers to the ratio (%) of activity after surfactant treatment relative to the activity before the surfactant treatment (regarded as 100). Incidentally, when the concentration of a surfactant in the specification is expressed by percentage, unless otherwise specified the percentage indicates % (w/v).

The degree of improvement of the residual activity (%) of a modified amadoriase of the present invention is not limited; however, for example, the present invention encompasses a modified amadoriase having a residual activity (%) of preferably 5% or higher, 10% or higher, 15% or higher, 20% or higher, 25% or higher, 30% or higher, 35% or higher, 40% or higher, 50% or higher, 60% or higher, 70% or higher, 80% or higher, 90% or higher, 95% or higher, or 99% or higher after the variation of the present invention has been introduced. For example, a modified amadoriase exhibiting 20% of the residual activity after it is treated with an anionic surfactant is within the scope of the present invention.

According to one embodiment, the residual activity (%) of the modified amadoriase according to the present invention can exceed 100% after the surfactant treatment. Accordingly, a modified amadoriase resulting from introduction of the variation of the present invention that has the residual activity of 100% or more, 105% or more, 110% or more, 115% or more, 120% or more, 125% or more, 130% or more, 135% or more, 140% or more, 145% or more, or 150% or more after the surfactant treatment is within the scope of the present invention. As for variants having a residual activity (%) which exceeds 100% after surfactant treatment as a result of introducing the variation according to the present invention, it can be said that such variation (mutation) not only improves surfactant tolerance but also enhances amadoriase activity. Such variations also fall under variations which enhance tolerance to surfactants. That is, variations of the present invention which improve surfactant tolerance encompass variations that enhance amadoriase activity in the presence of a surfactant. A variation that enhances amadoriase activity in the presence of a surfactant refers to a variation that can produce an amadoriase that has a residual activity (%) exceeding 100% after surfactant treatment.

When an amadoriase that does not comprise the variation of the present invention and amadoriase that does comprise the variation of the present invention are subjected to a surfactant treatment and the numerical values of residual activity (%) are compared, a modified amadoriase having a residual activity improved by, for example, 2% or more, 3% or more, 4% or more, 5% or more, 6% or more, 7% or more, 8% or more, 9% or more, 10% or more, 15% or more, 20% or more, 25% or more, 30% or more, 35% or more, 40% or more, 50% or more, 60% or more, 70% or more, 80% or more, 90% or more, 95% or more, 99% or more, 100% or more, 110% or more, 120% or more, 130% or more, or 140% or more is within the scope of the present invention. If the amadoriase before introduction of the variation has a residual activity of 18% after treatment with an anionic surfactant and the modified amadoriase has a residual activity of 20% after introduction of the variation, for example, this can be understood as an improvement of residual activity by 2% in terms of comparison between the residual activity values (%) and such modified amadoriase is within the scope of the present invention. If the residual activity after treatment with an anionic surfactant for the modified amadoriase after introduction of the variation is 153% and for the amadoriase before introduction of the variation is 9%, it can be said that the residual activity is improved by 144%, in terms of comparison between the residual activity values (%), and such modified amadoriase is within the scope of the present invention.

According to one embodiment, surfactant tolerance of the amadoriase according to the present invention is evaluated in terms of the residual activity (%) measured after sodium dodecyl sulfate (SDS) is added to a final concentration of 0.03% and the resultant is allowed to stand at 30° C. for 5 minutes. In this case, the residual activity measured without the addition of SDS is designated as 100%. When the residual activity of a certain amadoriase is 20% under such conditions, such situation is expressed herein with the phrase "the residual activity (%) measured after sodium dodecyl sulfate is added thereto to a final concentration of 0.03% and the resultant is allowed to stand at 30° C. for 5 minutes is 20% in comparison with the case where no sodium dodecyl sulfate is added (100%)."

Further, when the residual activity of the amadoriase comprising the variation of the present invention is found to have improved by 2.5% as a result of comparison of the residual activity after the surfactant treatment between the amadoriase that does not comprise the variation of the present invention and the amadoriase that comprises the variation of the present invention, such situation is expressed herein with the phrase "the residual activity (%) measured after sodium dodecyl sulfate is added to a final concentration of 0.03% and the resultant is allowed to stand at 30° C. for 5 minutes is increased by 2.5%."

According to one embodiment, when an amadoriase before introduction of the variation of the present invention is subjected to surfactant treatment, the amadoriase may completely lose its activity. In such cases, in order to evaluate improvement of the residual activity of an amadoriase (%) of the present invention to which the variation of the present invention is introduced, an amadoriase which does not completely lose its activity even by the surfactant treatment may be used as a reference (standard), and the residual activity of the amadoriase serving as a reference after the surfactant treatment may be compared with the residual activity of an amadoriase having a variation introduced therein after the surfactant treatment.

Relative evaluation results may differ depending not only upon temperature conditions during measurement but also upon the degree of surfactant tolerance of the amadoriase before introduction of a mutation. Therefore, it may be difficult to evaluate the absolute surfactant tolerance of variants based only on whether numerical values of the residual activity (%) and the residual activity ratio are larger or smaller. However, it is possible to absolutely evaluate the surfactant tolerance of variants by following the conditions of the examples of the present invention. Further, in order to readily select the amadoriase of the present invention, a surfactant treatment condition under which the residual activity of an amadoriase (%) before introduction of a mutation is calculated to be sufficiently low may be selected, so that the degree of improvement in the residual activity (%) and that in the residual activity ratio tend in general to be calculated high.

For example, when the amadoriase according to the present invention produced by the *Escherichia coli* JM109 (pKK223-3-CFP-T7/K80R) strain that is within the scope of the present invention is mixed with 0.03% SDS and subjected to a treatment at 30° C. for 5 minutes, the residual activity of amadoriase before introduction of the variation of the present invention (i.e., CFP-T7) is 18.9%, whereas, the residual activity of Amadoriase 4 after introduction of the variation of the present invention is 46.2% and stability against SDS was enhanced. Further, when the amadoriase according to the present invention produced by the *Escherichia coli* JM109 (pKK223-3-CFP-T7/M71L) strain is mixed with 0.03% SDS and subjected to a treatment at 30° C. for 5 minutes, the residual activity of amadoriase before introduction of the variation of the present invention (i.e., CFP-T7) is 18.9%, whereas, the residual activity of Amadoriase 3 after introduction of the variation of the present invention is 34.0% and stability against SDS was enhanced. Thus, the amadoriase according to the present invention with improved in anionic surfactant tolerance is significantly improved in terms of storage property in, for example, enzyme-containing products and further protease degradation efficiency of HbA1c is improved, and measurement sensitivity is improved and, therefore, such amadoriase is stable even when a strong surfactant is used and thus very advantageous from an industrial perspective.

According to one embodiment, the present invention provides a modified amadoriase that enables measurement of HbA1c in the presence of 0.03% or 0.036% SDS. Such modified amadoriase comprises an amino acid sequence in which, when aligned with the amino acid sequence as shown in SEQ ID NO: 1, one or more amino acids at positions corresponding to the positions selected from the group consisting of positions 80, 71, 175, 172, 279, 12, 9, 77, 30, 28, 13, 3, 4, 286, 204, 338, 44, 340, and 194 in the amino acid sequence as shown in SEQ ID NO: 1 have been substituted. Substitution amino acids are as exemplified above. To the modified amadoriase and amadoriase in which amino acids at the positions described above are not substituted, when SDS is added to a final concentration of 0.03% or 0.036%, and the residual activity values (%)

thereof are measured at 30° C. 5 minutes later and compared, the modified amadoriase of the present invention has residual activity that is improved by, for example, 2% or more, 3% or more, 4% or more, 5% or more, 6% or more, 8% or more, 10% or more, 15% or more, 20% or more, 25% or more, 30% or more, 35% or more, 40% or more, 45% or more, or 50% or more, compared with the amadoriase in which amino acids at the positions described above are not substituted.

According to one embodiment, the present invention provides a modified amadoriase that enables measurement of HbA1c in the presence of 0.1% or 0.15% SDDS. Such modified amadoriase comprises an amino acid sequence in which, when aligned with the amino acid sequence as shown in SEQ ID NO: 1, one or more amino acids at positions corresponding to the positions selected from the group consisting of positions 80, 71, 175, 172, 279, 12, 9, 77, 30, 28, 13, 3, 4, 286, 204, 338, 44, 340, and 194 in the amino acid sequence as shown in SEQ ID NO: 1 have been substituted. Substitution amino acids are as exemplified above. To the modified amadoriase and amadoriase in which amino acids at the positions described above are not substituted, when SDDS is added to a final concentration of 0.1% or 0.15% and the residual activity values (%) thereof are measured at 30° C. 5 minutes later and compared, the modified amadoriase of the present invention has residual activity that is improved by, for example, 2% or more, 3% or more, 4% or more, 5% or more, 6% or more, 8% or more, 10% or more, 15% or more, 20% or more, 25% or more, or 30% or more, compared with the amadoriase in which amino acids at the positions described above are not substituted.

Such modified amadoriases according to the present invention retain activity in the presence of a surfactant that denatures HbA1c, such as 0.03% or 0.036% SDS or 0.1% or 0.15% SDDS. Thus, such amadoriases can be used for measurement of HbA1c.

(High-Throughput Screening)

An amadoriase can further be subjected to high-throughput screening, so as to obtain a functional amadoriase variant. For example, a library of a transformant or transductant comprising the transgenic amadoriase gene may be prepared and the resulting library may then be subjected to high-throughput screening using a microtiter plate. Alternatively, the library may be subjected to ultrahigh-throughput screening based on droplet microfluidics. For example, a combinatorial library of mutant genes encoding variants can be constructed and a large population of mutant amadoriases can be subjected to screening by means of phage display (e.g., Chem. Rev., 105 (11): 4056-72, 2005), yeast display (e.g., Comb. Chem. High Throughput Screen., 2008; 11(2): 127-34), or bacterial display (e.g., Curr. Opin. Struct. Biol., 17: 474-80, 2007). A reference may be made to Agresti et al, "Ultrahigh-throughput screening in drop-based microfluidics for directed evolution," Proceedings of the National Academy of Sciences, 107 (9): 4004-4009, March, 2010. The description thereof concerning the technique for ultrahigh-throughput screening, which may be employed for screening of an amadoriase variant is incorporated herein by reference. For example, a library can be constructed by error-prone PCR. Alternatively, a mutation may be introduced into a target, which is a position described herein or position corresponding thereto, via saturation mutagenesis, so as to construct a library. Adequate cells, such as electrocompetent EBY-100 cells, can be transformed using a library and approximately $10^7$ variants can be obtained. Yeast cells transformed with the library can then be subjected to cell sorting. A polydimethoxylsiloxane (PDMS) microfluidic device prepared via standard soft-lithography may be used. Monodisperse droplets can be prepared using a flow-focusing device. The prepared droplets separately comprising variants can be applied to an adequate sorting device. Cells can be selected based on the presence or absence of amadoriase activity in the presence of a surfactant. Mutagenesis and selection may be repeated a plurality of times.

(Method for Measuring Amadoriase Activity)

Amadoriase activity can be measured via various techniques. An example of a method for measuring amadoriase activity that is employed in the present invention is described below.

(Method for Measuring Amadoriase Activity)

Examples of primary methods for measuring enzyme activity of an amadoriase according to the present invention include a method in which the amount of hydrogen peroxide generated upon an enzyme reaction is measured and a method in which the amount of oxygen consumed by an enzyme reaction is measured. An example of a method for measuring the amount of hydrogen peroxide is described below.

For measurement of the amadoriase activity of the present invention, unless indicated otherwise, fructosyl valine is used as the substrate. Regarding enzyme titer, the amount of enzyme capable of generating 1 µmol of hydrogen peroxide per minute can be defined as 1 U, when measurement is carried out using fructosyl valine as the substrate. A glycated amino acid, such as fructosyl valine, and a glycated peptide, such as fructosyl-valyl-histidine, can be synthesized and purified using the method of Sakaue et al. (JP 2001-95598 A). It should be noted that the description above is merely provided for convenience of description of the method of measurement and that substrate specificity of the amadoriase used in the present invention is not limited to fructosyl valine.

A: Preparation of Reagents (1) Reagent 1: POD-4-AA Solution

Peroxidase (4.0 kU, manufactured by Kikkoman Corporation) and 100 mg of 4-aminoantipyrine (manufactured by Tokyo Chemical Industry Co., Ltd.) are dissolved in a 0.1 M potassium phosphate buffer (pH 7.0), and the volume of the solution is fixed to 1 liter.

(2) Reagent 2: TOOS Solution

TOOS (500 mg, N-ethyl-N-(2-hydroxy-3-sulfopropyl)-m-toluidine sodium, manufactured by Dojindo Laboratories) is dissolved in ion-exchange water, and the volume of the solution is fixed to 100 ml.

(3) Reagent 3: Substrate Solution (150 mM; Final Concentration: 5 mM)

Fructosyl valine (417 mg) is dissolved in ion-exchange water, and the volume of the solution is fixed to 10 ml.

B: Method for Measurement

Reagent 1 (2.7 ml), 100 µl of Reagent 2, and 100 µl of Reagent 3 are mixed, and the mixture is preliminarily heated at 37° C. for 5 minutes. Subsequently, 100 µl of the enzyme solution is added, the resultant is thoroughly mixed, and the absorbance at 555 nm is then measured using a spectrophotometer (U-3010, manufactured by Hitachi High-Technologies). The measurement value is the change in absorbance at 555 nm per minute from 1 minute to 3 minutes after the initiation of measurement. A control solution is prepared in the manner as described above, with the proviso that 100 µl of ion-exchange water is added instead of 100 µl of Reagent 3. The number of micromoles of hydrogen peroxide generated per minute at 37° C. is calculated using the equation shown below in terms of the unit of activity (U) in the enzyme solution.

Activity (U/ml)={(ΔAs−ΔA0)×3.0×df}/(39.2×0.5×0.1)

ΔAs: the change in absorbance of the reaction solution per minute
ΔA0: the change in absorbance of the control solution per minute
39.2: the millimole absorbance index of the quinoneimine dye generated by the reaction (mM$^{-1}$·cm$^{-1}$)
0.5: the number of moles of the quinoneimine dye generated by 1 mol of hydrogen peroxide
df: the dilution factor (Method for Measurement of Surfactant Tolerance)

An amadoriase crude enzyme solution or an amadoriase purified sample is diluted with a 30 mM MES/21 mM Tris buffer solution (pH 6.5) so as to have a concentration of about 1.0 U/ml. To this, SDS (e.g., SDS manufactured by Wako Pure Chemical Industries Ltd.) is added so as to obtain a final concentration 0.03% (w/v) or 0.04%. The resultant mixture is heated at 30° C. for 5 minutes. After heating, the mixture is diluted 2-fold with a 10 mM phosphate buffer (pH 7.0) containing 0.15% BSA to prepare a sample. The enzyme activities of the sample before and after surfactant treatment are measured by the method described in Section B above. The ratio of activity of the sample after the surfactant treatment relative to the activity of the sample before the surfactant treatment (regarded as 100), i.e., the residual activity (%), is determined. Surfactant tolerance can thus be evaluated.

The present invention will be described more specifically below with reference to the Examples. However, these Examples are not intended in any way to limit the technical scope of the present invention.

Example 1

(Surfactant Tolerance Enhancing Variations (Mutations))
(1) Preparation of DNA of Recombinant Plasmid pKK223-3-CFP-T7

A strain of *E. coli* JM109 comprising the recombinant plasmid comprising the CFP-T7 gene (SEQ ID NO: 2) (pKK223-3-CFP-T7) (WO 2007/125779) was inoculated into 2.5 ml of LB-amp media (1% (w/v) bactotrypton, 0.5% (w/v) peptone, 0.5% (w/v) NaCl, and 50 μg/ml ampicillin) and shake culture was conducted at 37° C. for 20 hours to obtain a culture product.

The culture product was centrifuged at 7,000 rpm for 5 minutes to collect the cells. Subsequently, the recombinant plasmid pKK223-3-CFP-T7 was extracted and purified therefrom using QIAGEN tip-100 (manufactured by QIA-GEN), and 2.5 μl of DNA of the recombinant plasmid pKK223-3-CFP-T7 was obtained.

(2) Site-Directed Modification Procedure of DNA of Recombinant Plasmid pKK223-3-CFP-T7

PCR was carried out under conditions described below using DNA of the recombinant plasmid pKK223-3-CFP-T7 as the template, synthetic oligonucleotides as shown in SEQ ID NOs: 14 and 15, and KOD-Plus- (Toyobo Co., Ltd.).

That is, 5 μl of 10×KOD-Plus-buffer, 5 μl of a dNTPs mixture in which each dNTP was adjusted at 2 mM, 2 μl of a 25 mM MgSO$_4$ solution, 50 ng of DNA of pKK223-3-CFP-T7 as the template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was subjected to electrophoresis on 1.0% agarose gel, and specific amplification a DNA of about 6,000 bp was confirmed. The DNA obtained in such a manner was treated with a restriction enzyme DpnI (manufactured by New England Biolabs), the remaining template DNA was cleaved, strains of *E. coli* JM109 were transformed, and the transformants were then spread on LB-amp agar media. The grown colonies were inoculated into LB-amp media and shake-cultured therein, and plasmid DNAs were isolated in the same manner as in (1) above. The nucleotide sequences of was DNA encoding the amadoriase in the plasmid was determined using a multi-capillary DNA analysis system (Applied Biosystems 3130xl Genetic Analyzer; manufactured by Life Technologies). Thus, the recombinant plasmid encoding the modified amadoriase resulting from substitution of arginine at position 9 with threonine in the amino acid sequence as shown in SEQ ID NO: 1 was obtained (pKK223-3-CFP-T7-R9T).

In the same manner, PCR was carried out using synthetic oligonucleotides as shown in SEQ ID NOs: 16 and 17 to obtain a recombinant plasmid encoding a modified amadoriase resulting from substitution of valine at position 12 with isoleucine in the amino acid sequence as shown in SEQ ID NO: 1 (pKK223-3-CFP-T7-V12I).

In the same manner, PCR was carried out using synthetic oligonucleotides as shown in SEQ ID NOs: 61 and 62 to obtain a recombinant plasmid encoding a modified amadoriase resulting from substitution of valine at position 12 with leucine in the amino acid sequence as shown in SEQ ID NO: 1 (pKK223-3-CFP-T7-V12L).

In the same manner, PCR was carried out using synthetic oligonucleotides as shown in SEQ ID NOs: 18 and 19 to obtain a recombinant plasmid encoding a modified amadoriase resulting from substitution of methionine at position 71 with leucine in the amino acid sequence as shown in SEQ ID NO: 1 (pKK223-3-CFP-T7-M71L).

In the same manner, PCR was carried out using synthetic oligonucleotides as shown in SEQ ID NOs: 71 and 72 to obtain a recombinant plasmid encoding a modified amadoriase resulting from substitution of methionine at position 71 with isoleucine in the amino acid sequence as shown in SEQ ID NO: 1 (pKK223-3-CFP-T7-M71I).

In the same manner, PCR was carried out using synthetic oligonucleotides as shown in SEQ ID NOs: 71 and 73 to obtain a recombinant plasmid encoding a modified amadoriase resulting from substitution of methionine at position 71 with alanine in the amino acid sequence as shown in SEQ ID NO: 1 (pKK223-3-CFP-T7-M71A).

In the same manner, PCR was carried out using synthetic oligonucleotides as shown in SEQ ID NOs: 71 and 74 to obtain a recombinant plasmid encoding a modified amadoriase resulting from substitution of methionine at position 71 with valine in the amino acid sequence as shown in SEQ ID NO: 1 (pKK223-3-CFP-T7-M71V).

In the same manner, PCR was carried out using synthetic oligonucleotides as shown in SEQ ID NOs: 71 and 75 to obtain a recombinant plasmid encoding a modified amadoriase resulting from substitution of methionine at position 71 with cysteine in the amino acid sequence as shown in SEQ ID NO: 1 (pKK223-3-CFP-T7-M71C).

In the same manner, PCR was carried out using synthetic oligonucleotides as shown in SEQ ID NOs: 20 and 21 to obtain a recombinant plasmid encoding a modified amadoriase resulting from substitution of lysine at position 80 with arginine in the amino acid sequence as shown in SEQ ID NO: 1 (pKK223-3-CFP-T7-K80R).

In the same manner, PCR was carried out using synthetic oligonucleotides as shown in SEQ ID NOs: 81 and 82 to obtain a recombinant plasmid encoding a modified amadoriase resulting from substitution of lysine at position 80 with asparagine in the amino acid sequence as shown in SEQ ID NO: 1 (pKK223-3-CFP-T7-K80N).

In the same manner, PCR was carried out using synthetic oligonucleotides as shown in SEQ ID NOs: 81 and 83 to obtain a recombinant plasmid encoding a modified amadoriase resulting from substitution of lysine at position 80 with glutamine in the amino acid sequence as shown in SEQ ID NO: 1 (pKK223-3-CFP-T7-K80Q).

In the same manner, PCR was carried out using synthetic oligonucleotides as shown in SEQ ID NOs: 81 and 84 to obtain a recombinant plasmid encoding a modified amadoriase resulting from substitution of lysine at position 80 with histidine in the amino acid sequence as shown in SEQ ID NO: 1 (pKK223-3-CFP-T7-K80H).

In the same manner, PCR was carried out using synthetic oligonucleotides as shown in SEQ ID NOs: 22 and 23 to obtain a recombinant plasmid encoding a modified amadoriase resulting from substitution of phenylalanine at position 172 with glutamic acid in the amino acid sequence as shown in SEQ ID NO: 1 (pKK223-3-CFP-T7-F172E).

In the same manner, PCR was carried out using synthetic oligonucleotides as shown in SEQ ID NOs: 85 and 86 to obtain a recombinant plasmid encoding a modified amadoriase resulting from substitution of phenylalanine at position 172 with aspartic acid in the amino acid sequence as shown in SEQ ID NO: 1 (pKK223-3-CFP-T7-F172D).

In the same manner, PCR was carried out using synthetic oligonucleotides as shown in SEQ ID NOs: 85 and 87 to obtain a recombinant plasmid encoding a modified amadoriase resulting from substitution of phenylalanine at position 172 with tyrosine in the amino acid sequence as shown in SEQ ID NO: 1 (pKK223-3-CFP-T7-F172Y).

In the same manner, PCR was carried out using synthetic oligonucleotides as shown in SEQ ID NOs: 85 and 88 to obtain a recombinant plasmid encoding a modified amadoriase resulting from substitution of phenylalanine at position 172 with glutamine in the amino acid sequence as shown in SEQ ID NO: 1 (pKK223-3-CFP-T7-F172Q).

In the same manner, PCR was carried out using synthetic oligonucleotides as shown in SEQ ID NOs: 24 and 25 to obtain a recombinant plasmid encoding a modified amadoriase resulting from substitution of glutamic acid at position 175 with arginine in the amino acid sequence as shown in SEQ ID NO: 1 (pKK223-3-CFP-T7-E175R).

In the same manner, PCR was carried out using synthetic oligonucleotides as shown in SEQ ID NOs: 89 and 90 to obtain a recombinant plasmid encoding a modified amadoriase resulting from substitution of glutamic acid at position 175 with lysine in the amino acid sequence as shown in SEQ ID NO: 1 (pKK223-3-CFP-T7-E175K).

In the same manner, PCR was carried out using synthetic oligonucleotides as shown in SEQ ID NOs: 89 and 91 to obtain a recombinant plasmid encoding a modified amadoriase resulting from substitution of glutamic acid at position 175 with histidine in the amino acid sequence as shown in SEQ ID NO: 1 (pKK223-3-CFP-T7-E175H).

In the same manner, PCR was carried out using synthetic oligonucleotides as shown in SEQ ID NOs: 26 and 27 to obtain a recombinant plasmid encoding a modified amadoriase resulting from substitution of valine at position 279 with isoleucine in the amino acid sequence as shown in SEQ ID NO: 1 (pKK223-3-CFP-T7-V279I).

In the same manner, PCR was carried out using synthetic oligonucleotides as shown in SEQ ID NOs: 92 and 93 to obtain a recombinant plasmid encoding a modified amadoriase resulting from substitution of valine at position 279 with cysteine in the amino acid sequence as shown in SEQ ID NO: 1 (pKK223-3-CFP-T7-V279C).

In the same manner, PCR was carried out using synthetic oligonucleotides as shown in SEQ ID NOs: 28 and 29 to obtain a recombinant plasmid encoding a modified amadoriase resulting from substitution of valine at position 28 with leucine in the amino acid sequence as shown in SEQ ID NO: 1 (pKK223-3-CFP-T7-V28L).

In the same manner, PCR was carried out using synthetic oligonucleotides as shown in SEQ ID NOs: 65 and 66 to obtain a recombinant plasmid encoding a modified amadoriase resulting from substitution of valine at position 28 with isoleucine in the amino acid sequence as shown in SEQ ID NO: 1 (pKK223-3-CFP-T7-V28I).

In the same manner, PCR was carried out using synthetic oligonucleotides as shown in SEQ ID NOs: 65 and 67 to obtain a recombinant plasmid encoding a modified amadoriase resulting from substitution of valine at position 28 with methionine in the amino acid sequence as shown in SEQ ID NO: 1 (pKK223-3-CFP-T7-V28M).

In the same manner, PCR was carried out using synthetic oligonucleotides as shown in SEQ ID NOs: 30 and 31 to obtain a recombinant plasmid encoding a modified amadoriase resulting from substitution of serine at position 30 with alanine in the amino acid sequence as shown in SEQ ID NO: 1 (pKK223-3-CFP-T7-S30A).

In the same manner, PCR was carried out using synthetic oligonucleotides as shown in SEQ ID NOs: 68 and 69 to obtain a recombinant plasmid encoding a modified amadoriase resulting from substitution of serine at position 30 with threonine in the amino acid sequence as shown in SEQ ID NO: 1 (pKK223-3-CFP-T7-S30T).

In the same manner, PCR was carried out using synthetic oligonucleotides as shown in SEQ ID NOs: 68 and 70 to obtain a recombinant plasmid encoding a modified amadoriase resulting from substitution of serine at position 30 with valine in the amino acid sequence as shown in SEQ ID NO: 1 (pKK223-3-CFP-T7-S30V).

In the same manner, PCR was carried out using synthetic oligonucleotides as shown in SEQ ID NOs: 32 and 33 to obtain a recombinant plasmid encoding a modified amadoriase resulting from substitution of glutamine at position 77 with aspartic acid in the amino acid sequence as shown in SEQ ID NO: 1 (pKK223-3-CFP-T7-Q77D).

In the same manner, PCR was carried out using synthetic oligonucleotides as shown in SEQ ID NOs: 76 and 77 to obtain a recombinant plasmid encoding a modified amadoriase resulting from substitution of glutamine at position 77 with glutamic acid in the amino acid sequence as shown in SEQ ID NO: 1 (pKK223-3-CFP-T7-Q77E).

In the same manner, PCR was carried out using synthetic oligonucleotides as shown in SEQ ID NOs: 76 and 79 to obtain a recombinant plasmid encoding a modified amadoriase resulting from substitution of glutamine at position 77 with lysine in the amino acid sequence as shown in SEQ ID NO: 1 (pKK223-3-CFP-T7-Q77K).

In the same manner, PCR was carried out using synthetic oligonucleotides as shown in SEQ ID NOs: 76 and 80 to obtain a recombinant plasmid encoding a modified amadoriase resulting from substitution of glutamine at position 77 with asparagine in the amino acid sequence as shown in SEQ ID NO: 1 (pKK223-3-CFP-T7-Q77N).

In the same manner, PCR was carried out using synthetic oligonucleotides as shown in SEQ ID NOs: 63 and 64 to obtain a recombinant plasmid encoding a modified amadoriase resulting from substitution of valine at position 13 with leucine in the amino acid sequence as shown in SEQ ID NO: 1 (pKK223-3-CFP-T7-V13L).

The nucleotide sequences of DNAs encoding amadoriases in the plasmids described above were determined in the same manner as described above, so as to confirm the introduction of the variation.

the above measurement method for surfactant tolerance. The results are shown in Table 1. It was confirmed that there was no change in the activity value when the warmed sample was diluted 2-fold with a BSA solution and then subjected to activity measurement again 30 minutes later. In Table 1, CFP-T7 indicates an amadoriase derived from the strain *Escherichia coli* JM109 (pKK223-3-CFP-T7). In this example, CFP-T7, which is an amadoriase derived from the strain *E. coli* JM109 (pKK223-3-CFP-T7), is employed as the original enzyme for source of mutation and, therefore, descriptions concerning "Amino acid mutations" in the table do not include various points of mutations that have already been introduced into CFP-T7.

TABLE 1

| Amadoriase | Template plasmid | Mutation | Oligonucleotide SEQ ID NO. | Residual activity after treatment (%) 0.15% SDDS | 0.03% SDS |
|---|---|---|---|---|---|
| CFP-T7 | None | None | None | 73.0 | 18.9 |
| Amadoriase 1 | pKK223-3-CFP-T7 | R9T | 14, 15 | 82.7 | 40.2 |
| CFP-T7-R9N | | R9N | 118, 119 | 90.0 | 7.3 |
| CFP-T7-R9Q | | R9Q | 118, 120 | 91.7 | 11.9 |
| Amadoriase 2 | | V12I | 16, 17 | 79.9 | 41.0 |
| CFP-T7-V12L | | V12L | 61, 62 | 93.1 | 49.6 |
| Amadoriase 3 | | M71L | 18, 19 | 83.8 | 34.0 |
| CFP-T7-M71I | | M71I | 71, 72 | 141.1 | 18.9 |
| CFP-T7-M71A | | M71A | 71, 73 | 96.2 | 63.2 |
| CFP-T7-M71V | | M71V | 71, 74 | 105.0 | 35.5 |
| CFP-T7-M71C | | M71C | 71, 75 | 111.5 | 27.2 |
| Amadoriase 4 | | K80R | 20, 21 | 89.9 | 46.2 |
| CFP-T7-K80N | | K80N | 81, 82 | 101.3 | 49.5 |
| CFP-T7-K80Q | | K80Q | 81, 83 | 96.1 | 30.3 |
| CFP-T7-K80H | | K80H | 81, 84 | 91.9 | 7.7 |
| Amadoriase 5 | | F172E | 22, 23 | 79.1 | 27.5 |
| CFP-T7-F172D | | F172D | 85, 86 | 102.3 | 20.1 |
| CFP-T7-F172Y | | F172Y | 85, 87 | 94.6 | 10.5 |
| CFP-T7-F172Q | | F172Q | 85, 88 | 95.5 | 15.8 |
| Amadoriase 6 | | E175R | 24, 25 | 77.0 | 30.8 |
| CFP-T7-E175K | | E175K | 89, 90 | 104.5 | 41.3 |
| CFP-T7-E175H | | E175H | 89, 91 | 102.0 | 17.0 |
| Amadoriase 7 | | V279I | 26, 27 | 79.4 | 29.3 |
| CFP-T7-V279C | | V279C | 92, 93 | 92.6 | 9.1 |
| Amadoriase 8 | pKK223-3-CFP-T7 | V28L | 28, 29 | 57.1 | 14.9 |
| CFP-T7-V28I | | V28I | 65, 66 | 111.8 | 26.9 |
| CFP-T7-V28M | | V28M | 65, 67 | 127.4 | 32.8 |
| Amadoriase 9 | | S30A | 30, 31 | 70.9 | 17.5 |
| CFP-T7-S30T | | S30T | 68, 69 | 92.8 | 21.1 |
| CFP-T7-S30V | | S30V | 68, 70 | 105.4 | 34.0 |
| Amadoriase 10 | | Q77D | 32, 33 | 64.5 | 21.4 |
| CFP-T7-Q77E | | Q77E | 76, 77 | 96.5 | 16.3 |
| CFP-T7-Q77K | | Q77K | 76, 79 | 80.7 | 10.0 |
| CFP-T7-Q77N | | Q77N | 76, 80 | 93.1 | 9.4 |
| CFP-T7-V13L | | V13L | 63, 64 | 115.6 | 48.8 |

(3) Production of Various Modified Amadoriases

Strains of *E. coli* JM109 carrying the recombinant plasmids obtained in the manner described above were cultured in 3 ml of LB-amp media supplemented with 0.1 mM IPTG at 30° C. for 16 hours. Thereafter, the resulting cultured strains were washed with a 0.01 M phosphate buffer (pH 7.0), the washed strains were ultrasonically disrupted, and the resultants were centrifuged at 15,000 rpm for 10 minutes to prepare 1.5 ml each of crude enzyme solutions.

(4) Evaluation of Surfactant Tolerance of Various Modified Amadoriases

Using each crude enzyme solution thus prepared as a sample, the final concentration of SDS or SDDS (manufactured by Tokyo Kasei Kogyo Co., Ltd.) was set at 0.03% or 0.15%, respectively, so as to evaluate the surfactant tolerance of each of the modified amadoriases in accordance with As shown in Table 1, the residual activity of CFP-T7 was 73.0% after treatment with 0.15% SDDS, and it was 18.9% after treatment with 0.03% SDS under the conditions of the present example. In the 7 variants obtained by site-directed mutagenesis, specifically, amadoriases in each of which arginine at position 9 in CFP-T7 is substituted with threonine, valine at position 12 with isoleucine, methionine at position 71 with leucine, lysine at position 80 with arginine, phenylalanine at position 172 with glutamic acid, glutamic acid at position 175 with arginine, and valine at position 279 with isoleucine, in contrast, the residual activity was enhanced by 4% to 16.9% after treatment with SDDS, and it was enhanced by 8.6% to 27.3% after treatment with SDS, compared with CFP-T7. Further, the amadoriase resulting from substitution of glutamine at position 77 with aspartic acid in CFP-T7 exhibited an improvement by 2.5% after treatment with SDS, compared with CFP-T7. Further, the amadoriase resulting from substitution of valine at position 12 with leucine, methionine at position 71 with alanine, valine, or cysteine, lysine at position 80 with asparagine or glutamine, phenylalanine at position 172 with aspartic acid, glutamic acid at position 175 with lysine, valine at position 28 with isoleucine or methionine, serine at position 30 with threonine or valine, or valine at position 13 with leucine in CFP-T7 exhibited an improvement in the residual activity in the presence of SDS, compared with CFP-T7. Accordingly, the points of variations indicated above were found to be the points of variations aimed at enhanced surfactant tolerance of amadoriases.

As a result of substitution of position 9 with threonine, asparagine, or glutamine, satisfactory results were obtained. It was thus considered that similar results could be obtained via substitution of position 9 with serine, which is also an amino acid comprising a polar side chain.

As a result of substitution of position 12 with isoleucine or leucine, satisfactory results were obtained. It was thus considered that similar results could be obtained via substitution of position 12 with methionine or cysteine, which is also an amino acid with a larger molecular weight than valine.

As a result of substitution of position 71 with leucine, isoleucine, alanine, valine, or cysteine, satisfactory results were obtained. It was thus considered that similar results could be obtained via substitution of position 71 with glycine, which is also an amino acid with a smaller molecular weight than methionine.

Satisfactory results were obtained as a result of substitution of position 80 with arginine, asparagine, glutamine, or histidine.

Satisfactory results were obtained as a result of substitution of position 172 with glutamic acid, aspartic acid, tyrosine, or glutamine.

Satisfactory results were obtained as a result of substitution of position 175 with arginine, lysine, or histidine.

Satisfactory results were obtained as a result of substitution of position 279 with isoleucine or cysteine. Accordingly, it was considered that similar results could be obtained via substitution of position 279 with methionine, phenylalanine, tyrosine, or tryptophan, which is also an amino acid with a larger molecular weight than valine.

Satisfactory results were obtained as a result of substitution of position 28 with isoleucine or methionine. Accordingly, it was considered that similar results could be obtained via substitution of position 28 with alanine, which is also an amino acid having a hydrophobic side chain, or cysteine, which is also an amino acid having a larger molecular weight than valine.

Satisfactory results were obtained as a result of substitution of position 30 with threonine or valine. Accordingly, it was considered that similar results could be obtained via substitution of position 30 with leucine or isoleucine, which is also an amino acid comprising a hydrophobic side chain.

Satisfactory results were obtained as a result of substitution of position 77 with aspartic acid, glutamic acid, lysine, or asparagine.

Satisfactory results were obtained as a result of substitution of position 13 with leucine. Accordingly, it was considered that similar results could be obtained via substitution of position 13 with isoleucine, cysteine, or methionine, which is also an amino acid having a larger molecular weight than valine.

The points of variations according to the present invention are effective as single variations. In addition, such points of variations may be used in combination with various types of variations that have already been known. Further, use of the variations of the present invention in combination with each other is expected to contribute to preparation of variants that are practically advantageous.

Example 2

(Accumulation of Anionic Surfactant Tolerance Enhancing Variations)

Based on the findings concerning variations aimed at enhanced surfactant tolerance obtained in Example 1, the present inventors attempted accumulation of surfactant tolerance enhancing variations (mutations) by preparing a multiple variant for the purpose of obtaining an amadoriase having further increased surfactant tolerance.

In the same manner as in Example 1, a recombinant plasmid encoding a modified amadoriase resulting from substitution of phenylalanine at position 43 with tyrosine and glutamic acid at position 44 with proline (pKK223-3-CFP-T7-F43Y/E44P) was obtained using DNA of pKK223-3-CFP-T7 as the template and synthetic oligonucleotides as shown in SEQ ID NOs: 34 and 35.

Further, in the same manner as described above, a recombinant plasmid encoding a modified amadoriase resulting from substitution of phenylalanine at position 43 with tyrosine, glutamic acid at position 44 with proline, and histidine at position 53 with asparagine (pKK223-3-CFP-T7-F43Y/E44P/H53N) was obtained using DNA of pKK223-3-CFP-T7-F43Y/E44P as the template and synthetic oligonucleotides as shown in SEQ ID NOs: 36 and 37.

Subsequently, a recombinant plasmid encoding a modified amadoriase resulting from substitution of glutamic acid at position 44 with proline and glutamic acid at position 340 with proline (pKK223-3-CFP-T7-E44P/E340P) was obtained using DNA of pKK223-3-CFP-T7-E44P, which is a plasmid expressing CFP-T7-E44P as an amadoriase with improved cationic surfactant tolerance disclosed in PCT/JP2014/071036 (WO 2015/020200), as the template and synthetic oligonucleotides as shown in SEQ ID NOs: 38 and 39.

Further, in the same manner as described above, a recombinant plasmid encoding a modified amadoriase resulting from substitution of phenylalanine at position 172 with glutamic acid and glutamic acid at position 175 with arginine (pKK223-3-CFP-T7-F172E/E175R) was obtained using DNA of pKK223-3-CFP-T7-F172E as the template and synthetic oligonucleotides as shown in SEQ ID NOs: 25 and 40.

Further, in the same manner as described above, a recombinant plasmid encoding a modified amadoriase resulting from substitution of valine at position 28 with leucine and serine at position 30 with alanine (pKK223-3-CFP-T7-V28L/S30A) was obtained using DNA of pKK223-3-CFP-T7-V28L as the template and synthetic oligonucleotides as shown in SEQ ID NOs: 31 and 41.

Further, in the same manner as described above, a recombinant plasmid encoding a modified amadoriase resulting from substitution of methionine at position 71 with leucine, glutamine at position 77 with aspartic acid, and lysine at position 80 with arginine (pKK223-3-CFP-T7-M71L/Q77D/K80R) was obtained using DNA of pKK223-3-CFP-T7-M71L as the template and synthetic oligonucleotides as shown in SEQ ID NOs: 42 and 43.

Incidentally, 43Y, 53N, and 184D are variations that enhance heat stability of enzymes (WO 2013/100006). 44P and 340P are variations that enhance cationic surfactant tolerance (PCT/JP2014/071036, i.e., WO 2015/020200).

The multiple variants were produced in the same manner as in Example 1, the resulting crude enzyme solutions were designated as samples, and surfactant tolerance of various modified amadoriases was evaluated in accordance with the method for evaluation of surfactant tolerance described in (4) above in the same manner as in Example 1. The results are shown in Table 2. It was confirmed that there was no change in the activity value when the warmed sample was diluted 2-fold with a BSA solution and then subjected to activity measurement again 30 minutes later.

TABLE 2

| Amadoriase | Mutation | Residual activity after treatment (%) | |
|---|---|---|---|
| | | 0.15% SDDS | 0.03% SDS |
| CFP-T7 | None | 73.0 | 18.9 |
| Amadoriase 12 | F43Y/E44P | 94.9 | 55.1 |
| Amadoriase 13 | F43Y/E44P/H53N | 98.8 | 70.2 |
| Amadoriase 14 | E44P/E340P | 76.9 | 20.3 |
| Amadoriase 15 | F172E/E175R | 88.2 | 51.2 |
| Amadoriase 16 | V28L/S30A | 81.6 | 37.3 |
| Amadoriase 17 | M71L/Q77D/K80R | 91.6 | 56.3 |

As shown in Table 2, the residual activity of CFP-T7 was 73.0% after treatment with 0.15% SDDS, and it was 18.9% after treatment with 0.03% SDS under the conditions of the present example. In comparison therewith, the double variant and the triple variant of the present invention exhibited an improvement in the residual activity after they were treated with anionic surfactants.

More specifically, Amadoriase 15 into which the 172E/175R variation had been introduced had a residual activity of 51.2% after treatment with 0.03% SDS, which was improved to a significant extent, compared with the residual activity of CFP-T7 which was 18.9%.

As a result of introduction of the 172E/175R variation, satisfactory results were obtained. Accordingly, it was considered that similar results could be obtained via substitution of position 172 of the amadoriase with glutamic acid or aspartic acid, which is an acidic amino acid, simultaneously with substitution of position 175 with arginine, histidine, or lysine, which is a basic amino acid.

Amadoriase 16 into which the 28L/30A variation had been introduced had a residual activity of 37.5% after treatment with 0.03% SDS, which was improved to a significant extent, compared with the residual activity of CFP-T7 which was 18.9%.

As a result of introduction of the 28L/30A variation, satisfactory results were obtained. Accordingly, it was considered that similar results could be obtained via substitution of position 28 of the amadoriase with leucine, isoleucine, methionine, cysteine, or alanine, which is a hydrophobic amino acid, simultaneously with substitution of position 30 with alanine, valine, leucine, or isoleucine, which has a smaller molecular weight than serine, or threonine, which is an amino acid structurally similar to serine. In particular, a combination of substitution of position 28 with leucine or isoleucine simultaneously with substitution of position 30 with alanine can also provide similar effects.

Further, Amadoriase 17 into which the 71L/77D/80R variation had been introduced had a residual activity of 56.3% after treatment with 0.03% SDS, which was improved to a significant extent, compared with the residual activity of CFP-T7 which was 18.9%.

Accordingly, the combination of such variations of the present invention was found to enhance surfactant tolerance of the amadoriase under stronger denaturation conditions.

Satisfactory results were obtained as a result of the 71L/77D/80R variation. It was thus considered that similar results could be attained through simultaneous substitution of position 71 of the amadoriase with leucine, isoleucine, alanine, glycine, valine, or cysteine, which is an amino acid with a smaller molecular weight than methionine, position 77 with aspartic acid or glutamic acid, which is an acidic amino acid, and position 80 with arginine or histidine, which is a basic amino acid.

Further, the variations 43Y and 53N, which were reported to enhance heat stability of the enzyme, and the variations 44P and 340P, which enhance cationic surfactant tolerance, were introduced in combination as shown in Table 2, and exhibited increase in residual activity.

Since the effects of the combination of the variations according to the present invention were verified, accumulation of such combinations is expected to further enhance tolerance to surfactants.

(Further Accumulation of Variations)

Subsequently, a recombinant plasmid encoding a modified amadoriase resulting from substitution of arginine at position 9 with threonine, valine at position 12 with isoleucine, and valine at position 13 with isoleucine (pKK223-3-CFP-T7-R9T/V12I/V13I) was obtained using DNA of pKK223-3-CFP-T7-R9T as the template and synthetic oligonucleotides as shown in SEQ ID NOs: 44 and 45.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, and valine at position 13 with isoleucine (pKK223-3-CFP-T7-S3T/N4P/R9T/V12I/V13I) was obtained using DNA of pKK223-3-CFP-T7-R9T/V12I/V13I as the template and synthetic oligonucleotides as shown in SEQ ID NOs: 46 and 47.

In the same manner as described above, a recombinant plasmid encoding a modified amadoriase resulting from substitution of arginine at position 9 with threonine, valine at position 12 with isoleucine, valine at position 13 with isoleucine, valine at position 28 with leucine, and serine at position 30 with alanine (pKK223-3-CFP-T7-R9T/V12I/V13I/V28L/S30A) was obtained using DNA of pKK223-3-CFP-T7-R9T/V12I/V13I as the template and synthetic oligonucleotides as shown in SEQ ID NOs: 31 and 41.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, and lysine at position 80 with arginine (pKK223-3-CFP-T7-S3T/N4P/R9T/V12I/V13I/V28L/S30A/F43Y/E44P/H53N/M71L/Q77D/K80R) was obtained using DNA of pKK223-3-CFP-T7-F43Y/E44P/H53N as the template and synthetic oligonucleotides as shown in SEQ ID NOs: 18, 19, 31, 41, 42, 43, 44, 45, 46, and 47.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, and serine at position 154 with aspartic acid (pKK223-3-CFP-T7-S3T/N4P/R9T/V12I/V13I/V28L/S30A/F43Y/E44P/H53N/M71L/Q77D/K80R/S154D) was obtained using DNA of pKK223-3-CFP-T7-S3T/N4P/R9T/V12I/V13I/V28L/S30A/F43Y/E44P/H53N/M71L/Q77D/K80R as the template and synthetic oligonucleotides as shown in SEQ ID NOs: 48 and 49.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, serine at position 154 with aspartic acid, valine at position 257 with cysteine, and asparagine at position 262 with histidine (pKK223-3-CFP-T7-S3T/N4P/R9T/V12I/V13I/V28L/S30A/F43Y/E44P/H53N/M71L/Q77D/K80R/S154D/V257C/N262H) was obtained using DNA of pKK223-3-CFP-T7-S3T/N4P/R9T/V12I/V13I/V28L/S30A/F43Y/E44P/H53N/M71L/Q77D/K80R/S154D as the template and synthetic oligonucleotides as shown in SEQ ID NOs: 50 and 51.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, serine at position 154 with aspartic acid, phenylalanine at position 172 with glutamic acid, glutamic acid at position 175 with arginine, valine at position 257 with cysteine, and asparagine at position 262 with histidine (pKK223-3-CFP-T7-S3T/N4P/R9T/V12I/V13I/V28L/S30A/F43Y/E44P/H53N/M71L/Q77D/K80R/S154D/V257C/N262H/F172E/E175R) was obtained using DNA of pKK223-3-CFP-T7-S3T/N4P/R9T/V12I/V13I/V28L/S30A/F43Y/E44P/H53N/M71L/Q77D/K80R/S154D/V257C/N262H as the template and synthetic oligonucleotides as shown in SEQ ID NOs: 25 and 40.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, and serine at position 154 with aspartic acid, phenylalanine at position 172 with glutamic acid, glutamic acid at position 175 with arginine, valine at position 257 with cysteine, and asparagine at position 262 with histidine and deletion of 3 amino acid residues from the carboxyl terminus (ΔPTS1) (pKK223-3-CFP-T7-S3T/N4P/R9T/V12I/V13I/V28L/S30A/F43Y/E44P/H53N/M71L/Q77D/K80R/S154D/V257C/N262H/F172E/E175R/ΔPTS1) was obtained using DNA of pKK223-3-CFP-T7-S3T/N4P/R9T/V12I/V13I/V28L/S30A/F43Y/E44P/H53N/M71L/Q77D/K80R/S154D/V257C/N262H/F172E/E175R as the template and synthetic oligonucleotides as shown in SEQ ID NOs: 52 and 53.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, glutamic acid at position 98 with alanine, serine at position 154 with aspartic acid, phenylalanine at position 172 with glutamic acid, glutamic acid at position 175 with arginine, valine at position 257 with cysteine, asparagine at position 262 with histidine and deletion of 3 amino acid residues from the carboxyl terminus (ΔPTS1) (pKK223-3-CFP-T7-S3T/N4P/R9T/V12I/V13I/V28L/S30A/F43Y/E44P/H53N/M71L/Q77D/K80R/S154D/V257C/N262H/F172E/E175R/ΔPTS1/E98A) was obtained using DNA of pKK223-3-CFP-T7-S3T/N4P/R9T/V12I/V13I/V28L/S30A/F43Y/E44P/H53N/M71L/Q77D/K80R/S154D/V257C/N262H/F172E/E175R/ΔPTS1 as the template and synthetic oligonucleotides as shown in SEQ ID NOs: 54 and 55.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, histidine at position 53 with asparagine, methionine at position 71 with leucine, glutamine at position 77 with aspartic acid, lysine at position 80 with arginine, glutamic acid at position 98 with alanine, serine at position 154 with aspartic acid, phenylalanine at position 172 with glutamic acid, glutamic acid at position 175 with arginine, valine at position 257 with cysteine, asparagine at position 262 with histidine, and phenylalanine at position 286 with tyrosine and deletion of 3 amino acid residues from the carboxyl terminus (ΔPTS1) (pKK223-3-CFP-T7-S3T/N4P/R9T/V12I/V13I/V28L/S30A/F43Y/E44P/H53N/M71L/Q77D/K80R/S154D/V257C/N262H/F172E/E175R/ΔPTS1/E98A/F286Y) was obtained using DNA of pKK223-3-CFP-T7-S3T/N4P/R9T/V12I/V13I/V28L/S30A/F43Y/E44P/H53N/M71L/Q77D/K80R/S154D/V257C/N262H/F172E/E175R/ΔPTS1/E98A as the template and synthetic oligonucleotides as shown in SEQ ID NOs: 121 and 122. An amadoriase encoded by such plasmid may be referred to as "amadoriase 25-F286Y."

Subsequently, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, phenylalanine at position 43 with tyrosine, glutamic acid at position 44 with proline, glutamic acid at position 98 with alanine, serine at position 154 with aspartic acid, glycine at position 184 with aspartic acid, valine at position 257 with cysteine, asparagine at position 262 with histidine, and glutamic acid at position 340 with proline and deletion of 3 amino acid residues from the carboxyl terminus (ΔPTS1) (pKK223-3-CFP-T7-S3T/N4P/R9T/V12I/V13I/F43Y/E44P/E98A/S154D/G184D/V257C/N262H/E340P/ΔPTS1) was obtained using DNA of pKK223-3-CFP-D4, which is a plasmid expressing CFP-D4 as an amadoriase with improved cationic surfactant tolerance disclosed in PCT/JP2014/071036 (WO 2015/020200) (i.e., CFP-T7-F43Y/E44P/E98A/G184D/V257C/N262H/E340P/ΔPTS1), as the template and synthetic oligonucleotides as shown in SEQ ID NOs: 44, 45, 46, 47, 48, and 49.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, phenylalanine at position 43 with tyrosine, glutamic acid at position 44 with proline, glutamic acid at position 98 with alanine, serine at position 154 with aspartic acid, phenylalanine at position 172 with glutamic acid, glutamic acid at position 175 with arginine, glycine at position 184 with aspartic acid, valine at position 257 with cysteine, asparagine at position 262 with histidine, and glutamic acid at position 340 with proline and deletion of 3 amino acid residues from the carboxyl terminus (ΔPTS1) (pKK223-3-CFP-T7-S3T/N4P/R9T/V12I/V13I/F43Y/E44P/E98A/S154D/G184D/V257C/N262H/E340P/ΔPTS1/F172E/E175R) was obtained using DNA of pKK223-3-CFP-T7-S3T/N4P/R9T/V12I/V13I/F43Y/E44P/E98A/S154D/G184D/V257C/N262H/E340P/ΔPTS1 as the template and synthetic oligonucleotides as shown in SEQ ID NOs: 25 and 40.

In the same manner as described above, a recombinant plasmid encoding a modified amadoriase resulting from substitution of serine at position 3 with threonine, asparagine at position 4 with proline, arginine at position 9 with threonine, valine at position 12 with isoleucine, valine at position 13 with isoleucine, valine at position 28 with leucine, serine at position 30 with alanine, phenylalanine at position 43 with tyrosine, glutamic acid at position 44 with proline, glutamic acid at position 98 with alanine, serine at position 154 with aspartic acid, phenylalanine at position 172 with glutamic acid, glutamic acid at position 175 with arginine, glycine at position 184 with aspartic acid, valine at position 257 with cysteine, asparagine at position 262 with histidine, and glutamic acid at position 340 with proline and deletion of 3 amino acid residues from the carboxyl terminus (ΔPTS1) (pKK223-3-CFP-T7-S3T/N4P/R9T/V12I/V13I/F43Y/E44P/E98A/S154D/G184D/V257C/N262H/E340P/ΔPTS1/F172E/E175R/V28L/S30A) was obtained using DNA of pKK223-3-CFP-T7-S3T/N4P/R9T/V12I/V13I/F43Y/E44P/E98A/S154D/G184D/V257C/N262H/E340P/ΔPTS1/F172E/E175R as the template and synthetic oligonucleotides as shown in SEQ ID NOs: 31 and 41.

98A and 154D are variations that are reported to modify substrate specificity (WO 2012/018094). 257C and 262H are variations that are reported to enhance tolerance to cationic surfactants and to SDS (PCT/JP2014/071036, that is, WO 2015/020200). ΔPTS1 is a deletion of 3 amino acid residues from the carboxyl terminus that is reported to enhance heat stability (WO 2013/100006).

The resulting crude enzyme solutions were designated as samples, and surfactant tolerance of various modified amadoriases was evaluated in accordance with the method for evaluation of surfactant tolerance described in (4) above while surfactant treatment was carried out under more stringent conditions using a 0.04% SDS mixture. The results are shown in Table 2. It was confirmed that there was no change in the activity value when the warmed sample was diluted 2-fold with a BSA solution and then subjected to activity measurement again 30 minutes later.

TABLE 3

| Amadoriase | Mutation | Residual activity after SDS treatment (%) |
| --- | --- | --- |
| CFP-T7 | None | 4.8 |
| Amadoriase 12 | F43Y/E44P/H53N | 8.2 |
| Amadoriase 17 | M71L/Q77D/K80R | 7.1 |
| Amadoriase 18 | S3T/N4P/R9T/V12I/V13I | 8.9 |
| Amadoriase 19 | R9T/V12I/V13I/V28L/S30A | 5.9 |
| Amadoriase 20 | F43Y/E44P/H53N/S3T/N4P/R9T/V12I/V13I/V28L/S30A/M71L/Q77D/K80R | 22.8 |
| Amadoriase 21 | F43Y/E44P/H53N/S3T/N4P/R9T/V12I/V13I/V28L/S30A/M71L/Q77D/K80R/S154D | 26.8 |
| Amadoriase 22 | F43Y/E44P/H53N/S3T/N4P/R9T/V12I/V13I/V28L/S30A/M71L/Q77D/K80R/S154D/V257C/N262H | 47.9 |
| Amadoriase 23 | F43Y/E44P/H53N/S3T/N4P/R9T/V12I/V13I/V28L/S30A/M71L/Q77D/K80R/S154D/V257C/N262H/F172E/E175R | 55.2 |
| Amadoriase 24 | F43Y/E44P/H53N/S3T/N4P/R9T/V12I/V13I/V28L/S30A/M71L/Q77D/K80R/S154D/V257C/N262H/F172E/E175R/ΔPTS1 | 74.3 |
| Amadoriase 25 | F43Y/E44P/H53N/S3T/N4P/R9T/V12I/V13I/V28L/S30A/M71L/Q77D/K80R/S154D/V257C/N262H/F172E/E175R/ΔPTS1/E98A | 84.5 |
| Amadoriase 26 | E98A/G184D/ΔPTS1/F43Y/E44P/S154D/V257C/N262H/E340P/S3T/N4P/R9T/V12I/V13I | 28.9 |
| Amadoriase 27 | E98A/G184D/ΔPTS1/F43Y/E44P/S154D/V257C/N262H/E340P/S3T/N4P/R9T/V12I/V13I/F172E/E175R | 40.6 |
| Amadoriase 28 | E98A/G184D/ΔPTS1/F43Y/E44P/S154D/V257C/N262H/E340P/S3T/N4P/R9T/V12I/V13I/F172E/E175R/V28L/S30A | 81.9 |

As shown in Table 3, the residual activity of CFP-T7 was as low as 4.8% under the conditions of the present example. Under such severe conditions involving the use of anionic surfactants, conventional amadoriases were found to lose most activity.

In contrast, various multiple variants, prepared by employing various single variations verified in Example 1 in combination, exhibited significant improvement in residual activity levels.

Specifically, Amadoriase 17 into which the 71L/77D/80R variations were introduced had a residual activity of 7.1%, which was enhanced compared to that of CFP-T7 (i.e., 4.8%). Amadoriase 20 into which the 71L/77D/80R variations, the 28L/30A variations, and the 3T/4P/R9T/12I/13I variations were introduced had a residual activity of 22.8%, which was significantly enhanced from that of CFP-T7, and such residual activity was significantly improved, compared with Amadoriases 12, 17, 18, and 19 before introduction of the variation.

Amadoriase 23 into which the 172E/175R variations were introduced had a residual activity of 55.2%, which was enhanced compared to that of Amadoriase 22 before introduction of the variation (i.e., 47.9%). Amadoriase 27 into which the 172E/175R variations were introduced had a residual activity of 40.6%, which was enhanced compared to that of Amadoriase 26 before introduction of the variation (i.e., 28.9%).

Amadoriase 19 into which the 28L/30A variations were introduced had a residual activity of 5.9%, which was enhanced compared to that of CFP-T7 (i.e., 4.8%). Amadoriase 28 into which the 28L/30A variations were introduced had a residual activity of 81.9%, which was significantly enhanced from that of Amadoriase 27 and that of Amadoriase 26 (i.e., 40.6% and 28.9%, respectively).

Residual activity of Amadoriase 18 and Amadoriase 26 into which the 3T/4P/R9T/12I/13I variations were introduced was 8.9% and 28.9%, respectively. That is, tolerance thereof was enhanced compared to that of CFP-T7.

Satisfactory results were obtained as a result of introduction of the 3T/4P/R9T/12I/13I variations. Accordingly, it was considered that similar results could be obtained through simultaneous substitution of position 3 of the amadoriase with threonine, which is an amino acid having a polar side chain, position 4 with proline, position 9 with threonine, serine, asparagine, or glutamine, which is an amino acid having a polar side chain, position 12 with isoleucine, leucine, methionine, or cysteine, which is an amino acid with a larger molecular weight than that of valine, and position 13 with isoleucine, leucine, methionine, or cysteine, which is an amino acid with a larger molecular weight than that of valine.

Amadoriases 20 to 25, 27, and 28 in which such multiple variations were accumulated exhibited a significant improvement in residual activity, compared with CFP-T7. In comparison with Amadoriases 12, 17, 18, and 26, in particular, Amadoriases 22, 23, 24, 25, 27, and 28 according to the present invention have significantly enhanced tolerance to anionic surfactants. This indicates that such variations exert synergistic effects. For example, Amadoriase 20 is a variant in which the 3T/4P/R9T/12I/13I variations, the 28L/30A variations, and the 71L/77D/80R variations are accumulated, and the residual activity thereof is significantly improved compared with that of Amadoriase 12 that does not comprise such variations. Amadoriases 26, 27, and 28 are prepared by introducing the 3T/4P/R9T/12I/13I variations, the 172E/175R variations, and the 28L/30A variations in a step-wise manner. Tolerance to anionic surfactants is enhanced in a step-wise manner as the variations are accumulated, and cumulative effects of variations were confirmed. With the use of the points of variations confirmed in Example 1 of the present invention in adequate combination, accordingly, it was found that amadoriases having further improved surfactant tolerance could be prepared.

In order to examine whether or not the variations at positions 9, 12, and 13 each contribute to enhanced surfactant tolerance of amadoriase by itself, further, a revertant that starts from Amadoriase 28 and the amino acid at the position of variation is reverted to the wild-type amino acid was prepared and the anionic surfactant tolerance thereof was measured.

Specifically, in the same manner as described above, a recombinant plasmid encoding a modified amadoriase resulting from reversion of threonine at position 9 with arginine of the template (CET/E98A/G184D/ΔPTS1/F43Y/E44P/S154D/V257C/N262H/E340P/S3T/N4P/V12I/V13I/F172E/E175R/V28L/S30A) (T9R revertant) was prepared by conducting PCR using pKK223-3-CFP-T7-S3T/N4P/R9T/V12I/V13I/F43Y/E44P/E98A/S154D/G184D/V257C/N262H/E340P/ΔPTS1/F172E/E175R/V28L/S30A as the template and synthetic oligonucleotides as shown in SEQ ID NOs: 56 and 57.

Further, PCR was carried out in the same manner as described above using pKK223-3-CFP-T7-S3T/N4P/R9T/V12I/V13I/F43Y/E44P/E98A/S154D/G184D/V257C/N262H/E340P/ΔPTS1/F172E/E175R/V28L/S30A as the template and synthetic oligonucleotides as shown in SEQ ID NOs: 58 and 59 to obtain a recombinant plasmid encoding a modified amadoriase resulting from reversion of isoleucine at position 12 with valine (CET/E98A/G184D/ΔPTS1/F43Y/E44P/S154D/V257C/N262H/E340P/S3T/N4P/R9T/V13I/F172E/E175R/V28L/S30A) (I12V revertant).

Further, PCR was carried out in the same manner as described above using pKK223-3-CFP-T7-S3T/N4P/R9T/V12I/V13I/F43Y/E44P/E98A/S154D/G184D/V257C/N262H/E340P/ΔPTS1/F172E/E175R/V28L/S30A as the template and synthetic oligonucleotides as shown SEQ ID NOs: 59 and 60, so as to obtain a recombinant plasmid encoding a modified amadoriase resulting from reversion of isoleucine at position 13 with valine (CET/E98A/G184D/ΔPTS1/F43Y/E44P/S154D/V257C/N262H/E340P/S3T/N4P/R9T/V12I/F172E/E175R/V28L/S30A) (I13V revertant).

The multiple variants were produced in the same manner as in Example 1, the resulting crude enzyme solutions were designated as samples, and surfactant tolerance of various modified amadoriases was evaluated in accordance with the method for evaluation of surfactant tolerance described in (4) above while surfactant treatment was carried out using a 0.04% SDS mixture. The results are shown in Table 4. It was confirmed that there was no change in the activity value when the warmed sample was diluted 2-fold with a BSA solution and then subjected to activity measurement again 30 minutes later.

TABLE 4

| Amadoriase | Mutation | Residual activity after SDS treatment (%) |
|---|---|---|
| Amadoriase 28 | E98A/G184D/APTS1/F43Y/E44P/S154D/V257C/N262H/ E340P/S3T/N4P/R9T/V12I/V13I/F172E/E175R/V28L/S30A | 81.9 |
| Amadoriase 29 | E98A/G184D/APTS1/F43Y/E44P/S154D/V257C/N262H/ E340P/S3T/N4P/V12I/V13I/F172E/E175R/V28L/S30A | 63.3 |
| Amadoriase 30 | E98A/G184D/APTS1/F43Y/E44P/S154D/V257C/N262H/ E340P/S3T/N4P/R9T/V13I/F172E/E175R/V28L/S30A | 55.1 |
| Amadoriase 31 | E98A/G184D/APTS1/F43Y/E44P/S154D/V257C/N262H/ E340P/S3T/N4P/R9T/V12I/F172E/E175R/V28L/S30A | 58.0 |

As shown in Table 4, in comparison with Amadoriase 28 comprising all the variations R9T, V12I, and V13I and having a residual activity of 81.9%, Amadoriase 29 resulting from reversion of position 9 with arginine alone had a residual activity that was reduced to 63.3%. In other words, the single variation (mutation) of the present invention starting from Amadoriase 29 via reversion of arginine at position 9 with threonine results in the preparation of Amadoriase 28. This variation alone leads to enhanced residual activity equivalent to 18.6%; that is, this variation confers tolerance to surfactants.

Further, in comparison with Amadoriase 28 comprising all the variations R9T, V12I, and V13I and having a residual activity of 81.9%, the residual activity of Amadoriase 30 resulting from reversion of position 12 with valine alone was reduced to 55.1%. In other words, the single variation of the present invention starting from Amadoriase 30 via reversion of valine at position 12 to isoleucine leads to construction of Amadoriase 28. This one variation leads to enhanced residual activity equivalent to 26.8%; that is, this variation confers tolerance to surfactants.

Further, in comparison with Amadoriase 28 comprising all the variations R9T, V12I, and V13I and having a residual activity of 81.9%, the residual activity of Amadoriase 31 resulting from reversion of position of substitution of valine was reduced to 58.0%. In other words, the single variation of the present invention starting from Amadoriase 31 via reversion of valine at position 13 to isoleucine results in the construction of Amadoriase 28. This one variation (mutation) leads to enhanced residual activity equivalent to 23.9%; that is, this variation confers tolerance to surfactants.

Thus, these results demonstrate that the variations at positions 9, 12, and 13 each contribute to enhanced surfactant tolerance of the amadoriase even when applied independently.

Example 3

(Purification of CFP-T7 and Various Modified Amadoriases)

The crude enzyme solutions prepared using crude enzymes CFP-T7, CFP-T7-M71A, Amadoriase 21, Amadoriase 24, and Amadoriase 25-F286Y obtained in Examples 1 and 2 were allowed to adsorb to 4 ml of Q Sepharose Fast Flow resin (manufactured by GE Healthcare) equilibrated with a 20 mM potassium phosphate buffer (pH 8.0), the resin was washed with 80 ml of the same buffer, the proteins that were adsorbed to the resin was eluted with the aid of a 20 mM potassium phosphate buffer (pH 8.0) containing 100 mM NaCl, and fractions exhibiting amadoriase activity were then collected.

The fractions exhibiting amadoriase activity were concentrated using Amicon Ultra-15 (NMWL: 30K, manufactured by Millipore). Thereafter, the resultant was applied to the HiLoad 26/60 Superdex 200 pg column (manufactured by GE Healthcare) equilibrated with a 20 mM potassium phosphate buffer (pH 7.0) containing 150 mM NaCl so as to carry out elution with the same buffer, fractions exhibiting amadoriase activity were collected, and purified samples of wild-type and modified amadoriases were then obtained. The purified samples were analyzed via SDS-PAGE and confirmed that the fractions had been purified to the extent that a single band was obtained.

Purified CFP-T7 was treated with an anionic surfactant under the conditions described in Example 2 and the residual activity thereof was measured and found to be 0%. In contrast, the purified Amadoriase 24 according to the present invention was treated with an anionic surfactant under the conditions described in Example 2 and the residual activity thereof was measured and found to be 67.2% and a significant improvement was observed.

Example 4

(Test for Tolerance to Various Surfactants)

The purified amadoriases obtained in Example 3 were designated as samples and surfactant tolerance of various modified amadoriases was evaluated in accordance with the method for measurement of surfactant tolerance described in (4) above. The results are shown in Tables 5 and 6. However, the final concentration of the surfactant used for evaluation was as in Tables 5 and 6. It was confirmed that there was no change in the activity value when the warmed sample was diluted 2-fold with a BSA solution and then subjected to activity measurement again 30 minutes later.

TABLE 5

| | Residual activity after treatment (%) | | | | |
|---|---|---|---|---|---|
| Amadoriase | 1.0% sodium octyl sulfate | 0.0032% sodium tetradecyl sulfate | 0.0050% sodium 4-octylbenzene sulfonate | 1.0% sodium cholate | 0.60% sodium deoxycholate |
| CFP-T7 | 71.0 | 78.9 | 58.1 | 135.9 | 37.5 |
| CFP-T7-M71A | 82.8 | 104.7 | 83.6 | 145.8 | 122.5 |

TABLE 6

| Amadoriase | Residual activity after treatment (%) | | | | | | | | |
|---|---|---|---|---|---|---|---|---|---|
| | 2.0% sodium octyl sulfate | 0.04% SDS | 0.0064% sodium tetradecyl sulfate | 0.0032% sodium octadecyl sulfate | 0.050% sodium 4-octyl-benzene sulfonate | 0.010% sodium 4-dodecyl-benzene sulfonate | 2.0% sodium cholate | 1.2% sodium deoxycholate | 0.20% SDDS |
| CFP-T7 | 0 | 0 | 3.9 | 0.2 | 11.12 | 2.6 | 6.4 | 9.2 | 8.45 |
| Amadoriase 21 | 0.7 | 36.93 | — | 0.8 | — | 6.4 | — | 74.4 | — |
| Amadoriase 25-F286Y | 13.9 | 93.62 | 11.9 | 27.3 | 76.41 | 13.3 | 12.6 | 153.1 | 102.13 |

As shown in Table 5, the M71A variant exhibited an improvement in residual activity even in the presence of various surfactants, compared with non-mutated CFP-T7. Incidentally, the non-mutated CFP-T7 amadoriase exhibited a significant increase in activity level in the presence of 1.0% (w/v) sodium cholate, compared with the case where sodium cholate was not added (100%). That is, under such conditions, sodium cholate enhanced amadoriase activity. Moreover, combination of the M71A variant with 1.0% sodium cholate exhibited a further increase in activity level compared with the amadoriase that does not have such mutation (variation). This indicates that the M71A variation can enhance tolerance to sodium cholate or further enhance amadoriase activity in the presence of sodium cholate. Further, the M71A variation not only enhanced surfactant tolerance in the presence of 0.6% sodium deoxycholate, but also further enhanced amadoriase activity, compared with the case in the absence of sodium deoxycholate.

Further, as shown in Table 6, Amadoriase 21 exhibited an improvement in residual activity in the presence of 2.0% sodium octyl sulfate, 0.4% SDS, 0.010% sodium 4-dodecyl-benzene sulfonate, and 1.2% sodium deoxycholate, compared with non-mutated CFP-T7. The variant resulting from the introduction of the F286Y variation into Amadoriase 25 exhibited an improvement in residual activity in the presence of all surfactants subjected to the test, compared with CFP-T7. Moreover, Amadoriase 25-F286Y variant not only enhanced surfactant tolerance in the presence of 1.2% sodium deoxycholate, but also further enhanced amadoriase activity, compared with the case in the absence of sodium deoxycholate.

Since satisfactory results were obtained as a result of substitution of position 286 with tyrosine, it was considered that similar results could be obtained through substitution with tryptophan, which is also a hydrophobic amino acid with a large molecular weight.

Example 5

(Surfactant Tolerance Enhancing Variations on CFP-T7)
(1) Site-Directed Modification Procedure of DNA of Recombinant Plasmid pKK223-3-CFP-T7

PCR was carried out in accordance with the method described in Example 1 using synthetic oligonucleotides as shown in SEQ ID NOs: 123 and 124 and the recombinant plasmid pKK223-3-CFP-T7 as the template, so as to obtain a recombinant plasmid encoding a modified amadoriase resulting from substitution of glutamic acid at position 44 with lysine in the amino acid sequence as shown in SEQ ID NO: 1 (pKK223-3-CFP-T7-E44K).

In the same manner, PCR was carried out using synthetic oligonucleotides as shown in SEQ ID NOs: 125 and 126, so as to obtain a recombinant plasmid encoding a modified amadoriase resulting from substitution of aspartic acid at position 194 with lysine in the amino acid sequence as shown in SEQ ID NO: 1 (pKK223-3-CFP-T7-D194K).

In the same manner, PCR was carried out using synthetic oligonucleotides as shown in SEQ ID NOs: 125 and 127, so as to obtain a recombinant plasmid encoding a modified amadoriase resulting from substitution of aspartic acid at position 194 with alanine in the amino acid sequence as shown in SEQ ID NO: 1 (pKK223-3-CFP-T7-D194A).

In the same manner, PCR was carried out using synthetic oligonucleotides as shown in SEQ ID NOs: 128 and 129, so as to obtain a recombinant plasmid encoding a modified amadoriase resulting from substitution of glutamic acid at position 204 with alanine in the amino acid sequence as shown in SEQ ID NO: 1 (pKK223-3-CFP-T7-E204A).

In the same manner, PCR was carried out using synthetic oligonucleotides as shown in SEQ ID NOs: 130 and 131, so as to obtain a recombinant plasmid encoding a modified amadoriase resulting from substitution of aspartic acid at position 338 with alanine in the amino acid sequence as shown in SEQ ID NO: 1 (pKK223-3-CFP-T7-D338A).

In the same manner, PCR was carried out using synthetic oligonucleotides as shown in SEQ ID NOs: 132 and 133, so as to obtain a recombinant plasmid encoding a modified amadoriase resulting from substitution of glutamic acid at position 340 with lysine in the amino acid sequence as shown in SEQ ID NO: 1 (pKK223-3-CFP-T7-E340K).

The nucleotide sequences of DNAs encoding amadoriases in the plasmids described above were determined in the same manner as described above, so as to confirm the introduction of the variation.

(2) Production of Various Modified Amadoriases

Strains of *E. coli* JM109 carrying the recombinant plasmids obtained in the manner described above were cultured in 3 ml of LB-amp media supplemented with 0.1 mM IPTG at 30° C. for 16 hours. Thereafter, the resulting cultured strains were washed with a 0.01 M phosphate buffer (pH 7.0), the washed strains were ultrasonically disrupted, and the resultants were centrifuged at 15,000 rpm for 10 minutes to prepare 1.5 ml each of crude enzyme solutions.

(3) Evaluation of Surfactant Tolerance of Various Modified Amadoriases

Using each crude enzyme solution thus prepared as a sample, the final concentration of SDS was set at 0.036%, so as to evaluate the surfactant tolerance of each of the modified amadoriases in accordance with the above measurement method for surfactant tolerance. The results are shown in Table 7. It was confirmed that there was no change in the activity value when the warmed sample was diluted 2-fold with a BSA solution and then subjected to activity measurement again 30 minutes later.

In Table 7, CFP-T7 indicates an amadoriase derived from a strain of *Escherichia coli* JM109 (pKK223-3-CFP-T7). In this example, CFP-T7, which is an amadoriase derived from the strain E. coli JM109 (pKK223-3-CFP-T7), is employed as the original enzyme for source of mutation and, therefore, descriptions concerning "Amino acid mutations" in the table do not include various points of mutations that have already been introduced into CFP-T7.

These points of variations according to the present invention are effective as single variations. In addition, such points of variations may be used in combination with various types of variations that are known. Further, use of the variations of the present invention in combination with

TABLE 7

| Amadoriase | Template plasmid | Mutation | Oligonucleotide SEQ ID NO. | Residual activity after treatment (%) 0.036% SDS |
| --- | --- | --- | --- | --- |
| CFP-T7 | None | None | None | 9.6 |
| CFP-T7-E44K | pKK223-3-CFP-T7 | E44K | 123, 124 | 17.5 |
| CFP-T7-D194K | | D194K | 125, 126 | 10.9 |
| CFP-T7-D194A | | D194A | 125, 127 | 12.5 |
| CFP-T7-E204A | | E204A | 128, 129 | 47.3 |
| CFP-T7-D338A | | D338A | 130, 131 | 32.2 |
| CFP-T7-E340K | | E340K | 132, 133 | 14.9 |

As shown in Table 7, the residual activity of CFP-T7 was 9.6% after treatment with 0.036% SDS under the conditions of the present example. By contrast, regarding the 6 variants obtained by site-directed mutagenesis, that is, each amadoriase in which glutamic acid at position 44 in CFP-T7 is substituted with lysine, aspartic acid at position 194 with lysine, glutamic acid at position 204 with alanine, aspartic acid at position 338 with alanine, or glutamic acid at position 340 with lysine, respectively, the residual activity was enhanced by 2.9% to 37.7% in the presence of SDS, compared with CFP-T7. An amadoriase variant of CFP-T7 resulting from substitution of aspartic acid at position 194 with alanine exhibited an improvement in residual activity by 1.3% in the presence of SDS, compared with CFP-T7. Accordingly, these points of variations were found to enhance surfactant tolerance of amadoriases.

Since satisfactory results were obtained as a result of substitution of position 44 with lysine, it is considered that similar results could be obtained through substitution of position 44 with arginine or histidine, which is also a basic amino acid.

Since satisfactory results were obtained as a result of substitution of position 194 with lysine or alanine, it is considered that similar results could be obtained through substitution of position 194 with arginine or histidine, which is also a basic amino acid, and substitution of position 194 with leucine, isoleucine, valine, or cysteine, which is also a hydrophobic amino acid with a small molecular weight.

Since satisfactory results were obtained as a result of substitution of position 204 with alanine, it is considered that similar results could be obtained through substitution of position 204 with leucine, isoleucine, valine, or cysteine, which is also a hydrophobic amino acid with a small molecular weight.

Since satisfactory results were obtained as a result of substitution of position 338 with alanine, it is considered that similar results could be obtained through substitution of position 338 with leucine, isoleucine, valine, or cysteine, which is also a hydrophobic amino acid with a small molecular weight.

Since satisfactory results were obtained as a result of substitution of position 340 with lysine, it is considered that similar results could be obtained through substitution of position 340 with arginine or histidine, which is also a basic amino acid.

each other is expected to contribute to preparation of variants that are practically advantageous.

Example 6

(Site-Directed Modification Procedure of Various Amadoriases)
(Preparation of DNA of Recombinant Plasmid pKK223-3-CcFX)

SEQ ID NO: 94 shows the amino acid sequence of ketoamine oxidase derived from Curvularia clavata (CcFX) (WO 2004/104203). This can be prepared by E. coli strains harboring the recombinant plasmid pKK223-3-CcFX into which the gene (SEQ ID NO: 95) encoding the amino acid sequence as shown in SEQ ID NO: 94 has been inserted (see WO 2015/020200). The E. coli JM109 strain harboring pKK223-3-CcFX was cultured in accordance with the method described in "Example 1 (1) Preparation of DNA of recombinant plasmid pK223-3-CFP-T7," and pKK223-3-CcFX was extracted and purified.

(Introduction of Point Mutation into Gene of Ketoamine Oxidase Derived from Curvularia clavata)

In order to introduce a substrate specificity enhancing mutation into CcFX, in the same manner as in Example 1, PCR was carried out using the recombinant plasmid pKK223-3-CcFX as the template, synthetic oligonucleotides as shown in SEQ ID NOs: 96 and 97, and KOD-Plus- (manufactured by TOYOBO CO., LTD.), 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of E. coli JM109 were transformed using the reaction solution, and the nucleotide sequence of DNA encoding the CcFX variant in the plasmid DNA carried on the grown colonies was determined. As a result, a recombinant plasmid encoding the CcFX gene resulting from substitution of valine at position 28 with leucine in the amino acid sequence as shown in SEQ ID NO: 94 was obtained (pKK223-3-CcFX-V28L).

In the same manner as described above, subsequently, a recombinant plasmid encoding the CcFX gene resulting from substitution of valine at position 28 with methionine in the amino acid sequence as shown in SEQ ID NO: 94 was obtained using pKK223-3-CcFX as the template and synthetic oligonucleotides as shown in SEQ ID NOs: 96 and 98 (pKK223-3-CcFX-V28M).

In the same manner as described above, subsequently, a recombinant plasmid encoding the CcFX gene resulting from substitution of leucine at position 71 with alanine in the amino acid sequence as shown in SEQ ID NO: 94 was obtained using pKK223-3-CcFX as the template and synthetic oligonucleotides as shown in SEQ ID NOs: 99 and 100 (pKK223-3-CcFX-L71A).

In the same manner as described above, subsequently, a recombinant plasmid encoding the CcFX gene resulting from substitution of leucine at position 71 with valine in the amino acid sequence as shown in SEQ ID NO: 94 was obtained using pKK223-3-CcFX as the template and synthetic oligonucleotides as shown in SEQ ID NOs: 99 and 101 (pKK223-3-CcFX-L71V).

In the same manner as described above, subsequently, a recombinant plasmid encoding the CcFX gene resulting from substitution of arginine at position 80 with asparagine in the amino acid sequence as shown in SEQ ID NO: 94 was obtained using pKK223-3-CcFX as the template and synthetic oligonucleotides as shown in SEQ ID NOs: 102 and 103 (pKK223-3-CcFX-R80N).

In the same manner as described above, subsequently, a recombinant plasmid encoding the CcFX gene resulting from substitution of arginine at position 80 with glutamine in the amino acid sequence as shown in SEQ ID NO: 94 was obtained using pKK223-3-CcFX as the template and synthetic oligonucleotides as shown in SEQ ID NOs: 102 and 104 (pKK223-3-CcFX-R80Q).

In the same manner as described above, subsequently, a recombinant plasmid encoding the CcFX gene resulting from substitution of tyrosine at position 172 with glutamic acid in the amino acid sequence as shown in SEQ ID NOs: 94 was obtained using pKK223-3-CcFX as the template and synthetic oligonucleotides as shown in SEQ ID NOs: 105 and 106 (pKK223-3-CcFX-Y172E).

In the same manner as described above, subsequently, a recombinant plasmid encoding the CcFX gene resulting from substitution of tyrosine at position 172 with aspartic acid in the amino acid sequence as shown in SEQ ID NOs: 94 was obtained using pKK223-3-CcFX as the template and synthetic oligonucleotides as shown in SEQ ID NOs: 105 and 107 (pKK223-3-CcFX-Y172D).

In the same manner as described above, subsequently, a recombinant plasmid encoding the CcFX gene resulting from substitution of alanine at position 175 with lysine in the amino acid sequence as shown in SEQ ID NOs: 94 was obtained using pKK223-3-CcFX as the template and synthetic oligonucleotides as shown in SEQ ID NOs: 108 and 109 (pKK223-3-CcFX-A175K).

(Introduction of Point Mutation into Gene of Ketoamine Oxidase Derived from *Emericella nidulans*)

SEQ ID NO: 110 shows the amino acid sequence of glycated hexapeptide oxidase derived from *Emericella nidulans* (En42FX) (WO 2015/005258). The gene (SEQ ID NO: 111) encoding the amino acid sequence as shown in SEQ ID NO: 110 was obtained by a conventional technique of total synthesis of cDNA via PCR of a gene fragment (including the termination codon TAA). In order to express the gene comprising the sequence as shown in SEQ ID NO: 111 in *E. coli*, subsequently, the process described below was carried out. First, a fragment comprising the gene comprising the sequence as shown in SEQ ID NO: 111 was amplified using synthetic oligonucleotides as shown in SEQ ID NOs: 112 and 113 in accordance with the users' manual of the In-Fusion HD Cloning Kit (manufactured by Clontech Laboratories, Inc.). At the same time, a fragment containing pET22b was amplified using synthetic oligonucleotides as shown in SEQ ID NOs: 113 and 115. Subsequently, a fragment comprising the gene comprising the sequence as shown in SEQ ID NO: 111 was subcloned into a fragment comprising pET22b via the in-fusion reaction to obtain the recombinant plasmid (pET22b-En42FX), strains of *E. coli* JM109 were transformed under the same conditions as described above, and strains of *E. coli* JM109 were obtained (pET22b-En42FX).

In order to introduce a substrate specificity enhancing mutation into En42FX, in the same manner as in Example 1, PCR was carried out using the recombinant plasmid pET22b-En42FX as the template, synthetic oligonucleotides as shown in SEQ ID NOs: 116 and 117, and KOD-Plus- (manufactured by TOYOBO CO., LTD.), 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of *E. coli* JM109 were transformed using the reaction solution, and the nucleotide sequence of DNA encoding the En42FX variant in the plasmid DNAs carried on the grown colonies was determined. As a result, a recombinant plasmid encoding the En42FX gene comprising an amino acid sequence resulting from substitution of leucine at position 70 with valine in the amino acid sequence as shown in SEQ ID NO: 110 was obtained (pET22b-En42FX-L70V).

In the same manner as described above, subsequently, a recombinant plasmid encoding the En42FX gene resulting from substitution of phenylalanine at position 171 with aspartic acid in the amino acid sequence as shown in SEQ ID NOs: 110 was obtained using pET22b-En42FX as the template and synthetic oligonucleotides as shown in SEQ ID NO2: 134 and 135 (pET22b-En42FX-F171D).

In the same manner as described above, subsequently, a recombinant plasmid encoding the En42FX gene resulting from substitution of glutamic acid at position 174 with arginine in the amino acid sequence as shown in SEQ ID NOs: 110 was obtained using pET22b-En42FX as the template and synthetic oligonucleotides as shown in SEQ ID NO: 136 and 137 (pET22b-En42FX-E174R).

Strains of *E. coli* BL21 (DE3) were transformed under the same conditions where strains of *E. coli* JM109 were transformed, so as to obtain strains of *E. coli* BL21 (DE3) (pET22b-En42FX), strains of *E. coli* BL21 (DE3) (pET22b-En42FX-L70V), strains of *E. coli* BL21 (DE3) (pET22b-En42FX-F171D), and strains of *E. coli* BL21 (DE3) (pET22b-En42FX-E174R).

(Production of Various Modified Amadoriases)

Strains of *E. coli* JM109 or strains of *E. coli* BL21 (DE3) carrying the recombinant plasmids obtained in the manner described above were cultured in 3 ml of LB-amp media supplemented with 0.1 mM IPTG at 25° C. for 16 hours. Thereafter, the resulting cultured strains were washed with a 0.01 M phosphate buffer (pH 7.0), the washed strains were ultrasonically disrupted, and the resultants were centrifuged at 15,000 rpm for 10 minutes to prepare 1.5 ml each of crude enzyme solutions.

(Evaluation of Surfactant Tolerance of Various Modified Amadoriases)

Using each crude enzyme solution thus prepared as a sample, the final concentration of SDDS (manufactured by Tokyo Kasei Kogyo Co., Ltd.) was set at 0.1% or 0.15%, so as to evaluate the surfactant tolerance of each of the modified amadoriases in accordance with the above measurement method for surfactant tolerance. The results are shown in the tables below. It was confirmed that there was no change in the activity value when the warmed sample was diluted 2-fold with a BSA solution and then subjected to activity measurement again 30 minutes later. In Table 8, CcFX indicates an amadoriase derived from a strain of *Escherichia coli* JM109 (pKK223-3-CcFx). In Table 9, En42Fx indicates an amadoriase derived from a strain of *Escherichia coli* BL21 (DE3) (pET22b-En42FX). In this example, En42Fx, which is an amadoriase derived from *E. coli* BL21 (DE3) (pET22b-En42FX) strain, is employed as the original enzyme for source of mutation and, therefore, descriptions concerning "Amino acid mutations" in the table do not include various points of mutations that have already been introduced into En42Fx.

TABLE 8

| Amadoriase | Template plasmid | Mutation | Oligonucleotide SEQ ID NO. | Residual activity after treatment (%) 0.10% SDDS |
|---|---|---|---|---|
| CcFX | None | None | None | 83.7 |
| CcFX-V28L | pKK223-3-CcFX | V28L | 96, 97 | 92.8 |
| CcFX-V28M | | V28M | 96, 98 | 93.6 |
| CcFX-L71A | | L71A | 99, 100 | 90.1 |
| CcFX-L71V | | L71V | 99, 101 | 185.7 |
| CcFX-R80N | | R80N | 102, 103 | 99.1 |
| CcFX-R80Q | | R80Q | 102, 104 | 91.8 |
| CcFX-Y172E | | Y172E | 105, 106 | 97.6 |
| CcFX-Y172D | | Y172D | 105, 107 | 94.7 |
| CcFX-A175K | | A175K | 108, 109 | 91.0 |

TABLE 9

| Amadoriase | Template plasmid | Mutation | Oligonucleotide SEQ ID NO. | Residual activity after treatment (%) 0.15% SDDS |
|---|---|---|---|---|
| En42FX | None | None | None | 0 |
| En42FX-L70V | pET22b-En42FX | L70V | 116, 117 | 4.8 |
| En42FX-F171D | | F171D | 134, 135 | 6.7 |
| En42FX-E174R | | E174R | 136, 137 | 3.2 |

As described above, all the mutations conferred CcFX with enhanced tolerance to SDDS on their own (as single mutations). The L71V variation resulted in a significant elevated activity level, compared with the case in which SDDS was not added (100%). Accordingly, it can be said that the L71V variation can not only enhance tolerance to SDDS but also further enhance the amadoriase activity in the presence of 0.1% SDDS. Since the activity level of the CcFX-L71V variant in the presence of SDDS exceeded the activity (100%) in the absence of SDDS, tolerance to SDS was also tested. As a result, non-mutated CcFX was found to have the residual activity of 16.6% in the presence of 0.036% SDS, and the CcFX-L71V variant was found to have the residual activity of 20.9% in the presence of 0.036% SDS; that is, the CcFX-L71V variant achieved enhanced tolerance to SDS.

En42Fx achieved enhanced tolerance to SDDS as a result of the L70V variation, the F171D variation, and the E174R variation. This indicates that the effects of enhanced tolerance to anionic surfactants achieved by the amino acid substitution can be exerted regardless of the amadoriase origin.

Brief Description of Sequences

SEQ ID NO: 1: the amino acid sequence of CFP-T7
SEQ ID NO: 2: the gene sequence of CFP-T7
SEQ ID NO: 3: the amadoriase derived from *Eupenicillium terrenum*
SEQ ID NO: 4: the ketoamine oxidase derived from *Pyrenochaeta* sp.
SEQ ID NO: 5: the ketoamine oxidase derived from *Arthrinium* sp.
SEQ ID NO: 6: the ketoamine oxidase derived from *Curvularia clavata*
SEQ ID NO: 7: the ketoamine oxidase derived from *Neocosmospora vasinfecta*
SEQ ID NO: 8: the fructosyl amino acid oxidase derived from *Cryptococcus neoformans*
SEQ ID NO: 9: the fructosyl peptide oxidase derived from *Phaeosphaeria nodorum*
SEQ ID NO: 10: the fructosyl amino acid oxidase derived from *Aspergillus nidulans*
SEQ ID NO: 11: the fructosyl peptide oxidase derived from *Emericella nidulans*
SEQ ID NO: 12: the fructosyl amino acid oxidase derived from *Ulocladium* sp.
SEQ ID NO: 13: the fructosyl amino acid oxidase derived from *Penicillium janthinellum*
SEQ ID NO: 14: R9T-Fw
SEQ ID NO: 15: R9T-Rv
SEQ ID NO: 16: V12I-Fw
SEQ ID NO: 17: V12I-Rv
SEQ ID NO: 18: M71L-Fw
SEQ ID NO: 19: M71X-Rv
SEQ ID NO: 20: K80R-Fw
SEQ ID NO: 21: K80R-Rv
SEQ ID NO: 22: F172E-Fw
SEQ ID NO: 23: F172E-Rv
SEQ ID NO: 24: E175R-Fw
SEQ ID NO: 25: E175R-Rv
SEQ ID NO: 26: V279I-Fw SEQ ID NO: 27: V279X-Rv
SEQ ID NO: 28: V28L-Fw
SEQ ID NO: 29: V28X-Rv
SEQ ID NO: 30: S30A-Fw
SEQ ID NO: 31: S30X-Rv
SEQ ID NO: 32: Q77D-Fw
SEQ ID NO: 33: Q77D-Rv
SEQ ID NO: 34: F43Y/E44P-Fw
SEQ ID NO: 35: E44X-Rv
SEQ ID NO: 36: H53N-Fw
SEQ ID NO: 37: H53X-Rv
SEQ ID NO: 38: E340P-Fw
SEQ ID NO: 39: E340X-Rv
SEQ ID NO: 40: F172E/E175R-Fw
SEQ ID NO: 41: V28LS30A-Fw
SEQ ID NO: 42: Q77D/K80R-Fw
SEQ ID NO: 43: Q77D/K80R-Rv
SEQ ID NO: 44: R9T/V12I/V13I-Fw
SEQ ID NO: 45: R9T/V12I/V13I-Rv
SEQ ID NO: 46: S3T/N4P-Fw
SEQ ID NO: 47: S3T/N4P/R9T/V12I/V13I-Rv
SEQ ID NO: 48: S154D-Fw
SEQ ID NO: 49: S154D-Rv
SEQ ID NO: 50: V257C/N262H-Fw
SEQ ID NO: 51: V257C/N262H-Rv
SEQ ID NO: 52: ΔPTS1-Fw
SEQ ID NO: 53: ΔPTS1-Rv
SEQ ID NO: 54: E98A-Fw
SEQ ID NO: 55: E98A-Rv
SEQ ID NO: 56: T9R/V12I/V13I-Fw
SEQ ID NO: 57: T9R/V12I/V13I-Rv
SEQ ID NO: 58: R9T/I12V/I13I-Fw
SEQ ID NO: 59: V13X-Rv
SEQ ID NO: 60: R9T/V12I/I13V-Fw
SEQ ID NO: 61: CET_V12X_Rv
SEQ ID NO: 62: CET_V12L_Fw
SEQ ID NO: 63: CET_V13X_Rv
SEQ ID NO: 64: CET_V13L_Fw
SEQ ID NO: 65: CET_V28X_Rv
SEQ ID NO: 66: CET_V28I_Fw
SEQ ID NO: 67: CET_V28M_Fw
SEQ ID NO: 68: CET_S30X_Rv
SEQ ID NO: 69: CET_S30T_Fw
SEQ ID NO: 70: CET_V30V_Fw
SEQ ID NO: 71: CET_M71X_Rv
SEQ ID NO: 72: CET_M71I_Fw
SEQ ID NO: 73: CET_M71A_Fw
SEQ ID NO: 74: CET_M71V_Fw
SEQ ID NO: 75: CET_M71C_Fw
SEQ ID NO: 76: CET_Q77X_Rv
SEQ ID NO: 77: CET_Q77E_Fw
SEQ ID NO: 78: CET_Q77K_Fw
SEQ ID NO: 79: CET_Q77K_Fw
SEQ ID NO: 80: E77N_f
SEQ ID NO: 81: CET K80X_Rv
SEQ ID NO: 82: CET K80N_Fw
SEQ ID NO: 83: CET K80Q_Fw
SEQ ID NO: 84: K80H f
SEQ ID NO: 85: CET F172X_Rv
SEQ ID NO: 86: CET F172D_Fw
SEQ ID NO: 87: CET F172Y_Fw
SEQ ID NO: 88: CET F172Q_Fw
SEQ ID NO: 89: CET E175X_Rv
SEQ ID NO: 90: CET E175K_Fw
SEQ ID NO: 91: CET E175H_Fw
SEQ ID NO: 92: V279C f
SEQ ID NO: 93: V279C r
SEQ ID NO: 94: Cc-Pr protein
SEQ ID NO: 95: Cc-Gn gene
SEQ ID NO: 96: CcFx V28X_Rv
SEQ ID NO: 97: CcFx V28L_Fw
SEQ ID NO: 98: CcFx V28M_Fw
SEQ ID NO: 99: CcFx L71X_Rv
SEQ ID NO: 100: CcFx L71A_Fw
SEQ ID NO: 101: CcFx L71V_Fw
SEQ ID NO: 102: CcFx R80X_Rv
SEQ ID NO: 103: CcFx R80N_Fw
SEQ ID NO: 104: CcFx R80Q_Fw
SEQ ID NO: 105: CcFx Y172X_Rv
SEQ ID NO: 106: CcFx Y172E_Fw
SEQ ID NO: 107: CcFx Y172D_Fw
SEQ ID NO: 108: CcFx A175X_Rv
SEQ ID NO: 109: CcFx A175K_Fw
SEQ ID NO: 110: En-Pr protein
SEQ ID NO: 111: En-Gn gene
SEQ ID NO: 112: En-c1
SEQ ID NO: 113: En-c2
SEQ ID NO: 114: En-c3
SEQ ID NO: 115: En-c4
SEQ ID NO: 116: En_L70X_Rv
SEQ ID NO: 117: En_L70V_Fw
SEQ ID NO: 118: R9X_Rv
SEQ ID NO: 119: R9N_Fw
SEQ ID NO: 120: R9Q_Fw
SEQ ID NO: 121: F286X-Rv
SEQ ID NO: 122: F286Y-Fw
SEQ ID NO: 123: E44K_Rv
SEQ ID NO: 124: E44K_Fw
SEQ ID NO: 125: D194X_Rv
SEQ ID NO: 126: D194K_Fw
SEQ ID NO: 127: D194A_Fw
SEQ ID NO: 128: E204A_Rv
SEQ ID NO: 129: E204A_Fw
SEQ ID NO: 130: D338A_Rv
SEQ ID NO: 131: D338A_Fw
SEQ ID NO: 132: E340K_Rv
SEQ ID NO: 133: E340K_Fw
SEQ ID NO: 134: F171D_Rv
SEQ ID NO: 135: F171D_Fw
SEQ ID NO: 136: E174R_Rv
SEQ ID NO: 137: E174R_Fw All publications, patents, and patent applications cited herein are incorporated herein by reference in their entirety.

The invention claimed is:

1. A modified amadoriase, wherein said modified amadoriase comprises an amino acid sequence exhibiting 90% or higher sequence identity with the amino acid sequence of SEQ ID NO: 1, SEQ ID NO: 94, or SEQ ID NO: 110 over the full length, and comprises one or more amino acid substitutions at one or more positions corresponding to positions selected from the group consisting of positions 80, 175, 172, 279, 12, 9, 77, 30, 28, 13, 3, 4, 286, 204, 338, and 194 in the amino acid sequence as shown in SEQ ID NO: 1, exhibiting activity on α-fructosyl valine (αFV) or α-fructosyl-valyl-histidine (αFVH), wherein when sodium dodecanoylsarcosinate is added to a final concentration of 0.15% (w/v) to said modified amadoriase and to an amadoriase not having such amino acid substitutions, and the amadoriases are allowed to stand at 30° C. for 5 minutes, the modified amadoriase exhibits a residual activity increased by 3% or more compared with the amadoriase not having such amino acid substitutions, in terms of comparison of residual activity (%) values;

wherein the modified amadoriase comprises one or more of the following:

(a) an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, asparagine, glutamine, or histidine;

(b) an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, histidine, or lysine;

(c) an amino acid sequence in which, when aligned with the amino acid sequence as shown in SEQ ID NO: 1, the amino acid at the position corresponding to phenylalanine at position 172 in the amino acid sequence as shown in SEQ ID NO: 1 is glutamic acid, aspartic acid, tyrosine, or glutamine;

(d) an amino acid sequence in which, when aligned with the amino acid sequence as shown in SEQ ID NO: 1, the amino acid at the position corresponding to valine at position 279 in the amino acid sequence as shown in SEQ ID NO: 1 is isoleucine or cysteine;

(e) an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine, leucine, cysteine, or methionine;

(f) an amino acid sequence in which, when aligned with the amino acid sequence as shown in SEQ ID NO: 1, the amino acid at the position corresponding to arginine at position 9 in the amino acid sequence as shown in SEQ ID NO: 1 is threonine, asparagine, or glutamine;

(g) an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid, glutamic acid, lysine, or asparagine;

(h) an amino acid sequence in which, when aligned with the amino acid sequence as shown in SEQ ID NO: 1, the amino acid at the position corresponding to serine at position 30 in the amino acid sequence as shown in SEQ ID NO: 1 is threonine, valine, leucine, or isoleucine;

(i) an amino acid sequence in which, when aligned with the amino acid sequence as shown in SEQ ID NO: 1, the amino acid at the position corresponding to valine at position 28 in the amino acid sequence as shown in SEQ ID NO: 1 is isoleucine, methionine, alanine, or cysteine;

(j) an amino acid sequence in which, when aligned with the amino acid sequence as shown in SEQ ID NO: 1, the amino acid at the position corresponding to valine at position 13 in the amino acid sequence as shown in SEQ ID NO: 1 is isoleucine, leucine, cysteine, or methionine;

(k) an amino acid sequence in which, when aligned with the amino acid sequence as shown in SEQ ID NO: 1, the amino acid at the position corresponding to serine at position 3 in the amino acid sequence as shown in SEQ ID NO: 1 is threonine;

(l) an amino acid sequence in which, when aligned with the amino acid sequence as shown in SEQ ID NO: 1, the amino acid at the position corresponding to asparagine at position 4 in the amino acid sequence as shown in SEQ ID NO: 1 is proline;

(m) an amino acid sequence in which, when aligned with the amino acid sequence as shown in SEQ ID NO: 1, the amino acid at the position corresponding to phenylalanine at position 286 in the amino acid sequence as shown in SEQ ID NO: 1 is tyrosine or tryptophan;

(n) an amino acid sequence in which, when aligned with the amino acid sequence as shown in SEQ ID NO: 1, the amino acid at the position corresponding to glutamic acid at position 204 in the amino acid sequence as shown in SEQ ID NO: 1 is alanine, leucine, isoleucine, valine, or cysteine;

(o) an amino acid sequence in which, when aligned with the amino acid sequence as shown in SEQ ID NO: 1, the amino acid at the position corresponding to aspartic acid at position 338 in the amino acid sequence as shown in SEQ ID NO: 1 is alanine, leucine, isoleucine, valine, or cysteine; and (p) an amino acid sequence in which, when aligned with the amino acid sequence as shown in SEQ ID NO: 1, the amino acid at the position corresponding to aspartic acid at position 194 in the amino acid sequence as shown in SEQ ID NO: 1 is lysine, arginine, histidine, alanine, leucine, isoleucine, valine, or cysteine.

2. The modified amadoriase according to claim 1, (A) comprising one or more of the following:

(a) an amino acid sequence in which, when aligned with the amino acid sequence as shown in SEQ ID NO: 1, the amino acid at the position corresponding to lysine at position 80 in the amino acid sequence as shown in SEQ ID NO: 1 is arginine, asparagine, glutamine, or histidine;

(b) an amino acid sequence in which, when aligned with the amino acid sequence as shown in SEQ ID NO: 1, the amino acid at the position corresponding to glutamic acid at position 175 in the amino acid sequence as shown in SEQ ID NO: 1 is arginine, lysine, or histidine;

(c) an amino acid sequence in which, when aligned with the amino acid sequence as shown in SEQ ID NO: 1, the amino acid at the position corresponding to phenylalanine at position 172 in the amino acid sequence as shown in SEQ ID NO: 1 is glutamic acid, aspartic acid, tyrosine, or glutamine;

(d) an amino acid sequence in which, when aligned with the amino acid sequence as shown in SEQ ID NO: 1, the amino acid at the position corresponding to valine at position 279 in the amino acid sequence as shown in SEQ ID NO: 1 is isoleucine or cysteine;

(e) an amino acid sequence in which, when aligned with the amino acid sequence as shown in SEQ ID NO: 1, the amino acid at the position corresponding to valine at position 12 in the amino acid sequence as shown in SEQ ID NO: 1 is isoleucine or leucine;

(f) an amino acid sequence in which, when aligned with the amino acid sequence as shown in SEQ ID NO: 1, the amino acid at the position corresponding to arginine at position 9 in the amino acid sequence as shown in SEQ ID NO: 1 is threonine, asparagine, or glutamine;

(g) an amino acid sequence in which, when aligned with the amino acid sequence as shown in SEQ ID NO: 1, the amino acid at the position corresponding to glutamine at position 77 in the amino acid sequence as shown in SEQ ID NO: 1 is aspartic acid, glutamic acid, lysine, or asparagine;

(h) an amino acid sequence in which, when aligned with the amino acid sequence as shown in SEQ ID NO: 1, the amino acid at the position corresponding to serine at position 30 in the amino acid sequence as shown in SEQ ID NO: 1 is threonine or valine;

(i) an amino acid sequence in which, when aligned with the amino acid sequence as shown in SEQ ID NO: 1, the amino acid at the position corresponding to valine at position 28 in the amino acid sequence as shown in SEQ ID NO: 1 is isoleucine or methionine;

(j) an amino acid sequence in which, when aligned with the amino acid sequence as shown in SEQ ID NO: 1, the amino acid at the position corresponding to valine at position 13 in the amino acid sequence as shown in SEQ ID NO: 1 is leucine;

(k) an amino acid sequence in which, when aligned with the amino acid sequence as shown in SEQ ID NO: 1, the amino acid at the position corresponding to phenylalanine at position 286 in the amino acid sequence as shown in SEQ ID NO: 1 is tyrosine;

(l) an amino acid sequence in which, when aligned with the amino acid sequence as shown in SEQ ID NO: 1, the amino acid at the position corresponding to glutamic acid at position 204 in the amino acid sequence as shown in SEQ ID NO: 1 is alanine;

(m) an amino acid sequence in which, when aligned with the amino acid sequence as shown in SEQ ID NO: 1, the amino acid at the position corresponding to aspartic acid at position 338 in the amino acid sequence as shown in SEQ ID NO: 1 is alanine; and (n) an amino acid sequence in which, when aligned with the amino acid sequence as shown in SEQ ID NO: 1, the amino acid at the position corresponding to aspartic acid at position 194 in the amino acid sequence as shown in SEQ ID NO: 1 is lysine or alanine;

or (B) further comprising the following:

(a) an amino acid sequence in which, when aligned with the amino acid sequence as shown in SEQ ID NO: 1, the amino acid at the position corresponding to methionine at position 71 in the amino acid sequence as shown in SEQ ID NO: 1 is isoleucine, alanine, glycine, valine, or cysteine.

3. The modified amadoriase according to claim 2, comprising an amino acid sequence in which, when aligned with the amino acid sequence as shown in SEQ ID NO: 1, the amino acid at the position corresponding to position 80 and the amino acid at the position corresponding to position 71 in the amino acid sequence as shown in SEQ ID NO: 1 are substituted and having activity on α-fructosyl valine (αFV) or α-fructosyl-valyl-histidine (αFVH).

4. The modified amadoriase according to claim 3, further comprising an amino acid sequence in which, when aligned with the amino acid sequence as shown in SEQ ID NO: 1, the amino acid at the position corresponding to position 77 in the amino acid sequence as shown in SEQ ID NO: 1 is substituted and having activity on α-fructosyl valine (αFV) or α-fructosyl-valyl-histidine (αFVH).

5. The modified amadoriase according to claim 1, comprising an amino acid sequence in which, when aligned with the amino acid sequence as shown in SEQ ID NO: 1, the amino acid at the position corresponding to position 175 and the amino acid at the position corresponding to position 172 in the amino acid sequence as shown in SEQ ID NO: 1 are substituted and having activity on α-fructosyl valine (αFV) or α-fructosyl-valyl-histidine (αFVH).

6. The modified amadoriase according to claim 1, comprising an amino acid sequence in which, when aligned with the amino acid sequence as shown in SEQ ID NO: 1, the amino acid at the position corresponding to position 30 and the amino acid at the position corresponding to position 28 in the amino acid sequence as shown in SEQ ID NO: 1 are substituted and having activity on α-fructosyl valine (αFV) or α-fructosyl-valyl-histidine (αFVH).

7. The modified amadoriase according to claim 1, comprising an amino acid sequence in which, when aligned with the amino acid sequence as shown in SEQ ID NO: 1, the amino acid at the position corresponding to position 12, the amino acid at the position corresponding to position 9, the amino acid at the position corresponding to position 13, the amino acid at the position corresponding to position 3, and the amino acid at the position corresponding to position 4 in the amino acid sequence as shown in SEQ ID NO: 1 are substituted and having activity on α-fructosyl valine (αFV) or α-fructosyl-valyl-histidine (αFVH).

8. The modified amadoriase according to claim 1, which is derived from the genus *Coniochaeta*.

9. The modified amadoriase according to claim 1, comprising the amino acid sequence as shown in SEQ ID NO: 1, SEQ ID NO: 6, SEQ ID NO: 10, SEQ ID NO: 11, SEQ ID NO: 94, or SEQ ID NO: 110, wherein said amadoriase further comprises an amino acid substitution as defined in claim 1.

10. An amadoriase gene encoding a modified amadoriase comprising the amino acid sequence according to claim 1.

11. A method for producing an amadoriase comprising the following steps:

(i) culturing a host cell transduced with the gene according to claim 10;

(ii) expressing the amadoriase gene contained in the host cell; and (iii) isolating the amadoriase from a culture product.

12. A composition for use in measuring glycated hemoglobin comprising the modified amadoriase according to claim 1.

13. The composition according to claim 12, which comprises one or more anionic surfactants.

14. The composition according to claim 13, wherein the anionic surfactant is one or more anionic surfactant selected from the group consisting of the following compounds:

a sulfuric ester compound represented by Formula (I):

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a benzene sulfonic acid salt compound represented by Formula (II):

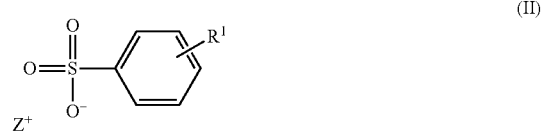

wherein $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

an acyl sarcosine acid salt compound represented by Formula (III):

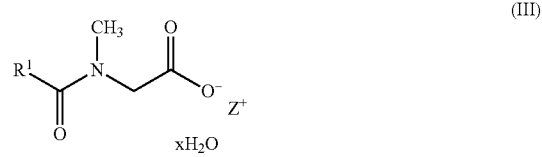

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a phosphonic acid salt compound represented by Formula (IV):

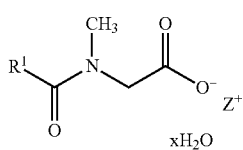 (III)

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a sulfosuccinic acid salt compound represented by Formula (V):

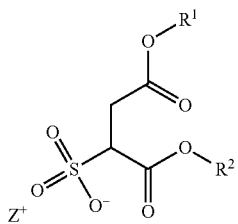 (V)

wherein, $R^1$ and $R^2$ each independently represent substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a carboxylic acid salt compound represented by Formula (VI):

$$R^1\text{—COO}^-Z^+ \quad (VI)$$

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion;

a sulfonic acid salt compound represented by Formula (VII):

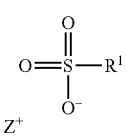 (VII)

wherein, $R^1$ represents substituted or unsubstituted and linear or branched $C_1$ to $C_{30}$ alkyl or $C_3$ to $C_{30}$ cyclic alkyl, linear or branched $C_2$ to $C_{30}$ alkenyl, $C_3$ to $C_{30}$ cyclic alkenyl, $C_6$ to $C_{30}$ aryl, or $C_7$ to $C_{30}$ arylene; and $Z^+$ represents a counter ion; and cholic acid salt, deoxycholic acid salt, glycocholic acid salt, taurocholic acid salt, taurodeoxycholic acid salt, acylglutamic acid salt, acylmethyl alanine salt, acylglycine salt, acylmethyl taurine salt, and a derivative of any thereof.

15. A method for measuring α-fructosyl valine (αFV) or α-fructosyl-valyl-histidine (αFVH) in a sample comprising contacting a sample comprising α-fructosyl valine (αFV) or α-fructosyl-valyl-histidine (αFVH) with a surfactant and the amadoriase according to claim 1, wherein the amadoriase acts on α-fructosyl valine (αFV) or α-fructosyl-valyl-histidine (αFVH), and measuring hydrogen peroxide generated or oxygen consumed from the contact.

16. The composition according to claim 12, comprising sodium cholate or sodium deoxycholate.

17. The composition according to claim 16, wherein the residual activity (%) of the amadoriase that was allowed to stand at 30° C. for 5 minutes after sodium cholate had been added to a final concentration of 0.5 to 1.5% (w/v) is 100% or more, compared with the case in which no sodium cholate had been added (100%), or the residual activity of the amadoriase that was allowed to stand at 30° C. for 5 minutes after sodium deoxycholate had been added to a final concentration of 0.3 to 2.0% (w/v) is 100% or more, compared with the case in which no sodium deoxycholate is added (100%).

* * * * *

SEQUENCE LISTING

<160> NUMBER OF SEQ ID NOS: 137

<210> SEQ ID NO 1
<211> LENGTH: 437
<212> TYPE: PRT
<213> ORGANISM: Coniochaeta sp.

<400> SEQUENCE: 1

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
```

405                 410                 415
Arg Arg Ala Ala Pro Pro Lys Asp Leu Ala Asp Met Pro Gly Trp Lys
            420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaagggtg attgtcgtcg gtggcggagg aacgattggt    60
tcctcgacag cgctgcatct tgtgaggagt ggttatgctc ccgcaaatat cacggtcttg   120
gacacatttg agattccatc ggctcaatca gccggccatg atctcaacaa gatcatggga   180
atacgactgc gcaacaaggt ggacctgcaa atgagtctag aggctagaca gatgtggaag   240
gaggatgagt tattccagcc cttctttcac aataccggca gaatggactg cgaacacacg   300
cctgagggta tcgaggacct gaaaaagcag taccaggcac tgcacgatgc cggtgcgggt   360
ctggagaaga ctcatgcctg gttggacaac gaggatgaga tcttatccaa gatgccgttg   420
cttcaacgtg accaaataca aggatggaaa gcaatatgga gtcaagatgg cggctggtta   480
gctgcggcaa aggccatcaa tgcgatcgga cagttcttga agaacgtggt gtaaagttc    540 ggattcggcg gcgctggatc cttcaagcaa cccctttttcg acgatgaagg cacaacttgc   600
attggcgttg agacggcaga tggtaccaaa tattacgctg acaaggtggt cttagcagct   660
ggcgcatgga gcccaaccct ggtggacctg aagatcaat gttgctcgaa ggcttgggtg   720
tatgctcata ttcagttgac gcctgaagag gccgctgagt ataagggtgt cccagttgtg   780
tataatggcg aatttggctt cttctttgag cctgatgagt ttggtgtaat aaaggtgtgc   840
gacgagttcc caggattctc gcgcttcaag gaacatcaac cctatggcgc cccatctccg   900
aaacggatat cagtaccacg atcgcacgcc aagcatccca cagacactta ccagacgca   960 tccgaagtca gcatcaaaaa agcaatcgcg acgtttctcc ctcgatttca ggacaaggag  1020
ctcttcaatc gcgccttgtg ctggtgtaca gacactgcgg acgctgctct cttgatgtgt  1080
gaacacccca atggaagaa tttcattcta gcgaccggcg acagcggaca ctcattcaaa  1140
atcttgccta acgtcggaaa atacgtagtc gagttgatag agggccgcct gccggaggaa  1200
atggcttatc aatggaggtg gcggccagga ggcgatgcac tcaagtctag acgtgcggca  1260
ccgccaaaag atcttgcaga catgccagga tggaaacatg atccgaaatt gtaa        1314

<210> SEQ ID NO 3
<211> LENGTH: 437
<212> TYPE: PRT
<213> ORGANISM: Eupenicillium terrenum

<400> SEQUENCE: 3

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Val Leu Ala Ala Gly Ala Trp Ser
210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Glu Pro Asp
            260                 265                 270

Glu Tyr Gly Val Ile Lys Val Cys Asp Glu Phe Pro Gly Phe Ser Arg
            275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Leu Leu Pro Asn
            370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 4
<211> LENGTH: 440
<212> TYPE: PRT
<213> ORGANISM: Pyrenochaeta sp.

```
<400> SEQUENCE: 4

Met Ala Ala Ser Arg Ala Lys Thr Thr Val Ile Val Val Gly Gly
1               5                   10                  15

Gly Thr Ile Gly Ser Ser Thr Ala Leu His Leu Leu Arg Ser Gly Tyr
                20                  25                  30

Thr Pro Ser Asn Ile Thr Val Leu Asp Thr Tyr Pro Ile Pro Ser Leu
            35                  40                  45

Gly Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
    290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415
```

Arg Ala Ala Pro Ala Lys Asp Leu Ala Asp Met Pro Gly Trp Asn His
            420                 425                 430
Asp Glu Ser Pro Arg Ala Lys Leu
            435                 440

<210> SEQ ID NO 5
<211> LENGTH: 452
<212> TYPE: PRT
<213> ORGANISM: Arthrinium sp.

<400> SEQUENCE: 5

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp

```
                      340                 345                 350
Thr Ala Asp Ala Ala Leu Leu Ile Cys Glu His Pro Arg Trp Arg Asn
            355                 360                 365

Phe Ile Leu Ala Thr Gly Asp Ser Gly His Ser Phe Lys Leu Leu Pro
        370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450

<210> SEQ ID NO 6
<211> LENGTH: 440
<212> TYPE: PRT
<213> ORGANISM: Curvularia clavata

<400> SEQUENCE: 6

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
                245                 250                 255
```

```
Val Val Tyr Asn Gly Asp Val Gly Phe Phe Glu Pro Asp Glu His
            260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
            290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
            355                 360                 365

Ala Thr Gly Asp Ser Gly His Thr Phe Lys Leu Leu Pro Asn Ile Gly
            370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
            435                 440

<210> SEQ ID NO 7
<211> LENGTH: 441
<212> TYPE: PRT
<213> ORGANISM: Neocosmospora vasinfecta

<400> SEQUENCE: 7

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
            115                 120                 125

Asp Ser Glu Glu Ala Ile Leu Glu Lys Ala Pro Leu Leu Gln Arg Glu
            130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Ala Gly Ser Phe Lys Arg Pro Leu
            180                 185                 190
```

```
Phe Ala Asp Asp Gly Thr Thr Cys Ile Gly Val Glu Thr Val Asp Gly
            195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
                260                 265                 270

Glu Asn Gly Val Ile Lys Val Cys Asp Glu Phe Pro Gly Phe Thr Arg
                275                 280                 285

Phe Lys Gln His Gln Pro Tyr Gly Ala Pro Ala Lys Pro Val Ser
            290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
            355                 360                 365

Ile Leu Ala Thr Gly Asp Ser Gly His Ser Phe Lys Leu Leu Pro Ile
            370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
            435                 440

<210> SEQ ID NO 8
<211> LENGTH: 477
<212> TYPE: PRT
<213> ORGANISM: Cryptococcus neoformans

<400> SEQUENCE: 8

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
            35                  40                  45

Gln Ser Ala Gly Asn Asp Leu Asn Lys Ile Met Gly Ile Arg Ile Arg
        50                  55                  60

Asn Pro Val Asp Lys Gln Leu Ser Leu Glu Ala Arg Asp Met Trp Arg
65              70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
```

```
            115                 120                 125
Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
                195                 200                 205

Thr Gln Tyr Phe Ala Asp Lys Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Glu Tyr Lys Glu
                245                 250                 255

Cys Pro Val Val Tyr Asn Ser Glu Leu Gly Phe Phe Glu Pro Asn
                260                 265                 270

Glu Lys Gly Val Ile Lys Val Cys Asp Glu Phe Pro Gly Phe Thr Arg
                275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
                340                 345                 350

Ala Asp Ala Asn Leu Leu Ile Cys Glu His Pro Lys Trp Lys Asn Phe
                355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
                420                 425                 430

Asn His Asp Glu Pro Ser Asp Asp Met Asp Val Lys Asp Val Ala
                435                 440                 445

Val Ser Leu Ala Ser Val Lys Ile Gly Glu Asn Ile Gly Glu Lys Val
    450                 455                 460

Val Glu Asp Gly Ala Arg Val Gly Val Lys Val Leu Ala
465                 470                 475

<210> SEQ ID NO 9
<211> LENGTH: 437
<212> TYPE: PRT
<213> ORGANISM: Phaeosphaeria nodorum

<400> SEQUENCE: 9

Met Ala Pro Ser Arg Ala Asn Thr Ser Val Ile Val Val Gly Gly Gly
1               5                  10                  15
```

```
Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Ser Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
```

-continued

435

<210> SEQ ID NO 10
<211> LENGTH: 438
<212> TYPE: PRT
<213> ORGANISM: Aspergillus nidulans

<400> SEQUENCE: 10

Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 11
<211> LENGTH: 438
<212> TYPE: PRT
<213> ORGANISM: Emericella nidulans

<400> SEQUENCE: 11

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
                115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

```
Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 12
<211> LENGTH: 441
<212> TYPE: PRT
<213> ORGANISM: Ulocladium sp.

<400> SEQUENCE: 12

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
```

```
                225                 230                 235                 240
His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
                260                 265                 270

Gly Val Ile Lys Val Cys Asp Glu Phe Pro Gly Phe Thr Arg Phe Lys
                275                 280                 285

Gln His Gln Pro Phe Gly Ala Ser Ala Pro Lys Arg Ile Ser Val Pro
                290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
                340                 345                 350

Ala Ala Leu Leu Met Cys Glu His Pro Glu Trp Lys Asn Phe Val Leu
                355                 360                 365

Ala Thr Gly Asp Ser Gly His Thr Phe Lys Leu Leu Pro Asn Ile Gly
                370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
                420                 425                 430

Asp Gly Glu Ala Pro Arg Ala Lys Leu
                435                 440

<210> SEQ ID NO 13
<211> LENGTH: 437
<212> TYPE: PRT
<213> ORGANISM: Penicillium janthinellum

<400> SEQUENCE: 13

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
                20                  25                  30

Thr Pro Ser Asn Ile Thr Val Leu Asp Val Tyr Pro Ile Pro Ser Leu
                35                  40                  45

Gln Ser Ala Gly Tyr Asp Leu Asn Lys Ile Met Ser Ile Arg Leu Arg
            50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
                100                 105                 110

Asp Leu Ile Asp Ala Asn Ile Gly Leu Glu Lys Thr Asn Ile Trp Leu
            115                 120                 125

Glu Ser Glu Asp Asp Ile Leu Ala Lys Ala Pro His Phe Thr Arg Glu
        130                 135                 140

Gln Ile Lys Gly Trp Lys Gly Leu Phe Cys Gly Asp Gly Gly Trp Leu
145                 150                 155                 160
```

```
Ala Ala Ala Lys Ala Ile Asn Ala Ile Gly Thr Phe Leu Lys Ser Gln
            165                 170                 175

Gly Val Lys Phe Gly Phe Gly Ser Ala Gly Thr Phe Lys Arg Pro Leu
        180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
        210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
        290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
        370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
cgtgcagata caaccgtgat tgtcgtcggt                                        30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
aatcgttcct ccgccaccga cgacaatcac                                        30
```

```
<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
acaagggtga ttattgtcgg tggcggagga                              30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tgtcgaggaa ccaatcgttc ctccgccacc                              30

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gtggacctgc aactgagtct agaggctaga                              30

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
ctccttccac atctgtctag cctctagact                              30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
agacagatgt ggcgtgagga tgagttattc                              30

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
gtgaaagaag ggctggaata actcatcctc                              30

<210> SEQ ID NO 22
<211> LENGTH: 30
<212> TYPE: DNA
<213> ORGANISM: Artificial
<220> FEATURE:
<223> OTHER INFORMATION: primer
```

```
<400> SEQUENCE: 22
gcgatcggac aggaattgaa agaacgtggt                                      30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
gaatccgaac tttacaccac gttctttcaa                                      30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
ggacagttct tgaaacgtcg tggtgtaaag                                      30

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
gccgaatccg aactttacac cacg                                            24

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tttggtgtaa taaagatttg cgacgaattc                                      30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
gaagcgcgag aatcctggga attcgtcgca                                      30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
gcgctgcatc ttctgaggag tggttatgct                                      30

<210> SEQ ID NO 29
<211> LENGTH: 27
```

```
<212> TYPE: DNA
<213> ORGANISM: Artificial
<220> FEATURE:
<223> OTHER INFORMATION: primer

<400> SEQUENCE: 29
gatatttgcg ggagcataac cactcct                                        27

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
catcttgtga gggcgggtta tgctcccgca                                     30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
caagaccgtg atatttgcgg gagcataacc                                     30

<210> SEQ ID NO 32
<211> LENGTH: 30
<212> TYPE: DNA
<213> ORGANISM: Artificial
<220> FEATURE:
<223> OTHER INFORMATION: primer

<400> SEQUENCE: 32
ctagaggcta gagatatgtg gaaggaggat                                     30

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
gggctggaat aactcatcct ccttccacat                                     30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
ttggacacat atccgattcc atcggctcaa                                     30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
```

-continued catggccggc tgattgagcc gatggaat                28

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
caatcagccg gcaacgatct caacaagatc              30

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
gtcgtattcc catgatcttg ttgagat                 27

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
tttcaggaca agccgctctt caatcgcgcc              30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
tgtacaccag cacaaggcgc gattgaagag              30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
ggacaggaat tgaaacgtcg tggtgtaaag              30

<210> SEQ ID NO 41
<211> LENGTH: 30
<212> TYPE: DNA
<213> ORGANISM: Artificial
<220> FEATURE:
<223> OTHER INFORMATION: primer

<400> SEQUENCE: 41
catcttctga gggcgggtta tgctcccgca              30

<210> SEQ ID NO 42
<211> LENGTH: 32
<212> TYPE: DNA
<213> ORGANISM: Artificial

```
<220> FEATURE:
<223> OTHER INFORMATION: primer

<400> SEQUENCE: 42
gctagagata tgtggcgtga ggatgagtta tt                            32

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
atcctcacgc cacatatctc tagcctctag                               30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
cgtgcagata caaccgtgat tattattggt                               30

<210> SEQ ID NO 45
<211> LENGTH: 30
<212> TYPE: DNA
<213> ORGANISM: Artificial
<220> FEATURE:
<223> OTHER INFORMATION: primer

<400> SEQUENCE: 45
aatcgttcct ccgccaccaa taataatcac                               30

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
gaattatgac gtcgccgcgt gcagatacaa                               30

<210> SEQ ID NO 47
<211> LENGTH: 28
<212> TYPE: DNA
<213> ORGANISM: Artificial
<220> FEATURE:
<223> OTHER INFORMATION: primer

<400> SEQUENCE: 47
caataataat cacggttgta tctgcacg                                 28

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
gcaatatggg atcaagatgg cggctggtta                               30
```

```
<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ggcctttgcc gcagctaacc agccgccatc                                30

<210> SEQ ID NO 50
<211> LENGTH: 27
<212> TYPE: DNA
<213> ORGANISM: Artificial
<220> FEATURE:
<223> OTHER INFORMATION: primer

<400> SEQUENCE: 50
gagtataagg gttgcccagt tgtgtat                                   27

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51
aagccaaatt cgccatgata cacaactgg                                 29

<210> SEQ ID NO 52
<211> LENGTH: 29
<212> TYPE: DNA
<213> ORGANISM: Artificial
<220> FEATURE:
<223> OTHER INFORMATION: primer

<400> SEQUENCE: 52
gatggaaaca tgattaaaat ccatatgac                                 29

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53
tcatatggat tttaatcatg tttccatcc                                 29

<210> SEQ ID NO 54
<211> LENGTH: 30
<212> TYPE: DNA
<213> ORGANISM: Artificial
<220> FEATURE:
<223> OTHER INFORMATION: primer

<400> SEQUENCE: 54
accggcagaa tggactgcgc acacacgcct                                30

<210> SEQ ID NO 55
<211> LENGTH: 30
<212> TYPE: DNA
<213> ORGANISM: Artificial
<220> FEATURE:
<223> OTHER INFORMATION: primer
```

<400> SEQUENCE: 55
tttcaggtcc tcgataccct caggcgtgtg                                              30

<210> SEQ ID NO 56
<211> LENGTH: 30
<212> TYPE: DNA
<213> ORGANISM: Artificial
<220> FEATURE:
<223> OTHER INFORMATION: primer

<400> SEQUENCE: 56
cgtgcagata caagggtgat tattattggt                                              30

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
aatcgttcct ccgccaccaa taataatcac                                              30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
acaaccgtga ttgtcattgg tggcggagga                                              30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
tgtcgaggaa ccaatcgttc ctccgccacc                                              30

<210> SEQ ID NO 60
<211> LENGTH: 30
<212> TYPE: DNA
<213> ORGANISM: Artificial
<220> FEATURE:
<223> OTHER INFORMATION: primer

<400> SEQUENCE: 60
accgtgatta ttgtcggtgg cggaggaacg                                              30

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
aatcacccrt gtatctgcac gattcgacgt                                              30

<210> SEQ ID NO 62

```
<211> LENGTH: 30
<212> TYPE: DNA
<213> ORGANISM: Artificial
<220> FEATURE:
<223> OTHER INFORMATION: primer

<400> SEQUENCE: 62
atacaagggt gattctcgtc ggtggcggag                                30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
gacaatcacc cttgtatctg cacgattcga                                30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
caagggtgat tgtcctcggt ggcggaggaa                                30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
aagatgcagc gctgtcgagg aaccaatcgt                                30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
cagcgctgca tcttattagg agtggttatg                                30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
cagcgctgca tcttatgagg agtggttatg                                30

<210> SEQ ID NO 68
<211> LENGTH: 30
<212> TYPE: DNA
<213> ORGANISM: Artificial
<220> FEATURE:
<223> OTHER INFORMATION: primer

<400> SEQUENCE: 68
```
cctcacaaga tgcagcgctg tcgaggaacc    30

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
tgcatcttgt gaggactggt tatgctcccg    30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
tgcatcttgt gagggttggt tatgctcccg    30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
ttgcaggtcc accttgttgc gcagtcgtat    30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
aggtggacct gcaaattagt ctagaggcta    30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
aggtggacct gcaagcgagt ctagaggcta    30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
aggtggacct gcaagtgagt ctagaggcta    30

<210> SEQ ID NO 75
<211> LENGTH: 30
<212> TYPE: DNA

```
<213> ORGANISM: Artificial
<220> FEATURE:
<223> OTHER INFORMATION: primer

<400> SEQUENCE: 75
aggtggacct gcaatgcagt ctagaggcta                               30

<210> SEQ ID NO 76
<211> LENGTH: 30
<212> TYPE: DNA
<213> ORGANISM: Artificial
<220> FEATURE:
<223> OTHER INFORMATION: primer

<400> SEQUENCE: 76
tctagcctct agactcattt gcaggtccac                               30

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77
gtctagaggc tagagagatg tggaaggagg                               30

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
gtctagaggc tagaaagatg tggaaggagg                               30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
gtctagaggc tagaaagatg tggaaggagg                               30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
gtctagaggc tagaaacatg tggaaggagg                               30

<210> SEQ ID NO 81
<211> LENGTH: 30
<212> TYPE: DNA
<213> ORGANISM: Artificial
<220> FEATURE:
<223> OTHER INFORMATION: primer

<400> SEQUENCE: 81
ccacatctgt ctagcctcta gactcatttg                               30
```

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
ctagacagat gtggaacgag gatgagttat                                  30

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
ctagacagat gtggcaggag gatgagttat                                  30

<210> SEQ ID NO 84
<211> LENGTH: 30
<212> TYPE: DNA
<213> ORGANISM: Artificial
<220> FEATURE:
<223> OTHER INFORMATION: primer

<400> SEQUENCE: 84
ctagacagat gtggcatgag gatgagttat                                  30

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
ctgtccgatc gcattgatgg cctttgccgc                                  30

<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
atgcgatcgg acaggacttg aaagaacgtg                                  30

<210> SEQ ID NO 87
<211> LENGTH: 30
<212> TYPE: DNA
<213> ORGANISM: Artificial
<220> FEATURE:
<223> OTHER INFORMATION: primer

<400> SEQUENCE: 87
atgcgatcgg acagtacttg aaagaacgtg                                  30

<210> SEQ ID NO 88
<211> LENGTH: 30
<212> TYPE: DNA
<213> ORGANISM: Artificial
<220> FEATURE:

<223> OTHER INFORMATION: primer

<400> SEQUENCE: 88
atgcgatcgg acagcagttg aaagaacgtg                30

<210> SEQ ID NO 89
<211> LENGTH: 30
<212> TYPE: DNA
<213> ORGANISM: Artificial
<220> FEATURE:
<223> OTHER INFORMATION: primer

<400> SEQUENCE: 89
tttcaagaac tgtccgatcg cattgatggc                30

<210> SEQ ID NO 90
<211> LENGTH: 30
<212> TYPE: DNA
<213> ORGANISM: Artificial
<220> FEATURE:
<223> OTHER INFORMATION: primer

<400> SEQUENCE: 90
gacagttctt gaaaaaacgt ggtgtaaagt                30

<210> SEQ ID NO 91
<211> LENGTH: 30
<212> TYPE: DNA
<213> ORGANISM: Artificial
<220> FEATURE:
<223> OTHER INFORMATION: primer

<400> SEQUENCE: 91
gacagttctt gaaacatcgt ggtgtaaagt                30

<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92
ctttattaca ccaaactcat caggctcaaa                30

<210> SEQ ID NO 93
<211> LENGTH: 30
<212> TYPE: DNA
<213> ORGANISM: Artificial
<220> FEATURE:
<223> OTHER INFORMATION: primer

<400> SEQUENCE: 93
ttggtgtaat aaagtgctgc gacgagttcc                30

<210> SEQ ID NO 94
<211> LENGTH: 440
<212> TYPE: PRT
<213> ORGANISM: Curvularia clavata

<400> SEQUENCE: 94

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

```
Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
 50                  55                  60

Asn Lys Val Asp Leu Gln Leu Ser Leu Glu Ala Arg Gln Met Trp Arg
 65                  70                  75                  80

Glu Asp Asp Leu Phe Lys Glu Tyr Phe His Asn Thr Gly Arg Leu Asp
                 85                  90                  95

Cys Ala His Gly Glu Gly Leu Ala Asp Leu Arg Gln Ala Tyr Gln
                100                 105                 110

Ala Leu Leu Asp Ala Asn Ala Gly Leu Glu Thr Thr Glu Trp Leu
            115                 120                 125

Asp Ser Glu Asp Glu Ile Leu Lys Lys Met Pro Leu Leu Asp Arg Glu
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Gly Ala Trp Ser Pro Val
210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
            290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
                340                 345                 350

Ala Ala Leu Leu Met Cys Glu His Pro Glu Trp Lys Asn Phe Val Leu
            355                 360                 365

Ala Thr Gly Asp Ser Gly His Thr Phe Lys Leu Leu Pro Asn Ile Gly
            370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
            435                 440
```

```
<210> SEQ ID NO 95
<211> LENGTH: 1323
<212> TYPE: DNA
<213> ORGANISM: Curvularia clavata

<400> SEQUENCE: 95
atggccccga gtcgcgctaa cacgagcgtc attgtggtgg gtggtggtgg cacgattggt      60
tcctcaacgg cactgcatct ggtccgtagc ggctataccc cgtctaacat taccgtgctg     120
gacacgtacc cgatcccgag cgcccagtct gcaggcaacg atctgaataa aattatgggt     180
atccgtctgc gcaacaaagt tgatctgcag ctgtcactgg aagcccgtca atgtggcgc      240 gaagatgacc tgtttaaaga atacttccat aacaccggcc gtctggattg cgcacacggt     300
gaagaaggtc tggccgacct cgcccaggct taccaagcgc tgctggatgc caacgcaggt     360
ctggaagaaa ccacggaatg gctggattca gaagacgaaa ttctgaagaa aatgccgctg     420
ctggatcgtg aacagatcaa aggttggaaa gccgtgtatt cgcaagatgg cggttggctg     480
gcggccgcaa aagccattaa tgcaatcggc gaatacctgc gcgcgcaggg cgttaaattc     540
ggttttggcg gtgctggttc ctttaaacag ccgctgctgg cagaaggcgt ctgcattggt     600
gtcgaaaccg tggatggcac gcgttattac gcggacaaag tggttctggc tgcaggtgca     660
tggagtccgg tgctggttga tctggaagac cagtgtgtgt ccaaagcgtg ggtttatgcg     720
catatccaac tgaccccgga agaagccgca gaatataaaa acgtcccggt cgtgtacaat     780
ggcgatgtgg gcttttttctt tgaaccggac gaacatggcg ttattaaagt ctgcgatgaa     840
tttccgggtt ttacccgctt caaacagcac caaccgtatg cgctaaagc gccgaaacgt     900 atctcagtgc gcgttcggc tgcaaaacac ccgaccgata cgtacccgga cgcgagtgaa     960
aaatccattc gtaaagccat cgcaacccttt ctgccgaaat tcacggaaaa agaactgttt    1020
aatcgccatc tgtgctggtg taccgatacg gccgacgccg cactgctgat gtgtgaacac    1080
ccggaatgga aaaactttgt tctggcgacc ggcgatagcg gtcatacgtt caaactgctg    1140
ccgaatattg gcaaacacgt tgtcgaactg ctggaaggta ccctggcaga agacctggct    1200
catgcgtggc gttggcgtcc gggtacgggt gatgcactga atctcgtcg cgctgcgccg    1260 gcgaaagacc tggcggatat gccgggctgg aaacacgacg atgtggtgaa aagcaaactg    1320
taa                                                                   1323

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
cagatgcagt gccgttgagg aaccaatcgt                                        30

<210> SEQ ID NO 97
<211> LENGTH: 30
<212> TYPE: DNA
<213> ORGANISM: Artificial
<220> FEATURE:
<223> OTHER INFORMATION: primer

<400> SEQUENCE: 97
ctccgtagcg gctataccccc gtctaacatt                                       30
```

```
<210> SEQ ID NO 98
<211> LENGTH: 30
<212> TYPE: DNA
<213> ORGANISM: Artificial
<220> FEATURE:
<223> OTHER INFORMATION: primer

<400> SEQUENCE: 98
atgcgtagcg gctataccccc gtctaacatt                                    30

<210> SEQ ID NO 99
<211> LENGTH: 30
<212> TYPE: DNA
<213> ORGANISM: Artificial
<220> FEATURE:
<223> OTHER INFORMATION: primer

<400> SEQUENCE: 99
ctgcagatca actttgttgc gcagacggat                                     30

<210> SEQ ID NO 100
<211> LENGTH: 30
<212> TYPE: DNA
<213> ORGANISM: Artificial
<220> FEATURE:
<223> OTHER INFORMATION: primer

<400> SEQUENCE: 100
gcgtcactgg aagcccgtca aatgtggcgc                                     30

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
gtgtcactgg aagcccgtca aatgtggcgc                                     30

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102
ccacatttga cgggcttcca gtgacagctg                                     30

<210> SEQ ID NO 103
<211> LENGTH: 30
<212> TYPE: DNA
<213> ORGANISM: Artificial
<220> FEATURE:
<223> OTHER INFORMATION: primer

<400> SEQUENCE: 103
aacgaagatg acctgtttaa agaatacttc                                     30

<210> SEQ ID NO 104
<211> LENGTH: 30
<212> TYPE: DNA
<213> ORGANISM: Artificial
<220> FEATURE:
<223> OTHER INFORMATION: primer
```

```
<400> SEQUENCE: 104
caggaagatg acctgtttaa agaatacttc                                30

<210> SEQ ID NO 105
<211> LENGTH: 30
<212> TYPE: DNA
<213> ORGANISM: Artificial
<220> FEATURE:
<223> OTHER INFORMATION: primer

<400> SEQUENCE: 105
ttcgccgatt gcattaatgg cttttgcggc                                30

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
gaactgcgcg cgcagggcgt taaattcggt                                30

<210> SEQ ID NO 107
<211> LENGTH: 30
<212> TYPE: DNA
<213> ORGANISM: Artificial
<220> FEATURE:
<223> OTHER INFORMATION: primer

<400> SEQUENCE: 107
gacctgcgcg cgcagggcgt taaattcggt                                30

<210> SEQ ID NO 108
<211> LENGTH: 30
<212> TYPE: DNA
<213> ORGANISM: Artificial
<220> FEATURE:
<223> OTHER INFORMATION: primer

<400> SEQUENCE: 108
gcgcaggtat tcgccgattg cattaatggc                                30

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
aagcagggcg ttaaattcgg ttttggcggt                                30

<210> SEQ ID NO 110
<211> LENGTH: 438
<212> TYPE: PRT
<213> ORGANISM: Emericella nidulans

<400> SEQUENCE: 110

Met Ala Pro Arg Ala Asn Thr Lys Ile Ile Val Val Gly Gly Gly
 1               5                  10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
```

```
                35                  40                  45
Ser Ala Gly Tyr Asp Leu Asn Lys Ile Phe Gly Ile Ser Gly Ala Asn
 50                  55                  60

Lys His Asp Leu Gln Leu Ser Leu Glu Ala Phe Asp Met Trp Lys Asn
 65                  70                  75                  80

Asp Pro Leu Phe Lys Pro Phe Phe His Asn Val Gly Gln Met Asp Val
                 85                  90                  95

Ser Ser Thr Glu Glu Gly Ile Lys Arg Leu Arg Arg Tyr Gln Ser
                100                 105                 110

Leu Leu Arg Ala Gly Ile Gly Leu Glu Lys Thr Asn Phe Leu Leu Glu
                115                 120                 125

Ser Glu Asp Glu Ile Leu Ala Lys Ala Pro His Phe Thr Arg Glu Gln
                130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                    165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                    245                 250                 255

Thr Pro Val Ile Tyr Asp Gly Asp Tyr Gly Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
                290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ser Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                    405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 111
```

```
<211> LENGTH: 1317
<212> TYPE: DNA
<213> ORGANISM: Emericella nidulans

<400> SEQUENCE: 111
atggctccgc gtgcgaatac gaaaatcatt gttgtcggtg gtggtggtac gatgggttca      60
agtacggctc tgcatctgct gcgtgcgggc tatacccccga gcaacattac cgtgctggat    120
acgtatccga tcccgtcagc gcagtcggcc ggttacgacc tgaacaaaat tttttggtatc    180
agcggtgcaa ataaacatga tctgcaactg tctctggaag cgtttgatat gtggaaaaac    240
gacccgctgt ttaaaccgtt tttccacaat gtgggccaga tggatgttag ctctaccgaa    300
gaaggtatta aacgcctgcg tcgccgttac caaagtctgc tgcgtgccgg catcggtctg    360
gaaaaaacca acttcctgct ggaatccgaa gatgaaattc tggcgaaagc cccgcatttc    420
acgcgcgaac agatcaaagg ctggaaaggt ctgttttgcg gtgatggcgg ttggctggcc    480
gcagcaaaag caattaatgc tatcggccag tttctgaaag aacaaggtgt gaaatttggc    540
ttcggtgaag cgggtacctt caaaaaaccg ctgtttgcag atgctgacga aaaaacgtgc    600
attggcgttg aaaccgtcga tggtacgaaa tattacgcag acaaagtggt tctggctgcg    660
ggcgcttgga gttccacccct ggttgatctg gaagaacagt gtgtcagcaa agcgtgggtg    720
tttgcccaca tccaactgac cccggccgaa gccgcagctt ataaaaacac gccggtgatt    780
tatgatggcg actacggctt tttcatcgaa ccggatgaaa atggcattat caaagtttgc    840
gacgaatttc cgggtttcac ccatttaaa atgcaccagc cgtatggctc accggttccg    900
aaactgatta gtgtcccgcg ttcccatgca aacaccccga ccgatacgta cccgcatgca    960
tcggaagtca cgattaagaa agcgatcaac cgcttcctgc cgcgtttaa cgacaaagaa   1020
ctgttcaatc gcgcgatgtg ctggtgtacc gatacggccg acagcaatct gctggtttgt   1080
gaacacccgc gttggaaagg tttctatctg gcgaccggcg atagcggtca ttcttttaaa   1140
ctgctgccga atattggcaa acacgtcgtg gaactgctgg aaggtcgcct ggaatctgtg   1200
tttaaagatg cgtggcgctg gcgtccgggc tcaggtgatg cactgaaatc gcgtcgcgca   1260
gcaccggcga aagacctggc ggatatgccg ggttggcgta atgaagcgaa aatgtaa     1317

<210> SEQ ID NO 112
<211> LENGTH: 35
<212> TYPE: DNA
<213> ORGANISM: Artificial
<220> FEATURE:
<223> OTHER INFORMATION: primer

<400> SEQUENCE: 112
gaaggagata tacatatggc tccgcgtgcg aatac                                35

<210> SEQ ID NO 113
<211> LENGTH: 35
<212> TYPE: DNA
<213> ORGANISM: Artificial
<220> FEATURE:
<223> OTHER INFORMATION: primer

<400> SEQUENCE: 113
ctcgaattcg gatccttaca ttttcgcttc attac                                35

<210> SEQ ID NO 114
<211> LENGTH: 30
<212> TYPE: DNA
<213> ORGANISM: Artificial
```

```
<220> FEATURE:
<223> OTHER INFORMATION: primer

<400> SEQUENCE: 114
ggatccgaat tcgagctccg tcgacaagct                                          30

<210> SEQ ID NO 115
<211> LENGTH: 30
<212> TYPE: DNA
<213> ORGANISM: Artificial
<220> FEATURE:
<223> OTHER INFORMATION: primer

<400> SEQUENCE: 115
atgtatatct ccttcttaaa gttaaacaaa                                          30

<210> SEQ ID NO 116
<211> LENGTH: 30
<212> TYPE: DNA
<213> ORGANISM: Artificial
<220> FEATURE:
<223> OTHER INFORMATION: primer

<400> SEQUENCE: 116
ttgcagatca tgtttatttg caccgctgat                                          30

<210> SEQ ID NO 117
<211> LENGTH: 30
<212> TYPE: DNA
<213> ORGANISM: Artificial
<220> FEATURE:
<223> OTHER INFORMATION: primer

<400> SEQUENCE: 117
gtgtctctgg aagcgtttga tatgtggaaa                                          30

<210> SEQ ID NO 118
<211> LENGTH: 24
<212> TYPE: DNA
<213> ORGANISM: Artificial
<220> FEATURE:
<223> OTHER INFORMATION: primer

<400> SEQUENCE: 118
tgtatctgca cgattcgacg tcat                                                24

<210> SEQ ID NO 119
<211> LENGTH: 30
<212> TYPE: DNA
<213> ORGANISM: Artificial
<220> FEATURE:
<223> OTHER INFORMATION: primer

<400> SEQUENCE: 119
tcgtgcagat acaaacgtga ttgtcgtcgg                                          30

<210> SEQ ID NO 120
<211> LENGTH: 30
<212> TYPE: DNA
<213> ORGANISM: Artificial
<220> FEATURE:
<223> OTHER INFORMATION: primer

<400> SEQUENCE: 120
tcgtgcagat acacaggtga ttgtcgtcgg                                          30
```

<210> SEQ ID NO 121
<211> LENGTH: 30
<212> TYPE: DNA
<213> ORGANISM: Artificial
<220> FEATURE:
<223> OTHER INFORMATION: primer

<400> SEQUENCE: 121
gccatagggt tgatgttcct tgaagcgcga                               30

<210> SEQ ID NO 122
<211> LENGTH: 30
<212> TYPE: DNA
<213> ORGANISM: Artificial
<220> FEATURE:
<223> OTHER INFORMATION: primer

<400> SEQUENCE: 122
gacgaattcc caggatattc gcgcttcaag                               30

<210> SEQ ID NO 123
<211> LENGTH: 28
<212> TYPE: DNA
<213> ORGANISM: Artificial
<220> FEATURE:
<223> OTHER INFORMATION: primer

<400> SEQUENCE: 123
catggccggc tgattgagcc gatggaat                                 28

<210> SEQ ID NO 124
<211> LENGTH: 30
<212> TYPE: DNA
<213> ORGANISM: Artificial
<220> FEATURE:
<223> OTHER INFORMATION: primer

<400> SEQUENCE: 124
ttggacacat ttaaaattcc atcggctcaa                               30

<210> SEQ ID NO 125
<211> LENGTH: 30
<212> TYPE: DNA
<213> ORGANISM: Artificial
<220> FEATURE:
<223> OTHER INFORMATION: primer

<400> SEQUENCE: 125
ctcaacgcca atgcaagttg tgccttcatc                               30

<210> SEQ ID NO 126
<211> LENGTH: 30
<212> TYPE: DNA
<213> ORGANISM: Artificial
<220> FEATURE:
<223> OTHER INFORMATION: primer

<400> SEQUENCE: 126
caaccccttt tcaaagatga aggcacaact                               30

<210> SEQ ID NO 127
<211> LENGTH: 30
<212> TYPE: DNA
<213> ORGANISM: Artificial
<220> FEATURE:
<223> OTHER INFORMATION: primer

<400> SEQUENCE: 127
caaccccttt tcgcggatga aggcacaact                                    30

<210> SEQ ID NO 128
<211> LENGTH: 30
<212> TYPE: DNA
<213> ORGANISM: Artificial
<220> FEATURE:
<223> OTHER INFORMATION: primer

<400> SEQUENCE: 128
gtcagcgtaa tatttggtac catctgccgt                                    30

<210> SEQ ID NO 129
<211> LENGTH: 30
<212> TYPE: DNA
<213> ORGANISM: Artificial
<220> FEATURE:
<223> OTHER INFORMATION: primer

<400> SEQUENCE: 129
tgcattggcg ttgcgacggc agatggtacc                                    30

<210> SEQ ID NO 130
<211> LENGTH: 30
<212> TYPE: DNA
<213> ORGANISM: Artificial
<220> FEATURE:
<223> OTHER INFORMATION: primer

<400> SEQUENCE: 130
ccagcacaag gcgcgattga agagctcctt                                    30

<210> SEQ ID NO 131
<211> LENGTH: 30
<212> TYPE: DNA
<213> ORGANISM: Artificial
<220> FEATURE:
<223> OTHER INFORMATION: primer

<400> SEQUENCE: 131
cctcgatttc aggccaagga gctcttcaat                                    30

<210> SEQ ID NO 132
<211> LENGTH: 30
<212> TYPE: DNA
<213> ORGANISM: Artificial
<220> FEATURE:
<223> OTHER INFORMATION: primer

<400> SEQUENCE: 132
tgtacaccag cacaaggcgc gattgaagag                                    30

<210> SEQ ID NO 133
<211> LENGTH: 30
<212> TYPE: DNA
<213> ORGANISM: Artificial
<220> FEATURE:
<223> OTHER INFORMATION: primer

<400> SEQUENCE: 133
tttcaggaca agaaactctt caatcgcgcc                                    30

<210> SEQ ID NO 134

```
<211> LENGTH: 30
<212> TYPE: DNA
<213> ORGANISM: Artificial
<220> FEATURE:
<223> OTHER INFORMATION: primer

<400> SEQUENCE: 134
ctggccgata gcattaattg cttttgctgc                                      30

<210> SEQ ID NO 135
<211> LENGTH: 30
<212> TYPE: DNA
<213> ORGANISM: Artificial
<220> FEATURE:
<223> OTHER INFORMATION: primer

<400> SEQUENCE: 135
gatctgaaag aacaaggtgt gaaatttggc                                      30

<210> SEQ ID NO 136
<211> LENGTH: 30
<212> TYPE: DNA
<213> ORGANISM: Artificial
<220> FEATURE:
<223> OTHER INFORMATION: primer

<400> SEQUENCE: 136
tttcagaaac tggccgatag cattaattgc                                      30

<210> SEQ ID NO 137
<211> LENGTH: 30
<212> TYPE: DNA
<213> ORGANISM: Artificial
<220> FEATURE:
<223> OTHER INFORMATION: primer

<400> SEQUENCE: 137
cgacaaggtg tgaaatttgg cttcggtgaa                                      30
```